(12) United States Patent
Swidorski et al.

(10) Patent No.: US 12,275,718 B2
(45) Date of Patent: Apr. 15, 2025

(54) SMALL MOLECULE INHIBITORS OF GALECTIN-3

(71) Applicant: BRISTOL-MYERS SQUIBB COMPANY, Princeton, NJ (US)

(72) Inventors: Jacob Swidorski, Doylestown, PA (US); Brett R. Beno, Yardley, PA (US); David S. Yoon, Yardley, PA (US); Alicia Regueiro-Ren, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 856 days.

(21) Appl. No.: 17/299,325

(22) PCT Filed: Dec. 4, 2019

(86) PCT No.: PCT/US2019/064366
§ 371 (c)(1),
(2) Date: Jun. 3, 2021

(87) PCT Pub. No.: WO2020/117883
PCT Pub. Date: Jun. 11, 2020

(65) Prior Publication Data
US 2022/0009913 A1    Jan. 13, 2022

Related U.S. Application Data

(60) Provisional application No. 62/776,282, filed on Dec. 6, 2018.

(51) Int. Cl.
    *C07D 405/14*    (2006.01)
(52) U.S. Cl.
    CPC .................. *C07D 405/14* (2013.01)
(58) Field of Classification Search
    CPC .................................................. C07D 405/14
    See application file for complete search history.

(56) References Cited

U.S. PATENT DOCUMENTS

| 11,267,811 B2 * | 3/2022 | Jalagam | A61P 35/00 |
| 2014/0099319 A1 | 4/2014 | Traber | |
| 2021/0147408 A1 * | 5/2021 | Jalagam | C07D 417/14 |

FOREIGN PATENT DOCUMENTS

| WO | 2005113568 A1 | 12/2005 |
| WO | 2005113569 A1 | 12/2005 |
| WO | 2014067986 A1 | 5/2014 |
| WO | 2016120403 A1 | 8/2016 |
| WO | 2017080973 A1 | 5/2017 |
| WO | 2018209255 A1 | 11/2018 |

OTHER PUBLICATIONS

Barondes et al. "Galectlns: A Famlly of Animal beta-Galactoalde-Binding Lectlns", Cell, vol. 76(4), pp. 597-598 (1994).
DeBoer, et al., "Galectin-3 in Cardiac Remodeling and Heart", Curr Heart Fail Rep (2010) 7:1-8.
Henderson et al., "The regulation of inflammation bygalectin-3", Immunology Reviews, vol. 230, pp. 160-171 (2009).
Henderson et al., "Galectin-3 Expression and Secretion LinksMacrophages to the Promotion of Renal Fibrosis", American Journal of Pathology, vol. 172(2), pp. 288-298 (2008).
Henderson et al., "Galectin-3 regulates myofibroblast activationand hepatic fibrosis", PNAS, vol. 103(13) pp. 5060-5065 (2006).
Jarvis, et al., "Galectin-3C: Human Lectin for Treatment of Cancer" ACS Symposium Series, vol. 1115. Chapter 12, pp. 195-23 (2012).
Li et al., "Functions of galectin-3 and its role in fibrotic diseases", The Journal of Pharmacology and Experimental Therapeutics, vol. 351(12) pp. 336-343 (2014).
MacKevica et al.,"Synthesis of 1,2,3-triazole-linked galactohybrids and their inhibitory activities on galectins", ARKIVOC, vol. 2014(3), pp. 90.
MacKinnon, et al., "Regulation of Transforming Growth Factor-b1-driven Lung Fibrosis by Galectin-3", Am J Respir Crit Care Med vol. 185, Iss. 5, pp. 537-546 (2012).
Marchiori, et al. "Synthetic 1,2,3-triazole-linked glycoconjugates bind with high affinity to human galectin-3", Bioorganic & Medicinal Chemistry, vol. 23(13), pp. 3414-3425 (2015).
Sharma et al., "Galectin-3 Marks Activated Macrophages in Failure-Prone Hypertrophied Hearts and Contributes to Cardiac Dysfunction", Circulation, vol. 110 pp. 3121-3128 (2004).

* cited by examiner

*Primary Examiner* — Matthew P Coughlin
*Assistant Examiner* — Quincy McKoy
(74) *Attorney, Agent, or Firm* — Jing G. Sun

(57) ABSTRACT

The present disclosure relates to compounds of formula I, which inhibit Gal-3, and include pharmaceutically acceptable salts, compositions comprising such compounds, and methods using and making such compounds and compositions.

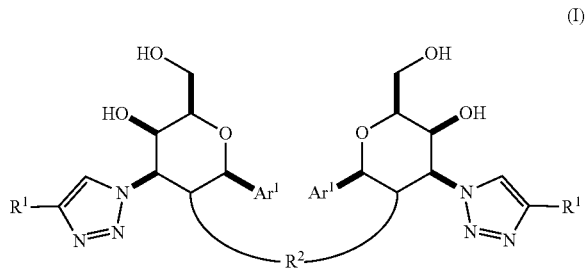

16 Claims, No Drawings

SMALL MOLECULE INHIBITORS OF GALECTIN-3

CROSS-REFERENCE TO RELATED APPLICATIONS

This application is a 371 of International Application No. PCT/US2019/064366 filed on Dec. 4, 2019, which claims the priority benefit of U.S. Provisional Application No. 62/776,282, filed Dec. 6, 2018; the content of which is herein incorporated by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involvement of Gal-3 in the development of fibrotic process in multiple organs such as lung (Am J. Respir. Crit. Care Med. 185: 537-546), liver (PNAS 103: 5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319 and WO2014067986.

DESCRIPTION OF THE INVENTION

The present disclosure relates to compounds of formula I, which inhibit Gal-3, and include pharmaceutically acceptable salts, compositions comprising such compounds, and methods using and making such compounds and compositions.

One aspect of the invention is a compound of formula I

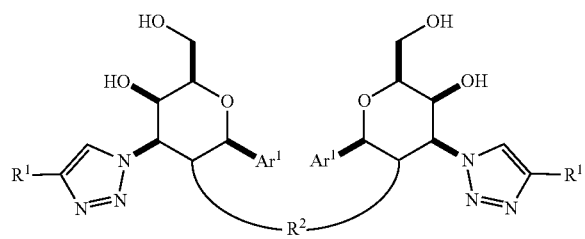

I where:
$R^1$ is $((R^3)(R^4)N)$carbonyl or $Ar^2$;
$R^2$ is —O-$L^1$-O—, —OCON($R^5$)-$L^2$-N($R^5$)C(O)O—, or —O-($L^3$)-CON($R^5$)-$L^2$-N($R^5$)C(O)-($L^3$)-O—;
$L^1$ is alkylene;
$L^2$ is alkylene, or —$CH_2$-Ph-$CH_2$—;
or N($R^5$)-$L^2$-N($R^5$) taken together is piperazinyl, or homopiperazinyl;
$L^3$ is alkylene;
$R^3$ is hydrogen, alkyl, cycloalkyl, benzyl, or halobenzyl;
$R^4$ is hydrogen or alkyl;
or $(R^3)(R^4)N$ taken together is azetidinyl, pyrrolidinyl, piperidinyl, piperazinyl, or morpholinyl, and is substituted with 0-3 substituents selected from halo, alkyl, and alkylcarbonyl;
$R^5$ is hydrogen or alkyl;
$R^6$ is hydrogen or alkyl;
$R^7$ is hydrogen or alkyl;
or $(R^6)(R^7)N$ taken together is azetidinyl, pyrrolidinyl, piperidinyl, piperazinyl, or morpholinyl, and is substituted with 0-3 substituents selected from halo, alkyl, and hydroxy;
$R^8$ is hydrogen, alkyl, alkylcarbonyl, or alkylsulfonyl;
$R^9$ is hydrogen or alkyl;
or $(R^8)(R^9)N$ taken together is azetidinyl, pyrrolidinyl, piperidinyl, piperazinyl, or morpholinyl, and is substituted with 0-3 substituents selected from halo, alkyl, and alkylcarbonyl;
$R^{10}$ is cyano, halo, alkoxy, or $(R^{11})(R^{2})N$;
$R^{11}$ is hydrogen or alkyl;
$R^{12}$ is hydrogen or alkyl;
or $(R^{11})(R^{12})N$ taken together is azetidinyl, pyrrolidinyl, piperidinyl, piperazinyl, or morpholinyl;
$R^{13}$ is hydrogen, alkyl, alkylcarbonyl, alkoxycarbonyl, or alkylsulfonyl;
$R^{14}$ is hydrogen or alkyl;
or $(R^{13})(R^{14})N$ taken together is azetidinyl, pyrrolidinyl, piperidinyl, piperazinyl, or morpholinyl, and is substituted with 0-3 substituents selected from halo, alkyl, and hydroxy;
$R^{15}$ is hydrogen, alkyl, alkylcarbonyl, or alkylsulfonyl;
$R^{16}$ is hydrogen or alkyl;
or $(R^{15})(R^{16})N$ taken together is azetidinyl, pyrrolidinyl, piperidinyl, piperazinyl, or morpholinyl, and is substituted with 0-3 substituents selected from halo, alkyl, and alkylcarbonyl;
$Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, phenyl, or indolyl, and is substituted with 0-3 substituents selected from alkyl, haloalkyl, hydroxyalkyl, alkoxyalkyl, (carboxy)alkyl, (alkoxycarbonyl)alkyl, ($H_2$NCO)alkyl, ($Ar^3$)alkyl, cycloalkyl, hydroxycycloalkyl, alkenyl, alkoxy, alkylthio, alkylsulfonyl, carboxy, alkoxycarbonyl, (alkylNH)carbonyl, (((R^6)(R^7)N)alkylNH)carbonyl, ((pyridinyl)alkylNH)carbonyl, $(R^8)(R^9)N$, and $Ar^3$;
$Ar^2$ is phenyl, pyridinyl, naphthyl, benzoxazolyl, benzothiazolyl, quinolinyl, or quinoxalinyl, and is substituted with 0-5 substituents selected from cyano, halo, alkyl, $(R^{10})$alkyl, haloalkyl, cycloalkyl, $(R^{10})$cycloalkyl, alkoxy, cycloalkoxy, haloalkoxy, and $(R^{13})(R^{14})N$; and
$Ar^3$ is phenyl, naphthalinyl, biphenyl, pyridinyl, pyridazinyl, pyrimidinyl, pyrazinyl, quinolinyl, isoquinolinyl, quinoxainyl, indolyl, indazolyl, benzimidazolyl, benzisoxazolyl, benzisothiazolyl, benzoxazolyl, benzothiazolyl, benzodioxolyl, dihydrobenzodioxinyl, dihydroquinolinonyl, or dihydrobenzothiophene-2,2-dioxide, and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{15})(R^{16})N$;

or $Ar^3$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, nitro, halo, alkyl, haloalkyl, alkoxy, haloalkoxy, alkylthio, carboxy, alkoxycarbonyl, $CONH_2$, and $(R^{15})(R^{16})N$;

or $Ar^3$ is $(alkylSO_2)$phenyl, $(alkylSO_2)$(halo)phenyl, $(aminoSO_2)$phenyl, $(dialkylaminoSO_2)$phenyl, $((alkylNHSO_2)alkyl)$phenyl, (pyrrolyl)phenyl, (imidazolyl)phenyl, (oxazolyl)phenyl, (tetrazolyl)phenyl, ((pyridinyl)methyl)phenyl, phenoxyphenyl, (benzyloxy)phenyl, ((methyl)thiazolyl)phenyl, (thiazolyl)benzenesulfamido, ((methyl)thiadiazolyl)benzenesulfamido, (methyl)benzothiazolonyl, or fluoropyrazolopyrimidinyl;

or a pharmaceutically acceptable salt thereof.

Another aspect of the invention is a compound of formula I where $R^1$ is $Ar^2$; $Ar^1$ is triazolyl substituted with 0-3 substituents selected from alkyl, haloalkyl, hydroxyalkyl, alkoxyalkyl, (carboxy)alkyl, (alkoxycarbonyl)alkyl, $(H_2NCO)$alkyl, $(Ar^3)$alkyl, cycloalkyl, hydroxycycloalkyl, alkenyl, alkoxy, alkylthio, alkylsulfonyl, carboxy, alkoxycarbonyl, (alkylNH)carbonyl, $(((R^6)(R^7)N)alkylNH)$carbonyl, ((pyridinyl)alkylNH)carbonyl, $(R^8)(R^9)N$, and $Ar^3$; $Ar^2$ is phenyl or pyridinyl and is substituted with 0-5 substituents selected from cyano, halo, alkyl, $(R^{10})$alkyl, haloalkyl, cycloalkyl, $(R^{10})$cycloalkyl, alkoxy, cycloalkoxy, haloalkoxy, and $(R^{13})(R^{14})N$; and $Ar^3$ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{15})(R^{16})N$; or a pharmaceutically acceptable salt thereof.

Another aspect of the invention is a compound of formula I where $R^1$ is $Ar^2$; $R^2$ is hydroxy; $Ar^1$ is triazolyl substituted with 0-2 substituents selected from alkyl, haloalkyl, and $Ar^3$; $Ar^2$ is phenyl substituted with 0-5 halo substituents; and $Ar^3$ is phenyl substituted with 0-5 substituents selected from halo, alkyl, haloalkyl, cycloalkyl, alkoxy, and haloalkoxy; or a pharmaceutically acceptable salt thereof.

Another aspect of the invention is a compound of formula I where $R^1$ is $Ar^2$.

Another aspect of the invention is a compound of formula I where $Ar^1$ is triazolyl substituted with 0-3 substituents selected from alkyl, haloalkyl, hydroxyalkyl, alkoxyalkyl, (carboxy)alkyl, (alkoxycarbonyl)alkyl, $(H_2NCO)$alkyl, $(Ar^3)$alkyl, cycloalkyl, hydroxycycloalkyl, alkenyl, alkoxy, alkylthio, alkylsulfonyl, carboxy, alkoxycarbonyl, (alkylNH)carbonyl, $(((R^6)(R^7)N)alkylNH)$carbonyl, ((pyridinyl)alkylNH)carbonyl, $(R^8)(R^9)N$, and $Ar^3$.

Another aspect of the invention is a compound of formula I where $Ar^1$ is triazolyl substituted with 0-2 substituents selected from alkyl, haloalkyl, and $Ar^3$.

Another aspect of the invention is a compound of formula I where $Ar^2$ is phenyl or pyridinyl and is substituted with 0-5 substituents selected from cyano, halo, alkyl, $(R^{10})$alkyl, haloalkyl, cycloalkyl, $(R^{10})$cycloalkyl, alkoxy, cycloalkoxy, haloalkoxy, and $(R^{13})(R^{14})N$.

Another aspect of the invention is a compound of formula I where $Ar^2$ is phenyl substituted with 0-5 halo substituents.

Another aspect of the invention is a compound of formula I where $Ar^3$ is phenyl substituted with 0-5 substituents selected from cyano, halo, alkyl, haloalkyl, alkoxy, and haloalkoxy.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Ar^1$, $Ar^2$, $Ar^3$, $L^1$, $L^2$, and $L^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Alkylene" means a straight or branched divalent alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

ASSAY BUFFER Composition: 25 mM HEPES, 100 mM NaCl, 0.005% Tween 20, 0.05% BSA prepared in sterile water (all reagents from Sigma)

Controls:
Positive Control: 100% DMSO (1 μl)+His-tagged hGal-3 (20 μL)+B-ASF (20 μl)+Anti-His Terbium Antibody (5 μl)+Strep d2 Antibody (5 μl).
Negative Control: 10000 DMSO (1 μl)+His-tagged hGal-3 (20 μL)+Anti His Terbium Antibody (5 μl)+ Strep d2 Aantibody (5 μl).

Stocks Preparation:

|  | Stock Conc. | Intermediate Conc. | Final Assay Conc. | Volume |
|---|---|---|---|---|
| His-tagged hGal-3 | 49.82 μM or can vary batch to batch | 2.525X | 15 nM | 20 μl |
| B-ASF | 25 μM | 2.525X | 15 nM | 20 μl |
| Compounds | 20 mM in 100% DMSO | Various concentration100% DMSO | Various concentration 2% DMSO | 1 μl |
| Anti-His Tb Ab | 5.75 μM | (10X) 10 nM | 1 nM | 5 μl |
| Strep d2 | 16.67 μM | (10X) 200 nM | 20 nM | 5 μl |
| Total Assay volume |  |  |  | 51 μl |

PROTOCOL: The Gal-3 assays were performed in 384 white Opti plates in three replicates at room temperature with gentle shaking at 250-300 rpm From the original stocks, 2.525× working stock concentrations of His-tagged recombinant human Gal-3 (hGal-3) and that of B-ASF were prepared. From the working stock, 20 μl of hGal-3 (15 nM) and 20 μl B-ASF (15 nM) were added to the plates. In Negative Control, only hGal-3 was added. A concentration range of 50× working stocks were prepared for the compounds in 1000% DMSO. Aliquots of 1 uL of the compounds were added to the wells and pre-incubated with 20 μl hGal-3 per well for 30 minutes Then 20 μl B-ASF were added and incubated for another 1 hour. To detect the signal, 5 μL (final conc. of 1.0 nM) terbium labelled Anti-His antibody was added and incubated for 30 min followed by adding 5 μL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in μM).

Pharmaceutical Compostions and Methods of Use

The compounds of this invention inhibit Gal-3. Accordingly, another aspect of the invention is a pharmaceutical composition comprising a therapeutically effective amount of a compound of Formula I, or a pharmaceutically acceptable salt thereof, and a pharmaceutically acceptable carrier.

Another aspect of the invention is use of the compounds of this invention in therapy.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of formula I or Ia.

Another aspect of the invention is a method of treating renal fibrosis, pulmonary fibrosis, hepatic fibrosis, arterial fibrosis and systemic sclerosis comprising administering to a compound of formula I or Ia to a patient.

Another aspect of the invention is a method for treating fibrosis of organs (including liver, kidney, lung, heart and skin) comprising administering to a compound of formula I or Ia to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of formula I or Ia to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of formula I or Ia to a patient.

Another aspect of the invention is a method for treating inflammatory diseases and conditions (including psoriasis, nephropathy, and pneumonia) comprising administering to a compound of formula I or Ia to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of formula I or Ia to a patient.

Another aspect of the invention is a method for treating renal diseases and conditions comprising administering to a compound of formula I or Ia to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of formula I or Ia to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of formula I or Ia to a patient.

Another aspect of the invention is a method for treating pancreatic diseases and conditions comprising administering to a compound of formula I or Ia to a patient.

Another aspect of the invention is a method for treating abnormal angiogenesis-associated diseases and conditions (including arterial obstruction) comprising administering to a compound of formula I or Ia to a patient.

Another aspect of the invention is a method for treating brain-associated diseases and conditions (including cerebral infarction and cerebral hemorrhage) comprising administering to a compound of formula I or Ia to a patient.

Another aspect of the invention is a method for treating neuropathic pain and peripheral neuropathy comprising administering to a compound of formula I or Ia to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of formula I or Ia to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, Remington's Pharmaceutical Sciences, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

Section 1

Analytical LC-MS/HPLC retention time reported for each example and intermediate uses one of the following general analytical LC-MS/HPLC conditions:

LC/MS Methods

Method 1:
   Start % B=2, final % B=98 over 1 min gradient
   Flow Rate=0.8 ml/min
   Wavelength=254
   Solvent A=Water—0.05% TFA
   Solvent B=Acetonitrile—0.05% TFA
   Column=BEH C18 2.1×50 mm Method 2:
   Start % B=0, final % B=100 over 3 min gradient
   Flow Rate=1 ml/min
   Wavelength=220
   Solvent A=5% ACN—95% Water—10 mM ammonium acetate
   Solvent B=95% ACN—5% Water—10 mM ammonium acetate
   Column=XBridge C18 2.1×50 mm, 1.7 µM particles
   Temperature=50° C.

Preparative HPLC Purification Methods:

Method 1: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-68% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 2: Column: Waters Sunfire C18, 30×100 mm, 5-μm particles; Mobile Phase A: 10% ACN-90% water—0.1% TFA; Mobile Phase B: 90% ACN—10% water—0.1% TFA; Gradient 20-100% B over 15 minutes, then hold at 100% B; Flow Rate: 30 mL/min; Fraction collection was triggered by UV, 220 nM wavelength. Fractions containing the product were concentrated under reduced pressure.

Method 3: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 4: The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 32% B, 32-72% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 5: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-84% B over 20 minutes, then a 4-minute hold at 100% B; Flow Rate: 20 mL/min; Column Temperature: 25° C. Fraction collection was triggered by UV signals. Fractions containing the desired product were combined and dried via centrifugal evaporation.

Method 6: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 29% B, 29-69% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 7: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-70% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 8: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-68% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 9: Column: Waters Sunfire C18, 30×100 mm, 5-μm particles; Mobile Phase A: 10% ACN-90% H20—0.1% TFA; Mobile Phase B: 90% ACN—10% H2O—0.1% TFA; Gradient 25-100% B over 15 minutes, then hold at 100% B; Flow Rate: 30 mL/min; Fraction collection was triggered by UV, 220 nM wavelength. Fractions containing the product were concentrated under reduced pressure.

Method 10: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 45% B, 45-90% B over 22 minutes, then a 5-minute hold at 100% B; Flow Rate: 20 mL/min; Column Temperature: 25° C. Fraction collection was triggered by MS signals. Fractions containing the desired product were combined and dried via centrifugal evaporation.

Method 11: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 36% B, 36-76% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 12: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 33% B, 33-73% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 13: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-74% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 14: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 15: Column: Waters Sunfire C18, 30×100 mm, 5-μm particles; Mobile Phase A: 10% ACN-90% water—0.1% TFA; Mobile Phase B: 90% ACN—10% water—0.1% TFA; Gradient 30-100% B over 15 minutes, then hold at 100% B; Flow Rate: 30 mL/min; Fraction collection was triggered by UV, 220 nM wavelength. Fractions containing the product were concentrated under reduced pressure.

Method 16: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 17: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-70% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation.

Method 18: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 52% B, 52-92% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 19: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 51% B, 51-91% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 20: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 20 minutes, then a 6-minute hold at 100% B; Flow Rate: 20 mL/min; Column Temperature: 25° C. Fraction collection was triggered by MS and UV signals. Fractions containing the desired product were combined and dried via centrifugal evaporation.

Method 21: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 36% B, 36-73% B over 20 minutes, then a 8-minute hold at 100% B; Flow Rate: 20 mL/min; Column Temperature: 25° C. Fraction collection was triggered by MS signals. Fractions containing the desired product were combined and dried via centrifugal evaporation.

Method 22: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 36% B, 36-76% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation.

Method 23: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 31% B, 31-71% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 24: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 35% B, 35-75% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Method 25: Column: Waters Sunfire C18, 30×100 mm, 5-μm particles; Mobile Phase A: 10% ACN-90% water—0.1% TFA; Mobile Phase B: 90% ACN—10% water—0.1% TFA; Gradient 20-100% B over 15 minutes, then hold at 100% B; Flow Rate: 30 mL/min; Fraction collection was triggered by UV, 220 nM wavelength. Fractions containing the product were concentrated under reduced pressure.

Preparation of 2-(((2S,3R,4R,5R,6R)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetic acid

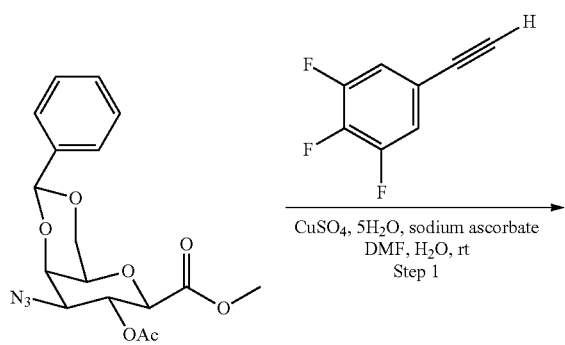

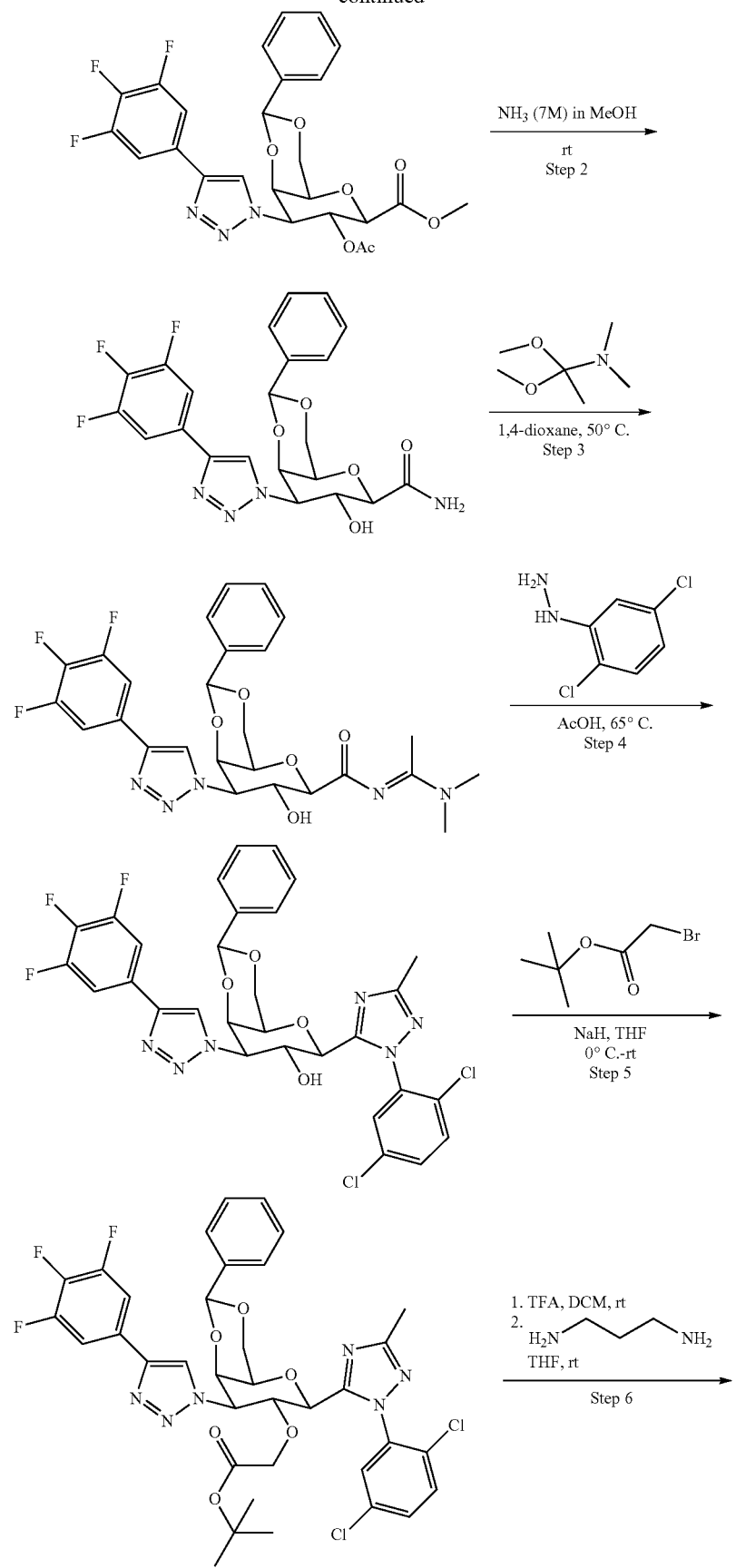

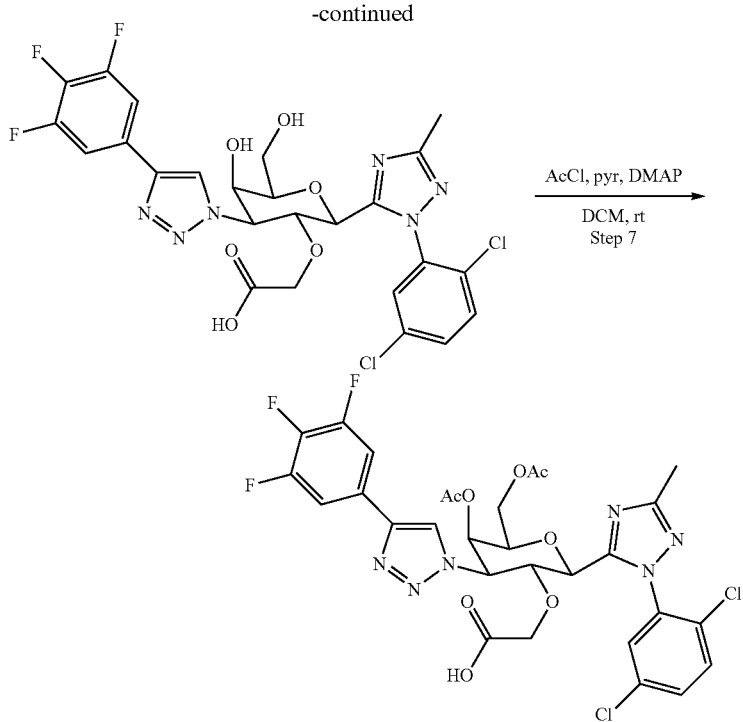

Step 1. Preparation of methyl (2S,4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate: To a flask containing methyl (2S,4aR,6R,7R,8S,8aR)-7-acetoxy-8-azido-2-phenylhexahydropyrano[3,2-d][1,3]dioxine-6-carboxylate (5.0 g, 13.25 mmol) was added copper(II) sulfate pentahydrate (2.316 g, 9.28 mmol) and sodium ascorbate (2.62 g, 13.25 mmol). The mixture was diluted with DMF (100 mL) and water (33.3 mL). 5-ethynyl-1,2,3-trifluorobenzene (3.23 mL, 26.5 mmol) was added and the mixture was stirred at rt for 21.5 h. The mixture was filtered through a plug of celite which was further washed with DCM and methanol followed by DMF. The combined filtrates were concentrated under reduced pressure. The solids were diluted with water and they were collected by filtration. The solids were washed with excess water then with ether. The filtrate was concentrated again and the solids were treated with water, solids were collected and washed with ether a second time. The process was repeated a third time to give the title product as an off-white solid (6.61 g, 12.4 mmol, 94% yield). LCMS: m/e 534.1 (MH$^+$), 0.96 min (Method 1). $^1$H NMR (400 MHz, DMSO-d6) δ 8.82 (s, 1H), 7.91-7.76 (m, 2H), 7.46-7.29 (m, 5H), 5.74-5.65 (m, 2H), 5.61 (s, 1H), 4.58 (d, J=2.2 Hz, 1H), 4.51-4.47 (m, 1H), 4.23-4.11 (m, 2H), 4.01 (s, 1H), 3.66 (s, 3H), 1.84 (s, 3H).

Step 2. Preparation of (2S,4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxamide: To a flask containing methyl (2S,4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate (2.0 g, 3.75 mmol) was added ammonia (7M in methanol) (50 ml, 350 mmol) and the suspension was stirred at rt for 27 h. The mixture was concentrated under reduced pressure, then was diluted with dichloromethane and was concentrated two additional times. The title product was isolated as an off-white solid and was used in the next step with no additional purification. LCMS: m/e 477.3 (MH$^+$), 0.84 min (Method 1). $^1$H NMR (400 MHz, DMSO-d6) δ 8.87 (s, 1H), 7.88-7.75 (m, 2H), 7.58 (br s, 1H), 7.49 (br s, 1H), 7.40-7.23 (m, 5H), 5.54 (s, 1H), 5.49 (br d, J=3.7 Hz, 1H), 5.14 (dd, J=10.8, 3.5 Hz, 1H), 4.55-4.43 (m, 2H), 4.22-4.07 (m, 2H), 3.94 (d, J=9.2 Hz, 1H), 3.90 (s, 1H).

Step 3. Preparation of (2S,4aR,6R,7R,8R,8aR)—N-((E)-1-(dimethylamino)ethylidene)-7-hydroxy-2-phenyl-8-(4-(3,4,5-trifluorophenyl)-1H-1,2,3-triazol-1-yl)hexahydropyrano[3,2-d][1,3]dioxine-6-carboxamide: To a flask containing a suspension of (2S,4aR,6R,7R,8R,8aR)-7-hydroxy-2-phenyl-8-(4-(3,4,5-trifluorophenyl)-1H-1,2,3-triazol-1-yl) hexahydropyrano[3,2-d][1,3]dioxine-6-carboxamide (1.787 g, 3.75 mmol) in 1,4-dioxane (50 mL) was added N,N-dimethylacetamide dimethyl acetal (2.193 mL, 15.00 mmol). The mixture was heated to 50° C. for 15 h, then was cooled to rt, diluted with water (100 mL) and was partitioned with dichloromethane (100 mL). The mixture was stirred until solids dissolved, then the organic layer was removed and the aqueous layer was extracted with dichloromethane (2×75 mL). The organic layers were dried over sodium sulfate, filtered and concentrated under reduced pressure to give the crude product as a light-yellow solid. The crude product was used in the next step with no additional purification. LCMS: m/e 546.3 (MH$^+$), 0.75 min (Method 1). $^1$H NMR (400 MHz, Chloroform-d) δ 8.01 (s, 1H), 7.47-7.32 (m, 7H), 6.29-6.21 (m, 1H), 5.48 (s, 1H), 5.05 (dd, J=10.6, 3.3 Hz, 1H), 4.58 (dd, J=12.7, 1.4 Hz, 1H), 4.52-4.44 (m, 2H), 4.10 (dd, J=12.7, 1.9 Hz, 1H), 4.04 (d, J=9.2 Hz, 1H), 3.76 (d, J=1.1 Hz, 1H), 3.17 (s, 3H), 3.10 (s, 3H), 2.44 (s, 3H).

Step 4. Preparation of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To a solution of (2S,4aR,6R,7R,8R,8aR)—N-((E)-1-(dimethylamino)ethylidene)-7-hydroxy-2-phenyl-8-(4-(3,4,5-trifluorophenyl)-1H-1,2,3- triazol-1-yl)hexahydropyrano[3,2-d][1,3]dioxine-6-carboxamide (2.046 g, 3.75 mmol) in acetic acid (30 ml) was added 2,5-dichlorophenylhydrazine (0.664 g, 3.75 mmol) and the mixture was heated to 65° C. After 4 h of heating, the mixture was cooled to rt then was concentrated under reduced pressure. The residue was diluted with sat. aq. sodium bicarbonate and was extracted with dichloromethane (80 mL, then 2×30 mL). The organic layer was dried over sodium sulfate, filtered and concentrated under reduced pressure. The residue was purified by flash chromatography using a 25-80% EtOAc in hexanes gradient and a 120 g silica gel column. Fractions containing the major peak were combined and concentrated under reduced pressure to give the title product as a tan foam (1.37 g, 2.08 mmol, 55.4% yield over 3 steps). LCMS: m/e 659.4 (MH$^+$), 1.02 min (Method 1). $^1$H NMR (400 MHz, Chloroform-d) δ 8.03 (s, 1H), 7.59 (d, J=1.8 Hz, 1H), 7.51-7.29 (m, 9H), 5.40 (s, 1H), 5.11 (dd, J=10.9, 3.4 Hz, 1H), 4.89-4.80 (m, 1H), 4.65 (d, J=9.0 Hz, 1H), 4.59 (d, J=2.0 Hz, 1H), 4.48 (d, J=3.5 Hz, 1H), 3.95 (dd, J=12.8, 1.8 Hz, 1H), 3.82-3.75 (m, 1H), 3.58 (d, J=0.9 Hz, 1H), 2.45 (s, 3H).

Step 5. Preparation of tert-butyl 2-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)acetate: A solution of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.536 g, 0.813 mmol) in THF (10 mL) was cooled to 0° C. and sodium hydride (0.098 g, 2.438 mmol) was added. The mixture was stirred for 15 minutes and tert-butyl bromoacetate (0.238 mL, 1.626 mmol) was added. The mixture was allowed to warm to rt as the ice bath melted and the mixture was stirred at rt for 24 h. The mixture was carefully diluted with 20 mL of water and was extracted with ethyl acetate (3×20 mL). The organic layers were washed with brine, dried over magnesium sulfate, filtered and concentrated under reduced pressure. The residue was purified by flash chromatography using a 10-50% EtOAc in hexanes gradient and a 40 g silica gel column. The fractions containing the product were combined and concentrated under reduced pressure to give the title product as a white solid (0.494 g, 0.64 mmol, 79% yield). LCMS: m/e 773.5 (MH$^+$), 1.14 min (Method 1). $^1$H NMR (400 MHz, Chloroform-d) δ 8.12 (s, 1H), 7.79-7.67 (m, 1H), 7.56-7.38 (m, 9H), 5.48 (s, 1H), 5.12 (dd, J=10.5, 3.4 Hz, 1H), 4.91-4.76 (m, 1H), 4.47-4.39 (m, 2H), 4.34 (dd, J=12.8, 1.1 Hz, 1H), 4.05 (dd, J=12.8, 1.5 Hz, 1H), 3.89-3.76 (m, 1H), 3.65-3.55 (m, 2H), 2.46 (s, 3H), 1.28 (s, 9H).

Step 6. Preparation of 2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid: To a solution of tert-butyl 2-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)acetate (0.494 g, 0.639 mmol) in dichloromethane (4 mL) was added TFA (2 ml, 26.0 mmol) and the mixture was stirred at rt. After 38 h of stirring, the mixture was concentrated under reduced pressure. The residue was treated with a solution of 1,3-diaminopropane (1M in THF) and was stirred at rt. After 66 h of stirring, the mixture was diluted with several drops and was purified by flash chromatography using a 0-15% MeOH in DCM gradient and a 40 g silica gel column. Fractions containing the product were combined and concentrated under reduced pressure to give the title product as an off-white solid (0.09 g, 0.14 mmol, 22% yield). LCMS: m/e 629.3 (MH$^+$), 0.76 min (Method 1). $^1$H NMR (400 MHz, Chloroform-d) δ 8.24 (s, 1H), 7.60-7.45 (m, 5H), 4.89-4.76 (m, 2H), 4.69-4.60 (m, 1H), 4.36 (d, J=2.0 Hz, 1H), 4.12-4.04 (m, 1H), 3.74-3.51 (m, 4H), 3.44 (d, J=15.6 Hz, 1H), 2.49 (s, 3H).

Step 7. To a suspension of 2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid (0.089 g, 0.14 mmol) in dichloromethane (2 mL) was added pyridine (0.1 mL, 1.236 mmol), DMAP (0.864 mg, 7.07 μmol) and acetyl chloride (0.075 mL, 1.055 mmol). The mixture was stirred at rt for 63 h, then was concentrated under reduced pressure. The residue was purified by flash chromatography using a 0-10% EtOAc in DCM gradient followed by 10% MeOH in DCM. The fractions containing the product were combined and concentrated under reduced pressure to give the title product as an off-white solid (0.10 g, 0.14 mmol, 100% yield). LCMS: m/e 713.4 (MH$^+$), 0.89 min (Method 1).

Dimer Formation and Deprotection

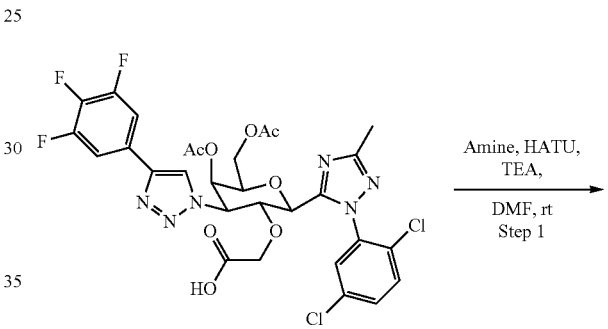

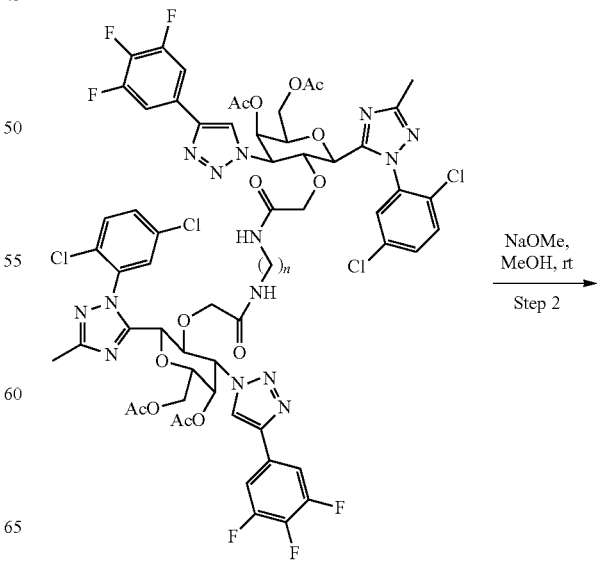

-continued

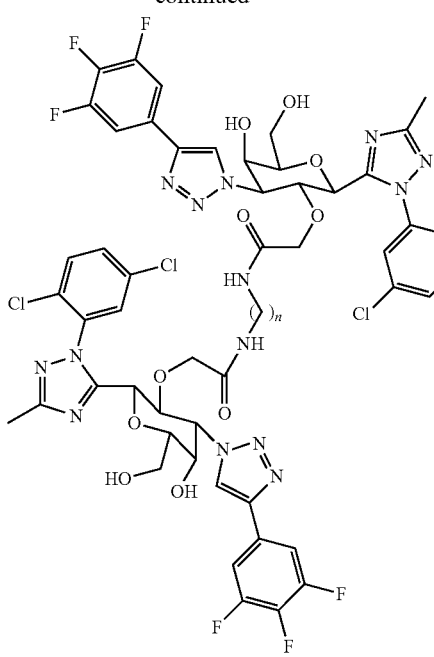

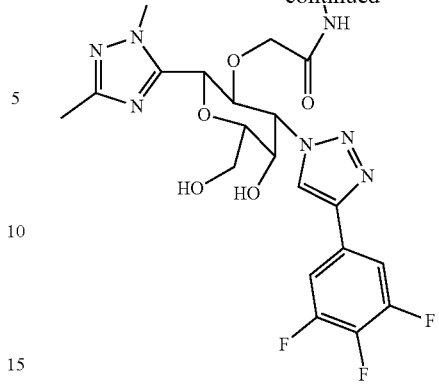

Example 1

Preparation of 2-(((2R,3S,4R,5S,6S)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-(2-(2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetamido)ethyl)acetamide

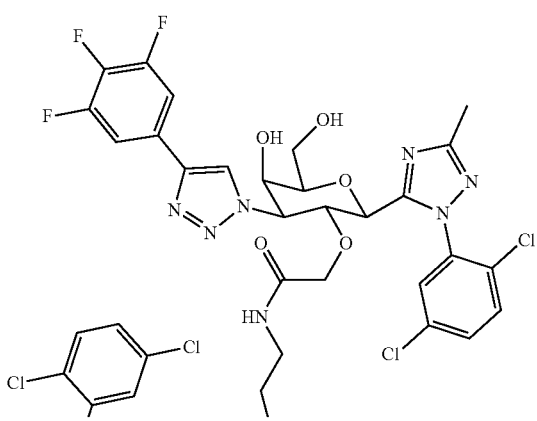

Step 1. Preparation of ((2R,3R,4R,5R,6S)-3-acetoxy-5-(2-((2-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)ethyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate: To a flask containing a solution of 2-(((2S,3R,4R,5R,6R)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetic acid (0.036 g, 0.050 mmol) in DMF (2 mL) and triethylamine (0.035 mL, 0.252 mmol) was added HATU (0.058 g, 0.151 mmol) followed by ethylenediamine (1M in DMF) (0.040 mL, 0.040 mmol). The mixture was stirred at rt for 24 h then was filtered through a plug of glass wool and was purified by preparative HPLC (Method 2). The fractions containing the product were concentrated under reduced pressure to give the title product as a white solid (0.7 mg, 0.0048 mmol, 19% yield). LCMS: m/e 1452.0 (MH$^+$), 1.03 min (Method 1).

Step 2. To a vial containing a solution of ((2R,3R,4R,5R,6S)-3-acetoxy-5-(2-((2-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)ethyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate (0.007 g, 4.82 μmol) in MeOH (1 mL) was added sodium methoxide (25% solution in methanol) (1.1 μl, 4.8 μmol). The mixture was stirred at rt for 16 h. Three drops of 1N HCl was added and the mixture was concentrated under a stream of nitrogen. The mixture was diluted with DMF, filtered through a plug of glass wool and was purified by preparative HPLC (Method 6).

Fractions containing the product were combined and concentrated under reduced pressure to give the title product (2.7 mg, 0.0021 mmol, 44% yield). LCMS: m/e 1281.33 (MH$^+$), 1.84 min (Method 2). $^1$H NMR (500 MHz, DMSO-d6) δ 8.96 (s, 2H), 7.87-7.57 (m, 10H), 6.96 (br s, 2H), 5.50-5.34 (m, 2H), 5.08 (br d, J=10.1 Hz, 2H), 4.80-4.55 (m, 4H), 4.40 (br d, J=9.2 Hz, 2H), 4.10-3.31 (m, 8H), 2.70-2.58 (m, 4H), 2.27 (br s, 6H).

Example 2

Preparation of 2-(((2R,3S,4R,5S,6S)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-(5-(2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetamido)pentyl)acetamide

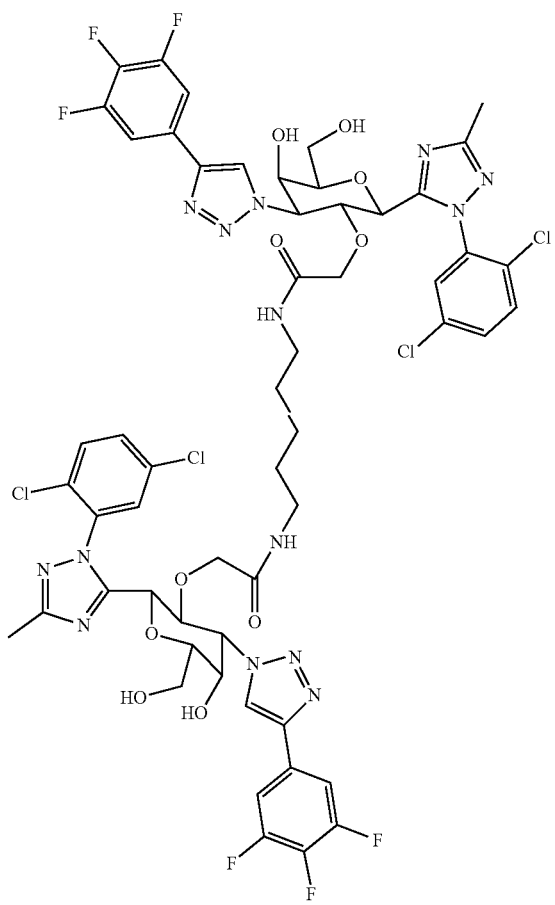 [SMILES: Cc1nc(C2OC(CO)C(O)C(n3cc(-c4cc(F)c(F)c(F)c4)nn3)C2OCC(=O)NCCCCCNC(=O)COC2C(c3nc(C)nn3-c3cc(Cl)ccc3Cl)OC(CO)C(O)C2n2cc(-c3cc(F)c(F)c(F)c3)nn2)n(-c2cc(Cl)ccc2Cl)n1]

Step 1. Preparation of ((2R,3R,4R,5R,6S)-3-acetoxy-5-(2-((5-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)pentyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate: To a flask containing a solution of 2-(((2S,3R,4R,5R,6R)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetic acid (0.056 g, 0.078 mmol) in DMF (2 mL) and triethylamine (0.055 mL, 0.392 mmol) was added HATU (0.090 g, 0.235 mmol) followed by 1,5-diaminopentane (9.2 μl, 0.08 mmol). The mixture was stirred at rt for 45 h, then the mixture was diluted with water (15 mL) and extracted with ethyl acetate (2×15 mL). The combined organic layers were washed with water (3×15 mL), then with brine and were dried over magnesium sulfate, filtered and concentrated under reduced pressure. The residue was purified by flash chromatography using a 10-75% EtOAc in hexanes gradient and a 24 g silica gel column. When the product did not elute, the solvent system was changed to a 0-10% MeOH in DCM gradient. The fractions containing the major product were combined and concentrated under reduced pressure to give the expected dimer (0.020 g, 0.013 mmol, 33% yield) as an off-white film. LCMS: m/e 1494.2 (MH$^+$), 1.02 min (Method 1).

Step 2. To a solution of ((2R,3R,4R,5R,6S)-3-acetoxy-5-(2-((5-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)pentyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate (0.02 g, 0.013 mmol) was added sodium methoxide (25% solution in methanol) (3.0 μl, 0.013 mmol) and the mixture was stirred at rt. After 2.5 h of stirring at rt, 5 drops of 1N HCl was added and the mixture was concentrated under reduced pressure. The residue was diluted with DMF, filtered through a plug of glass wool and was purified by preparative HPLC (Method 7). Fractions containing the products were concentrated under reduced pressure to give the title product (10.2 mg, 0.0076 mmol, 58% yield). LCMS: m/e 1323.66 (MH$^+$), 1.85 min (Method 2). Key 1H NMR peaks: $^1$H NMR (500 MHz, DMSO-d6) δ 8.96 (s, 2H), 7.84-7.62 (m, 10H), 6.62 (br s, 2H), 2.30 (s, 6H), 1.04-0.92 (m, 4H), 0.79 (br d, J=6.4 Hz, 2H). IC$_{50}$=0.001 uM.

Example 3

Preparation 2-(((2R,3S,4R,5S,6S)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-(3-(2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetamido)propyl)acetamide

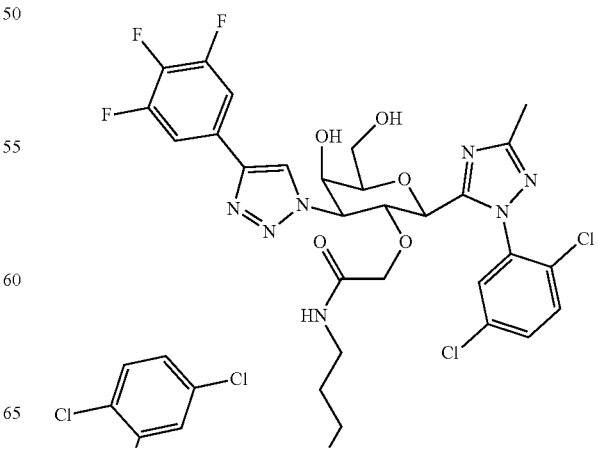

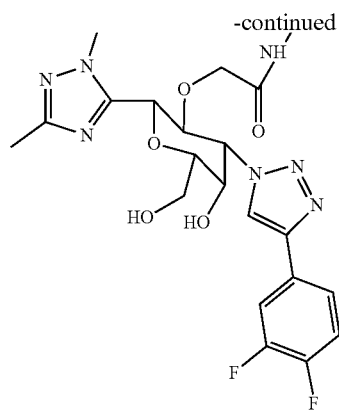

Step 1. Preparation of ((2R,3R,4R,5R,6S)-3-acetoxy-5-(2-((3-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)propyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate: To a flask containing a solution of 2-(((2S,3R,4R,5R,6R)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetic acid (0.034 g, 0.048 mmol) in DMF (1 mL) and triethylamine (0.033 mL, 0.238 mmol) was added HATU (0.054 g, 0.143 mmol) followed by 1,3-diaminopropane (1M in DMF) (0.038 mL, 0.038 mmol). The mixture was stirred at rt for 24 h, then was filtered through a plug of glass wool and was purified by preparative HPLC (Method 2). Fractions containing the product were combined and concentrated under reduced pressure to give the title product (0.007 g, 0.0047 mmol, 20% yield) as a white solid. LCMS: m/e 1466.1 (MH+), 1.03 min (Method 1).

Step 2. To a solution of ((2R,3R,4R,5R,6S)-3-acetoxy-5-(2-((3-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)propyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate (0.007 g, 4.7 µmol) in Methanol (1 mL) was added sodium methoxide (25% in methanol) (1.093 µl, 4.78 µmol) and the mixture was stirred at rt for 16 h. Three drops of 1N HCl was added and the mixture was concentrated under a stream of nitrogen. The mixture was diluted with DMF, filtered through a plug of glass wool and was purified by preparative HPLC (Method 8). Fractions containing the product were concentrated under reduced pressure to give the title product (1.9 mg, 0.0015 mmol, 32% yield). LCMS: m/e 1295.86 (MH+), 1.84 min (Method 2). ¹H NMR (500 MHz, DMSO-d6) δ 9.03-8.89 (m, 2H), 7.85-7.59 (m, 10H), 6.91-6.69 (m, 2H), 5.42 (br d, J=5.8 Hz, 2H), 5.10 (br d, J=13.4 Hz, 2H), 4.73 (br t, J=9.8 Hz, 2H), 4.64-4.55 (m, 2H), 4.48-4.37 (m, 2H), 3.93-3.85 (m, 2H), 3.77 (br d, J=15.0 Hz, 2H), 3.65-3.52 (m, 2H), 5.33-3.14 (m, 4H), 2.67-2.54 (m, 4H), 2.27 (s, 6H), 1.14-0.85 (m, 2H).

Example 4

Preparation of 2-(((2R,3S,4R,5S,6S)-2-(1-(2,5-dichlorophenyl)-3-methyl-11H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-(4-(2-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetamido)butyl)acetamide

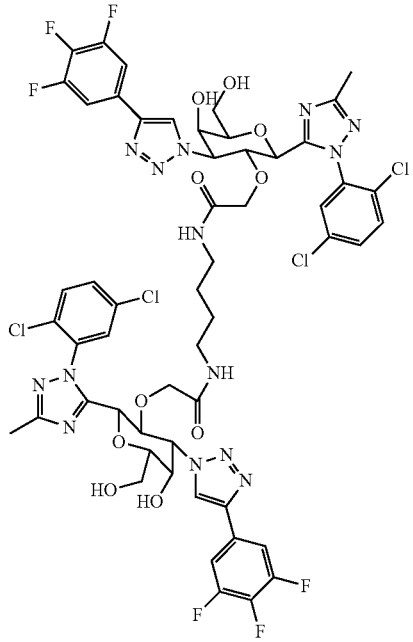 [SMILES: Cc1nc(C2OC(CO)C(O)C(n3cc(-c4cc(F)c(F)c(F)c4)nn3)C2OCC(=O)NCCCCNC(=O)COC2C(c3nc(C)nn3-c3cc(Cl)ccc3Cl)OC(CO)C(O)C2n2cc(-c3cc(F)c(F)c(F)c3)nn2)n(-c2cc(Cl)ccc2Cl)n1]

Step 1. Preparation of ((2R,3R,4R,5R,6S)-3-acetoxy-5-(2-((4-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)butyl)amino)-2-oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate: To a flask containing a solution of 2-(((2S,3R,4R,5R,6R)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetic acid (0.031 g, 0.043 mmol) in DMF (1 mL) and triethylamine (0.030 mL, 0.217 mmol) was added HATU (0.050 g, 0.130 mmol) followed by 1,4-diaminobutane (1M in DMF) (0.035 mL, 0.035 mmol). The mixture was stirred at rt for 24 h, then was filtered through a plug of glass wool and was purified by prep HPLC (Method 2). Fractions containing the product were combined and concentrated under reduced pressure to give the title product (0.007 g, 0.0047 mmol, 22% yield) as a white solid. LCMS: m/e 1480.0 (MH+), 1.02 min (Method 1).

Step 2. To a solution of ((2R,3R,4R,5R,6S)-3-acetoxy-5-(2-((4-(2-(((2R,3S,4S,5S,6S)-5-acetoxy-6-(acetoxymethyl)-2-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-3-yl)oxy)acetamido)butyl)amino)-2- oxoethoxy)-6-(1-(2,5-dichlorophenyl)-3-methyl-1H-1,2,4-triazol-5-yl)-4-(4-(3,4,5-trifluorophenyl)-1H-1,2,3-triazol-1-yl)tetrahydro-2H-pyran-2-yl)methyl acetate (0.007 g, 4.7 μmol) in methanol (0.5 mL) was added sodium methoxide (25% in methanol) (1.270 μl, 5.55 μmol) and the mixture was stirred at rt for 16 h. Three drops of 1N HCl was added and the mixture was concentrated under a stream of nitrogen. The mixture was diluted with DMF, filtered through a plug of glass wool and was purified by preparative HPLC (Method 6). Fractions containing the product were concentrated under reduced pressure to give the title product (2.4 mg, 0.0018 mmol, 38% yield). LCMS: m/e 1309.09 (MH+), 1.86 min (Method 2). Key 1H NMR peaks: ¹H NMR (500 MHz, DMSO-d6) δ 9.03 (s, 2H), 7.89-7.58 (m, 10H), 6.79-6.61 (m, 2H), 2.34 (s, 6H), 0.96 (br s, 4H).

Synthesis of Carboxylic Acid Intermediate (7)

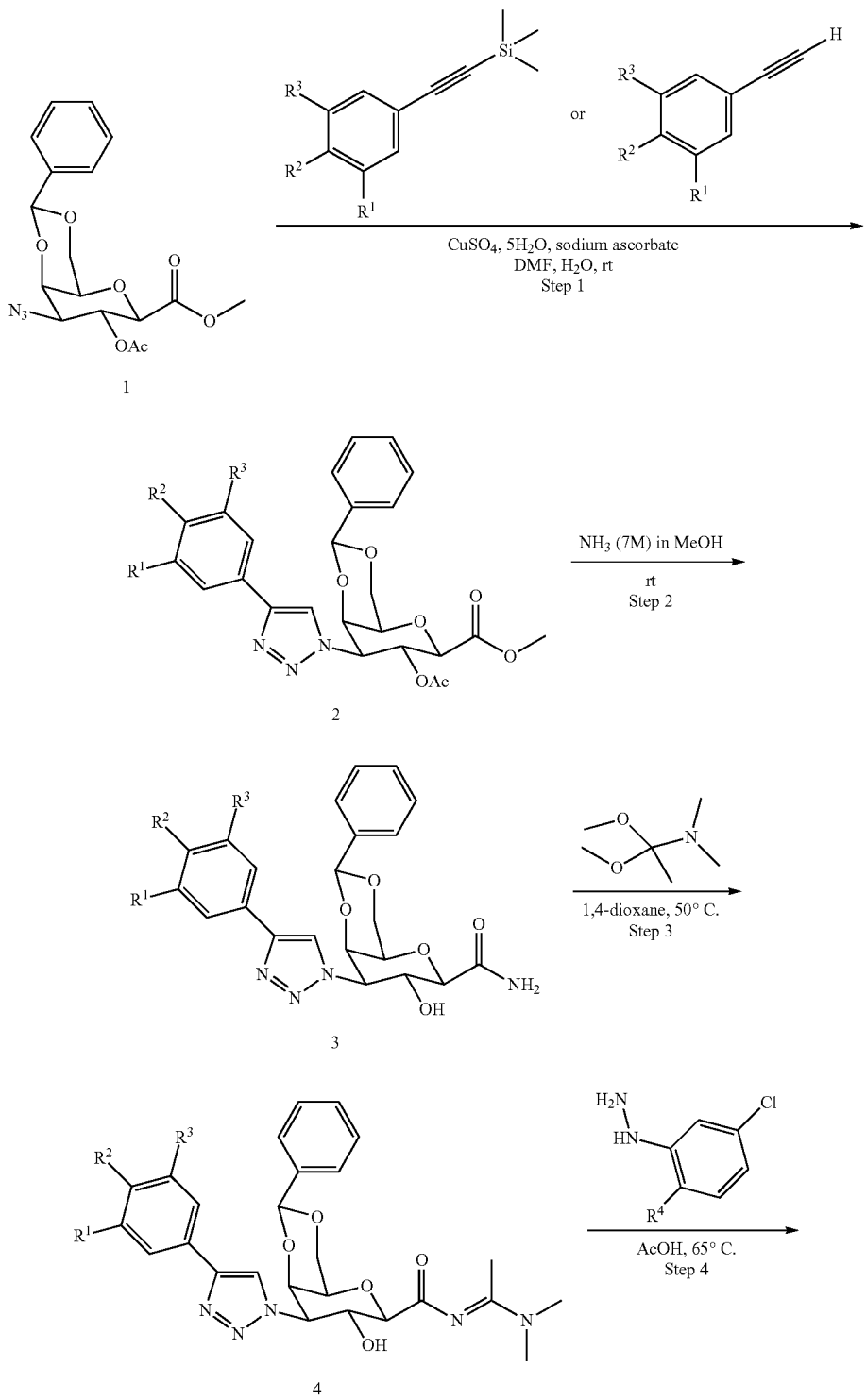

-continued

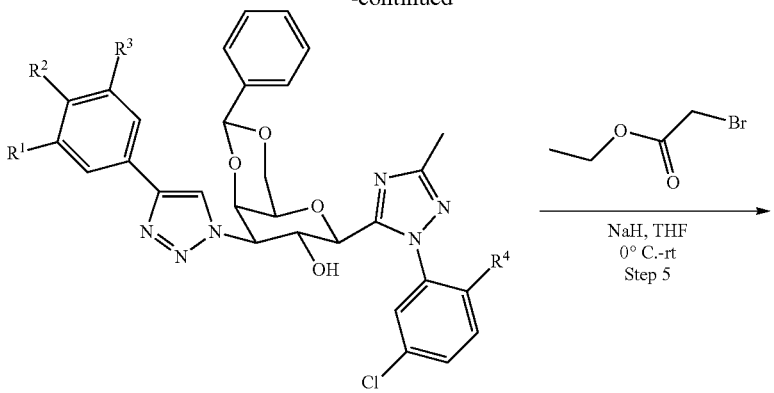

5

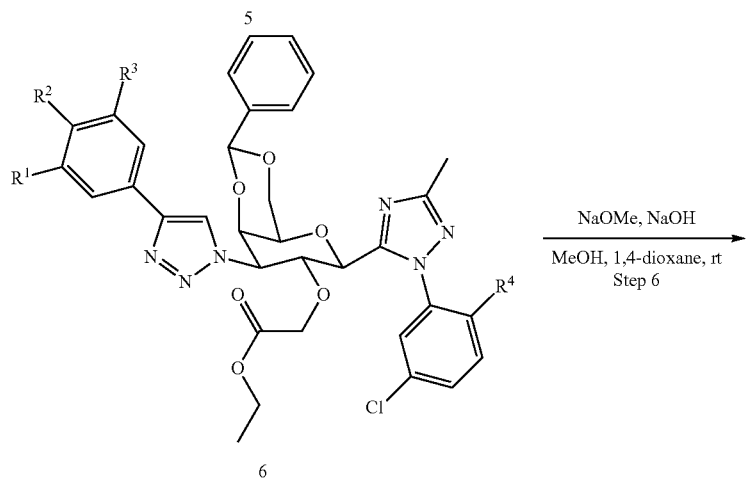

6

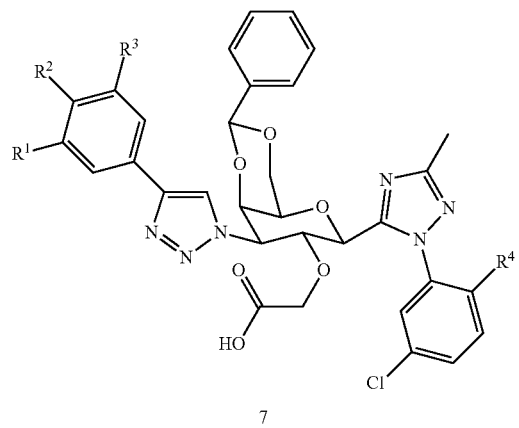

7

Step 1. General procedure for the formation of 1,2,3-triazole (2): To a flask containing methyl (2S,4aR,6R,7R,8S,8aR)-7-acetoxy-8-azido-2-phenylhexahydropyrano[3,2-d][1,3]dioxine-6-carboxylate (1 equiv.) was added copper (II)sulfate pentahydrate (0.7 equiv.) and sodium ascorbate (1 equiv.). The mixture was diluted with DMF and water (3:1, 0.075M solution). The alkynyl silane or alkyne (1.2-2 equiv.) was added and the mixture was stirred at rt. After 18 h of stirring at rt, the mixture was filtered through a plug of celite which was further washed with a DCM:MeOH mixture (4:1). In cases where the product was less soluble in the DCM:MeOH mixture, the celite was further washed with DMF to be sure no product remained on the filter. The mixture was concentrated under reduced pressure then was diluted with water (75 mL) and with ether (75 mL). The solids were collected by filtration and were washed with water followed by ether to give the expected product.

Step 2. General procedure for primary amide (3) formation: To a flask containing the 1,2,3-triazole (2) was added ammonia (7M in methanol, 106 equiv.) and the suspension was stirred at rt overnight. Generally the reaction was complete overnight, but in cases where the starting material was especially insoluble, additional methanol was added and the mixture was stirred until no starting material was present (up to five days). The mixture was concentrated under reduced pressure, then was diluted with DCM and concentrated two additional times. The crude product was used in the next step with no additional purification.

Step 3. General procedure for the synthesis of acetamide (4): To a flask containing primary amide (3) was added 1,4-Dioxane (0.06M solution) followed by N,N-dimethylacetamide dimethyl (4 equiv.). The mixture was heated to 50° C. for 7.5 h, then was cooled to rt, filtered through a plug of celite to remove the solids (washed with DCM) then was diluted with water (100 mL). The organic layer was collected and the aqueous layer was extracted with dichloromethane (2×75 mL). The combined organic layers were dried over sodium sulfate, filtered and concentrated under reduced pressure. Note: The reaction was also run with the addition of powdered 4 A molecular sieves, but it did not appear to influence the outcome of the reaction. The crude product was used in the next step with no additional purification.

Step 4. General procedure for the synthesis of 1,2,4-triazole (5): To a solution of acetamide (4) in acetic acid (0.12-0.17M solution) was added the substituted hydrazine (0.65-1.0 equiv.) and the mixture was heated to 65° C. After 3.5 h, the mixture was cooled to rt and was concentrated under reduced pressure. The residue was diluted with sat. aq. sodium bicarbonate (40 mL) and was extracted with dichloromethane (3×30 mL). The organic layers were dried over sodium sulfate, filtered and concentrated under reduced pressure. The residue was purified by flash chromatography using a 20-80% EtOAc in hexanes gradient. Product fractions were combined and concentrated to give the 1,2,4-triazole product.

Step 5. General procedure for alkylation of C2 to ester (6): A solution of 1,2,4-triazole (5) (0.291 g, 0.410 mmol) in THF (0.08M solution) was cooled to 0° C. and sodium hydride (60% mineral oil dispersion) (5 equiv.) was added. The mixture was stirred for 15 minutes and ethyl bromoacetate (4 equiv.) was added. The mixture was allowed to warm to rt as the ice bath melted and warmed. After stirring the mixture for 17.5 h, the reaction was carefully quenched with ethanol and the mixture was concentrated under reduced pressure. The residue was diluted with water and was extracted with ethyl acetate. The organic layers were washed with brine, dried over magnesium sulfate, filtered and concentrated under reduced pressure. The residue was purified by flash chromatography using a 10-80% EtOAc in hexanes gradient. The fractions containing the product were combined and concentrated under reduced pressure to give the alkylated product (6).

Step 6. General procedure for the synthesis of carboxylic acid (7): To a suspension of ester (6) in methanol (0.05M solution) was added sodium methoxide (25% in methanol) (0.5 equiv.) and the mixture was stirred at rt. After 2 h, the mixture was diluted with 1,4-dioxane (5 mL) and sodium hydroxide (1N, 5 equiv.) was added. The mixture was stirred at rt for 2 h and LC/MS showed complete conversion to the expected product. The mixture was concentrated under reduced pressure, then was diluted with a solution of sat. aq. ammonium chloride and was extracted with ethyl acetate. The organic layers were washed with brine, dried over sodium sulfate, filtered and concentrated under reduced pressure to give carboxylic acid (7).

Preparation of 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid

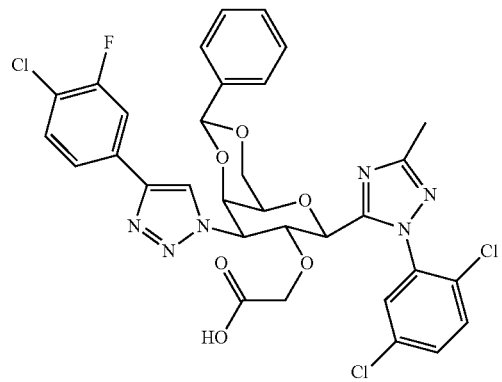 [SMILES: Cc1nc(C2OC3COC(c4ccccc4)OC3C(n3cc(-c4ccc(Cl)c(F)c4)nn3)C2OCC(=O)O)n(-c2cc(Cl)ccc2Cl)n1]

Step 1. Preparation of methyl (2S,4aR,6R,7R,8S,8aR)-7-acetoxy-8-(4-(4-chloro-3-fluorophenyl)-1H-1,2,3-triazol-1-yl)-2-phenylhexahydropyrano[3,2-d][1,3]dioxine-6-carboxylate: The 1,2,3-triazole was prepared from methyl (2S,4aR,6R,7R,8S,8aR)-7-acetoxy-8-azido-2-phenylhexahydropyrano[3,2-d][1,3]dioxine-6-carboxylate (1.5 g, 3.98 mmol) and ((4-chloro-3-fluorophenyl)ethynyl)trimethylsilane (1.803 g, 7.95 mmol) using the General procedure for the formation of 1,2,3-triazole (2). The title compound (1.99 g, 3.74 mmol, 94% yield) was isolated as a light-yellow solid. LCMS: m/e 532.3 (MH$^+$), 0.96 min (Method 1). $^1$H NMR (400 MHz, CHLOROFORM-d) δ 8.06 (s, 1H), 7.59 (dd, J=9.9, 1.5 Hz, 1H), 7.49-7.38 (m, 7H), 5.89 (dd, J=11.0, 9.7 Hz, 1H), 5.52 (s, 1H), 5.20 (dd, J=11.0, 3.3 Hz, 1H), 4.53-4.44 (m, 2H), 4.23 (d, J=9.7 Hz, 1H), 4.12 (dd, J=12.8, 1.8 Hz, 1H), 3.83-3.77 (m, 4H), 1.88 (s, 3H).

Step 2. Preparation of (2S,4aR,6R,7R,8R,8aR)-8-(4-(4-chloro-3-fluorophenyl)-1H-1,2,3-triazol-1-yl)-7-hydroxy-2-phenylhexahydropyrano[3,2-d][1,3]dioxine-6-carboxamide: The primary amide was formed from methyl (2S,4aR,6R,7R,8S,8aR)-7-acetoxy-8-(4-(4-chloro-3-fluorophenyl)-1H-1,2,3-triazol-1-yl)-2-phenylhexahydropyrano[3,2-d][1,3]dioxine-6-carboxylate (1.99 g, 3.74 mmol) using the General procedure for primary amide (3) formation. The title compound (1.78 g, 3.74 mmol, 100% yield) was isolated as an off-white solid. LCMS: m/e 475.3 (MH$^+$), 0.84 min (Method 1). $^1$H NMR (400 MHz, DMSO-d6) δ 8.81 (s, 1H), 7.88 (dd, J=10.7, 1.9 Hz, 1H), 7.77-7.65 (m, 2H), 7.57 (br s, 1H), 7.48 (br s, 1H), 7.38-7.30 (m, 5H), 5.54 (s, 1H), 5.47 (d, J=5.1 Hz, 1H), 5.12 (dd, J=10.6, 3.5 Hz, 1H), 4.56-4.48 (m, 1H), 4.45 (d, J=3.3 Hz, 1H), 4.21-4.07 (m, 2H), 3.93 (d, J=9.5 Hz, 1H), 3.89 (s, 1H).

Step 3. Preparation of (2S,4aR,6R,7R,8R,8aR)-8-(4-(4-chloro-3-fluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide: Acetamide formation of the primary amide (2S,4aR,6R,7R,8R,8aR)-8-(4-(4-chloro-3-fluorophenyl)-1H-1,2,3-triazol-1-yl)-7-hydroxy-2-phenylhexahydropyrano[3,2-d][1,3]dioxine-6-carboxamide (1.1 g, 2.316 mmol) was accomplished using the General procedure for the synthesis of acetamide (4). The title compound (0.75 g, 1.38 mmol, 60% yield) was isolated as a light-yellow solid. LCMS: m/e 544.3 (MH$^+$), 0.76 min (Method 1).

Step 4. Preparation of (2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol: Cyclization of (2S,4aR,6R,7R,8R,8aR)-8-(4-(4-chloro-3-fluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (0.75 g, 1.379 mmol) was accomplished using the General procedure for the synthesis of 1,2,4-triazole (5). The title compound (0.278 g, 0.423 mmol, 31% yield) was isolated as an off-white foam. LCMS: m/e 659.2 (MH$^+$), 1.01 min (Method 1). $^1$H NMR (400 MHz, CDCl$_3$) δ 8.07 (s, 1H), 7.62 (td, J=10.7, 1.9 Hz, 2H), 7.55-7.29 (m, 9H), 5.40 (s, 1H), 5.12 (dd, J=10.8, 3.3 Hz, 1H), 4.90-4.80 (m, 1H), 4.64 (d, J=9.0 Hz, 1H), 4.56 (d, J=2.2 Hz, 1H), 4.48 (d, J=2.6 Hz, 1H), 3.95 (dd, J=12.7, 1.7 Hz, 1H), 3.79 (dd, J=12.7, 1.2 Hz, 1H), 3.57 (d, J=1.1 Hz, 1H), 2.45 (s, 3H).

Step 5. Preparation of ethyl 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-11H-1,2,4-triazol-5-yl)-2-phenylhexahydropyrano[3,2-d][1,3]dioxin-7-yl)oxy)acetate: Alkylation of the C2 alcohol, (2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.287 g, 0.436 mmol), was accomplished using the General procedure for alkylation of C2 to ester (6). The title compound (0.100 g, 0.134 mmol, 31% yield) was isolated as an off-white solid. LCMS: m/e 745.4 (MH$^+$), 1.09 min (Method 1). $^1$H NMR (400 MHz, CDCl$_3$) δ 8.15 (s, 1H), 7.69 (s, 1H), 7.64 (dd, J=10.0, 1.9 Hz, 1H), 7.54-7.38 (m, 9H), 5.49 (s, 1H), 5.15 (dd, J=10.5, 3.4 Hz, 1H), 4.85 (br t, J=9.0 Hz, 1H), 4.46-4.40 (m, 2H), 4.34 (dd, J=12.8, 1.3 Hz, 1H), 4.05 (dd, J=12.7, 1.7 Hz, 1H), 4.00-3.89 (m, 3H), 3.71-3.60 (m, 2H), 2.46 (s, 3H), 1.10 (t, J=7.2 Hz, 3H).

Step 6. Preparation of 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid: Hydrolysis of the carboxylate, ethyl 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetate (0.100 g, 0.134 mmol), was accomplished using the General procedure for the synthesis of carboxylic acid (7). The title compound (0.087 g, 0.122 mmol, 91% yield) was isolated as a white solid. LCMS: m/e 715.4 (MH$^+$), 0.99 min (Method 1). $^1$H NMR (400 MHz, CDCl$_3$) δ 8.12 (s, 1H), 7.58 (br d, J=8.6 Hz, 2H), 7.52-7.36 (m, 9H), 5.44 (s, 1H), 5.21 (br dd, J=9.6, 2.5 Hz, 1H), 4.86 (br d, J=9.0 Hz, 1H), 4.50 (br t, J=9.4 Hz, 1H), 4.38 (d, J=2.6 Hz, 1H), 3.92 (br d, J=12.8 Hz, 1H), 3.77-3.61 (m, 2H), 3.57 (d, J=1.1 Hz, 1H), 3.33 (br d, J=15.6 Hz, 1H), 2.47 (s, 3H).

Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid

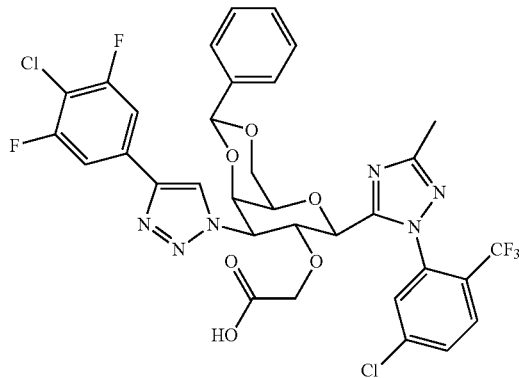 [SMILES: Cc1nc(C2OC3COC(c4ccccc4)OC3C(n3cc(-c4cc(F)c(Cl)c(F)c4)nn3)C2OCC(=O)O)n(-c2cc(Cl)ccc2C(F)(F)F)n1]

Step 1. Preparation of methyl (2S,4aR,6R,7R,8S,8aR)-7-acetoxy-8-(4-(4-chloro-3-fluorophenyl)-1H-1,2,3-triazol-1-yl)-2-phenylhexahydropyrano[3,2-d][1,3]dioxine-6-carboxylate: The 1,2,3-triazole was prepared from methyl (2S,4aR,6R,7R,8S,8aR)-7-acetoxy-8-azido-2-phenylhexahydropyrano[3,2-d][1,3]dioxine-6-carboxylate (1.5 g, 3.98 mmol) and ((4-chloro-3,5-difluorophenyl)ethynyl)trimethylsilane (1.946 g, 7.95 mmol) using the General procedure for the formation of 1,2,3-triazole (2). The title compound (2.19 g, 3.98 mmol, 100% yield) was isolated as an off-white solid. LCMS: m/e 550.3 (MH$^+$), 0.99 min (Method 1). $^1$H NMR (500 MHz, CDCl$_3$) δ 8.07 (s, 1H), 7.49-7.37 (m, 7H), 5.88 (t, J=10.3 Hz, 1H), 5.52 (s, 1H), 5.20 (dd, J=11.0, 3.3 Hz, 1H), 4.52-4.45 (m, 2H), 4.23 (d, J=9.6 Hz, 1H), 4.15-4.09 (m, 1H), 3.84-3.77 (m, 4H), 1.88 (s, 3H).

Step 2. Preparation of (2S,4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide: The primary amide was formed from methyl (2S,4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (2.189 g, 3.98 mmol) using the General procedure for primary amide (3) formation. The title compound (1.96 g, 3.98 mmol, 100% yield) was isolated as an off-white solid. LCMS: m/e 493.2 (MH$^+$), 0.87 min (Method 1). $^1$H NMR (400 MHz, DMSO-d6) δ 8.93 (s, 1H), 7.81 (d, J=8.4 Hz, 2H), 7.62-7.43 (m, 2H), 7.39-7.26 (m, 5H), 5.54 (s, 1H), 5.48 (d, J=4.8 Hz, 1H), 5.14 (dd, J=10.7, 3.6 Hz, 1H), 4.55-4.43 (m, 2H), 4.20-4.06 (m, 2H), 3.93 (d, J=9.5 Hz, 1H), 3.89 (s, 1H).

Step 3. Preparation of (2S,4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide: Acetamide formation of the primary amide (2S,4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (1.38 g, 2.80 mmol) was accomplished using the General procedure for the synthesis of acetamide (4). The crude product was isolated as a light-yellow solid and was used in the next step with no additional purification. LCMS: m/e 562.3 (MH$^+$), 0.78 min (Method 1).

Step 4. (2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol: Cyclization of (2S,4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (0.66 g, 1.174 mmol) was accomplished using the General procedure for the synthesis of 1,2,4-triazole (5). The title compound (0.352 g, 0.496 mmol, 42% yield over 2 steps) was isolated as an off-white foam. LCMS: m/e 709.4 (MH$^+$), 1.06 min (Method 1). $^1$H NMR (400 MHz, CDCl$_3$) δ 8.04 (s, 1H), 7.75 (d, J=8.6 Hz, 1H), 7.68-7.58 (m, 1H), 7.50-7.28 (m, 8H), 5.38 (s, 1H), 5.07 (dd, J=10.7, 3.2 Hz, 1H), 4.82-4.73 (m, 1H), 4.61 (s, 1H), 4.55 (d, J=9.0 Hz, 1H), 4.46 (br d, J=2.9 Hz, 1H), 3.96-3.86 (m, 1H), 3.69 (br d, J=12.3 Hz, 1H), 3.52 (s, 1H), 2.43 (s, 3H).

Step 5. Preparation of ethyl 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetate: Alkylation of the C2 alcohol, (2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (0.291 g, 0.410 mmol), was accomplished using the General procedure for alkylation of C2 to ester (6). The title compound (0.207 g, 0.260 mmol, 63% yield) was isolated as an off-white solid. LCMS: m/e 795.4 (MH$^+$), 1.12 min (Method 1). $^1$H NMR (400 MHz, chloroform-d) δ 8.18 (s, 1H), 7.80 (br d, J=8.4 Hz, 2H), 7.65 (dd, J=8.7, 1.0 Hz, 1H), 7.47-7.40 (m, 7H), 5.49 (s, 1H), 5.13 (dd, J=10.6, 3.5 Hz, 1H), 4.86 (br t, J=9.2 Hz, 1H), 4.41 (d, J=3.1 Hz, 1H), 4.36 (d, J=9.0 Hz, 1H), 4.33 (dd, J=12.8, 1.1 Hz, 1H), 4.05 (dd, J=12.7, 1.2 Hz, 1H), 4.01-3.84 (m, 3H), 3.67 (br d, J=15.6 Hz, 1H), 3.58 (s, 1H), 2.45 (s, 3H), 1.11 (t, J=7.2 Hz, 3H).

Step 6. Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid: Hydrolysis of the carboxylate, ethyl 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetate (0.207 g, 0.260 mmol), was accomplished using the General procedure for the synthesis of carboxylic acid (7). The title compound (0.20 g, 0.26 mmol, 100% yield) was isolated as an off-white solid. LCMS: m/e 767.5 (MH$^+$), 1.02 min (Method 1). $^1$H NMR (400 MHz, DMSO-d6) δ 12.59 (br s, 1H), 9.27 (s, 1H), 8.31-8.13 (m, 1H), 8.09-8.02 (m, 1H), 7.96 (br d, J=8.4 Hz, 1H), 7.82 (br d, J=8.4 Hz, 2H), 7.37 (s, 5H), 5.54 (s, 1H), 5.47 (br dd, J=10.7, 3.0 Hz, 1H), 4.87 (br t, J=9.1 Hz, 1H), 4.62 (br d, J=9.2 Hz, 1H), 4.43 (br d, J=2.9 Hz, 1H), 4.12-4.03 (m, 1H), 3.99-3.78 (m, 3H), 3.67-3.51 (m, 1H), 2.33 (s, 3H).

Preparation of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid

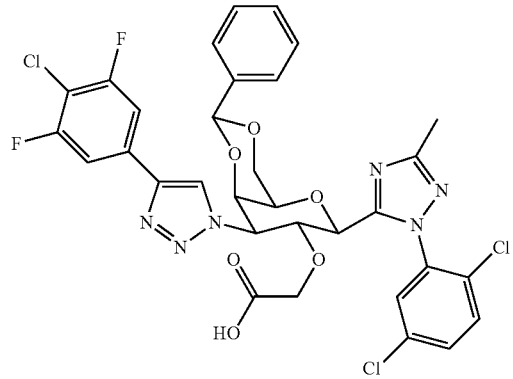 [SMILES: Cc1nc(C2OC3COC(c4ccccc4)OC3C(n3cc(-c4cc(F)c(Cl)c(F)c4)nn3)C2OCC(=O)O)n(-c2cc(Cl)ccc2Cl)n1]

Step 1. Preparation of methyl (2S,4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate: The 1,2,3-triazole was prepared from methyl (2S,4aR,6R,7R,8S,8aR)-7-acetoxy-8-azido-2-phenylhexahydropyrano[3,2-d][1,3]dioxine-6-carboxylate (1.5 g, 3.98 mmol) and ((4-chloro-3,5-difluorophenyl)ethynyl)trimethylsilane (1.946 g, 7.95 mmol) using the General procedure for the formation of 1,2,3-triazole (2). The title compound (2.186 g, 3.98 mmol, 100% yield) was isolated as an off-white solid. LCMS: m/e 550.3 (MH$^+$), 0.99 min (Method 1). $^1$H NMR (500 MHz, chloroform-d) δ 8.07 (s, 1H), 7.49-7.37 (m, 7H), 5.88 (t, J=10.3 Hz, 1H), 5.52 (s, 1H), 5.20 (dd, J=11.0, 3.3 Hz, 1H), 4.52-4.45 (m, 2H), 4.23 (d, J=9.6 Hz, 1H), 4.15-4.09 (m, 1H), 3.84-3.77 (m, 4H), 1.88 (s, 3H).

Step 2. Preparation of (2S,4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide: The primary amide was formed from methyl (2S,4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (2.19 g, 3.98 mmol) using the General procedure for primary amide (3) formation. The title compound (1.96 g, 3.98 mmol, 100% yield) was isolated as an off-white solid. LCMS: m/e 493.2 (MH$^+$), 0.87 min (Method 1). $^1$H NMR (400 MHz, DMSO-d6) δ 8.93 (s, 1H), 7.81 (d, J=8.4 Hz, 2H), 7.62-7.43 (m, 2H), 7.39-7.26 (m, 5H), 5.54 (s, 1H), 5.48 (d, J=4.8 Hz, 1H), 5.14 (dd, J=10.7, 3.6 Hz, 1H), 4.55-4.43 (m, 2H), 4.20-4.06 (m, 2H), 3.93 (d, J=9.5 Hz, 1H), 3.89 (s, 1H).

Step 3. Preparation of (2S,4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide: Acetamide formation of the primary amide (2S,4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (1.38 g, 2.80 mmol) was accomplished using the General procedure for the synthesis of acetamide (4). The crude product, a light-yellow solid, was used in the next step with no additional purification. LCMS: m/e 562.2 (MH$^+$), 0.79 min (Method 1).

Step 4. Preparation of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol: Cyclization of (2S,4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (0.93 g, 1.655 mmol) was accomplished using the General procedure for the synthesis of 1,2,4-triazole (5). The title compound (0.442 g, 0.654 mmol, 40% yield) was isolated as an off-white foam. LCMS: m/e 675.4 (MH$^+$), 1.04 min (Method 1). $^1$H NMR (400 MHz, Chloroform-d) δ 8.08 (s, 1H), 7.59 (d, J=1.8 Hz, 1H), 7.51-7.40 (m, 4H), 7.39-7.29 (m, 5H), 5.40 (s, 1H), 5.12 (dd, J=10.9, 3.4 Hz, 1H), 4.84 (ddd, J=10.8, 9.0, 2.2 Hz, 1H), 4.65 (d, J=9.0 Hz, 1H), 4.61 (d, J=2.2 Hz, 1H), 4.49 (d, J=3.1 Hz, 1H), 3.95 (dd, J=12.7, 1.7 Hz, 1H), 3.78 (dd, J=12.8, 1.3 Hz, 1H), 3.58 (d, J=0.9 Hz, 1H), 2.45 (s, 3H).

Step 5. Preparation of ethyl 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetate: Alkylation of the C2 alcohol, (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.442 g, 0.654 mmol), was accomplished using the General procedure for alkylation of C2 to ester (6). The title compound (0.422 g, 0.554 mmol, 85% yield) was isolated as an off-white solid. LCMS: m/e 761.3 (MH$^+$), 1.11 min (Method 1). $^1$H NMR (400 MHz, CHLOROFORM-d) δ 8.17 (s, 1H), 7.68 (br d, J=0.9 Hz, 1H), 7.54-7.38 (m, 9H), 5.49 (s, 1H), 5.15 (dd, J=10.6, 3.5 Hz, 1H), 4.91-4.79 (m, 1H), 4.46-4.40 (m, 2H), 4.34 (dd, J=12.8, 1.1 Hz, 1H), 4.05 (dd, J=12.8, 1.5 Hz, 1H), 4.00-3.89 (m, 3H), 3.68 (br d, J=15.8 Hz, 1H), 3.63 (s, 1H), 2.46 (s, 3H), 1.11 (t, J=7.2 Hz, 3H).

Step 6. Preparation of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid: Hydrolysis of the carboxylate, ethyl 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetate (0.422 g, 0.554 mmol), was accomplished using the General procedure for the synthesis of carboxylic acid (7). The title compound (0.307 g, 0.418 mmol, 75% yield) was isolated as a white solid. LCMS: m/e 733.4 (MH$^+$), 1.01 min (Method 1). $^1$H NMR (400 MHz, DMSO-d6) δ 9.34 (s, 1H), 8.36-8.21 (m, 1H), 7.84 (d, J=8.1 Hz, 2H), 7.81-7.76 (m, 1H), 7.75-7.69 (m, 1H), 7.37 (s, 5H), 5.55 (s, 1H), 5.44 (dd, J=10.9, 3.4 Hz, 1H), 4.88-4.76 (m, 1H), 4.57 (d, J=9.2 Hz, 1H), 4.44 (d, J=3.5 Hz, 1H), 4.11-3.98 (m, 2H), 3.87 (s, 1H), 3.71-3.51 (m, 1H), 3.47-3.35 (m, 1H), 2.34 (s, 3H).

Dimerization and Deprotection of Benzylidene Acetal, Method 1

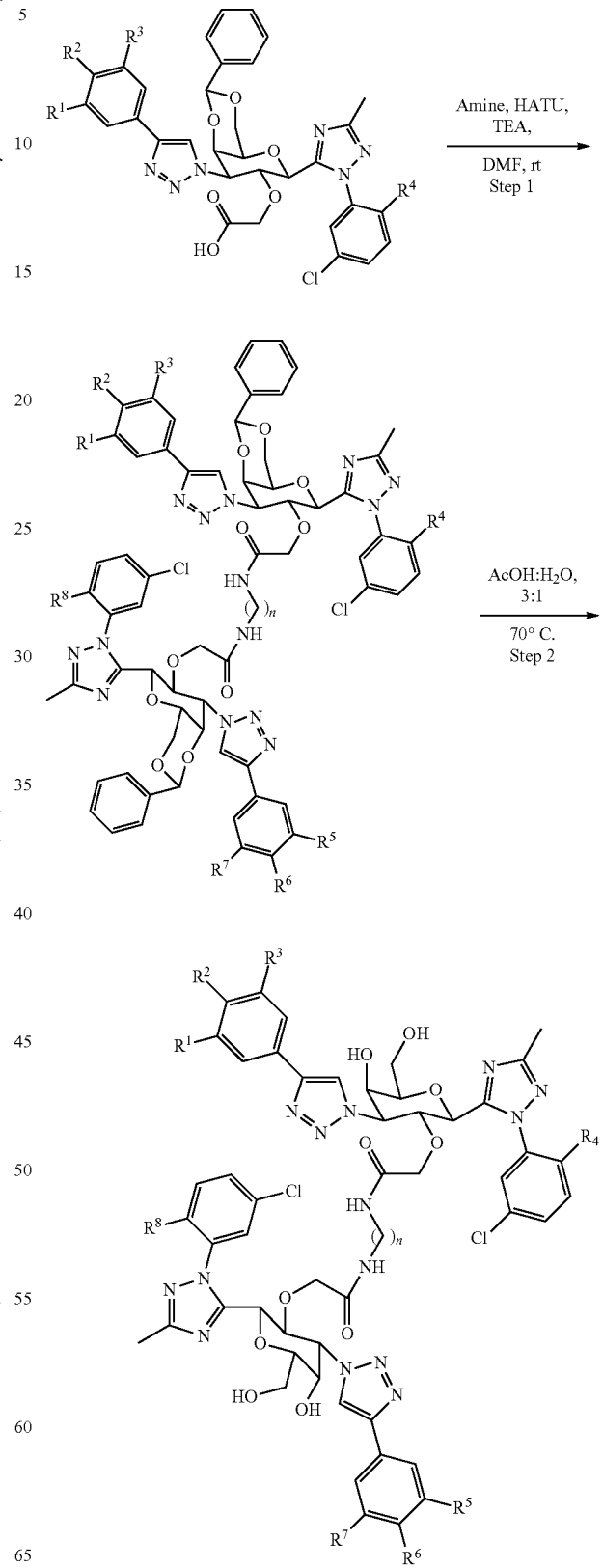

Example 5

Preparation of 2-(((2R,3S,4R,5S,6S)-4-(4-(4-chloro-3-fluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(5-(2-(((2S,3R,4S,5R,6R)-4-(4-(4-chloro-3-fluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)pentyl)acetamide

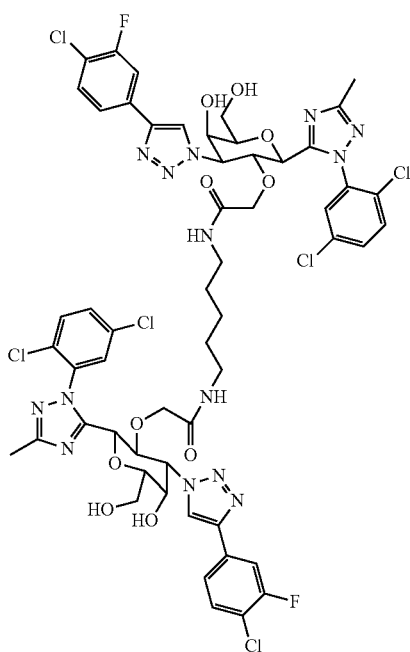 [SMILES: Cc1nc(C2OC(CO)C(O)C(n3cc(-c4ccc(Cl)c(F)c4)nn3)C2OCC(=O)NCCCCCNC(=O)COC2C(c3nc(C)nn3-c3cc(Cl)ccc3Cl)OC(CO)C(O)C2n2cc(-c3ccc(Cl)c(F)c3)nn2)n(-c2cc(Cl)ccc2Cl)n1]

Step 1. Preparation of 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(5-(2-(((2S,6R,7S,8S)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)pentyl)acetamide: To a flask containing a solution of 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (33 mg, 0.046 mmol) in DMF (1 mL) and triethylamine (0.032 mL, 0.230 mmol) was added HATU (52.6 mg, 0.138 mmol) followed by 1,5-diaminopentane (0.032 mL, 0.032 mmol). The mixture was stirred at rt. for 17 h, then was diluted with 2 mL of water and was extracted with dichloromethane (3×2 mL). The organic layers were dried over sodium sulfate, filtered and concentrated under reduced pressure. The residue was purified by preparative HPLC (Method 2). Fractions containing the product were combined and concentrated under reduced pressure. The title compound (21 mg, 0.014 mmol, 61% yield) was isolated as a white solid. LCMS: m/e 1498.0 (MH$^+$), 1.16 min (Method 1).

Step 2. To a solution of 2-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(5-(2-(((2S,6R,7S,8S)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)pentyl)acetamide (21 mg, 0.014 mmol) was added acetic acid (0.5 mL) and water (0.167 mL) and the mixture was heated to 70° C. After 17.5 h, the mixture was cooled to rt and was concentrated under a stream of nitrogen. To the residue was added 0.035 g of potassium carbonate and the mixture was diluted with 0.5 mL of MeOH and 0.25 mL of water and was stirred at rt overnight for 17 h. The mixture was diluted with water (1 mL) and extracted with a mixture of dichloromethane:chloroform:methanol (1:1:0.25, 3×2.25 mL). The combined organic layers were dried over sodium sulfate, filtered and concentrated under reduced pressure. The residue was dissolved in DMF, filtered through a plug of glass wool and was purified by preparative HPLC (Method 2). Fractions containing the product were concentrated under reduced pressure to give the title compound (8.9 mg, 0.0067 mmol, 48% yield). LCMS: m/e 1318.82 (MH$^+$), 1.92 min (Method 2). Key 1H NMR peaks: $^1$H NMR (500 MHz, DMSO-d6) δ 8.83 (s, 2H), 7.90-7.62 (m, 10H), 7.56 (t, J=7.9 Hz, 2H), 6.76-6.57 (m, 2H), 2.29 (s, 6H), 0.91 (quin, J=7.2 Hz, 4H), 0.78-0.66 (m, 2H). IC$_{50}$=0.01 uM.

Example 6

Preparation of 2-(((2R,3S,4R,5S,6S)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(3-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)propyl)acetamide

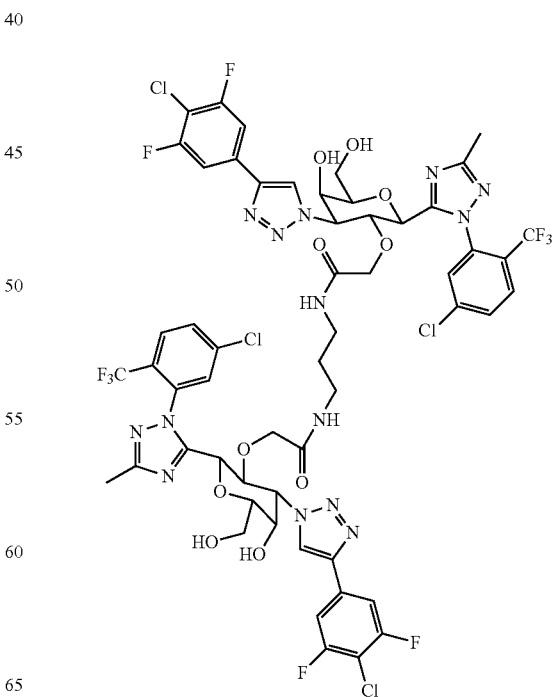

Step 1. Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(3-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)propyl)acetamide: To a flask containing a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (0.035 g, 0.046 mmol) in DMF (1 mL) and triethylamine (0.032 mL, 0.228 mmol) was added 1,3-diaminopropane (1M in DMF) (0.023 mL, 0.023 mmol) followed by HATU (0.052 g, 0.137 mmol). The mixture was stirred at rt for 43 h, then was diluted with 2 mL of water and was extracted with dichloromethane (3×2 mL). The organic layers were dried over sodium sulfate, filtered and concentrated under reduced pressure. The residue was dissolved in DMF, filtered through a plug of glass wool and was purified by preparative HPLC (Method 2). Fractions containing the product were concentrated under reduced pressure. The title compound (25 mg, 0.016 mmol, 70% yield) was isolated as a white film. LCMS: m/e 1573.6 (MH$^+$), 1.19 min (Method 1).

Step 2. To a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(3-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)propyl)acetamide (25 mg, 0.016 mmol) was added acetic acid (0.5 mL) and water (0.167 mL) and the mixture was heated to 70° C. After heating the mixture for 17.5 h, it was cooled to rt and concentrated under a stream of nitrogen. To the residue was added 0.035 g of potassium carbonate and the mixture was diluted with 0.5 mL of MeOH and 0.25 mL of water and was stirred at rt overnight for 17 h. The mixture was diluted with water (1 mL) and extracted with a mixture of dichloromethane:chloroform:methanol (1:1:0.25, 3×2.25 mL). The combined organic layers were dried over sodium sulfate, filtered and concentrated under reduced pressure. The residue was dissolved in DMF, filtered through a plug of glass wool and purified by preparative HPLC (Method 3). Fractions containing the product were concentrated under reduced pressure to give the title compound (13.0 mg, 0.0093 mmol, 59% yield). LCMS: m/e 1396.8 (MH$^+$), 2.03 min (Method 2). Key $^1$H NMR peaks: $^1$H NMR (500 MHz, DMSO-d6) δ 8.93 (s, 2H), 7.98-7.65 (m, 10H), 6.99-6.74 (m, 2H), 2.24 (s, 6H), 1.06-0.90 (m, 2H). IC$_{50}$=0.001 uM.

Example 7

Preparation of 2-(((2R,3S,4R,5S,6S)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(4-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)butyl)acetamide

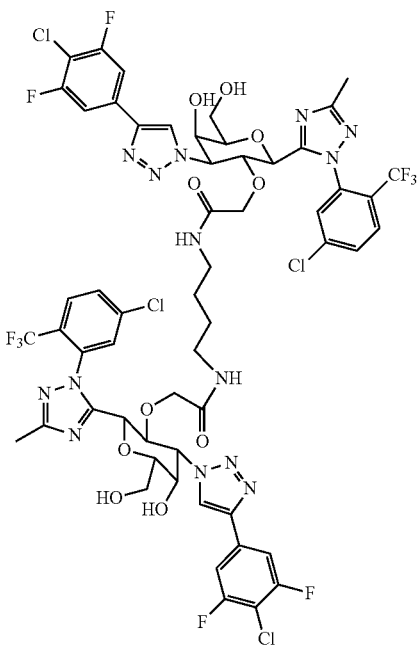 [SMILES: Cc1nc(C2OC(CO)C(O)C(n3cc(-c4cc(F)c(Cl)c(F)c4)nn3)C2OCC(=O)NCCCCNC(=O)COC2C(c3nc(C)nn3-c3cc(Cl)ccc3C(F)(F)F)OC(CO)C(O)C2n2cc(-c3cc(F)c(Cl)c(F)c3)nn2)n(-c2cc(Cl)ccc2C(F)(F)F)n1]

Step 1. Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(4-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)butyl)acetamide: To a flask containing a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (0.026 g, 0.034 mmol) in DMF (1 mL) and triethylamine (0.024 mL, 0.169 mmol) was added 1,4-diaminobutane (1M in DMF) (0.017 mL, 0.017 mmol) followed by HATU (0.039 g, 0.102 mmol). The mixture was stirred at rt for 43 h then was diluted with 2 mL of water and was extracted with dichloromethane (3×2 mL). The organic layers were dried over sodium sulfate, filtered and concentrated under reduced pressure. The residue was purified by preparative HPLC (Method 2). Fractions containing the product were concentrated under reduced pressure. The title compound (24 mg, 0.015 mmol, 88% yield) was isolated as an off-white solid. LCMS: m/e 1573.6 (MH$^+$), 1.19 min (Method 1).

Step 2. To a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(4-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)butyl)acetamide (24 mg, 0.015 mmol) was added acetic acid (0.5 mL) and water (0.167 mL) and the mixture was heated to 70° C. After 17.5 h of heating, the mixture was cooled to rt and concentrated under a stream of nitrogen. To the residue was added 0.035 g of potassium carbonate and the mixture was diluted with 0.5 mL of MeOH and 0.25 mL of water. The mixture was stirred for 5 h at rt, then was diluted with water (1 mL) and extracted with dichloromethane (3×1 mL). The combined organic layers were dried over sodium sulfate, filtered and concentrated under reduced pressure. The residue was dissolved in DMF and purified by preparative HPLC (Method 4). Fractions containing the product were concentrated under reduced pressure to give the title product (13.0 mg, 0.0092 mmol, 61% yield). LCMS: m/e 1409.19 (MH$^+$), 1.97 min (Method 2). Key 1H NMR peaks: $^1$H NMR (500 MHz, DMSO-d6) δ 9.02 (s, 2H), 7.99-7.94 (m, 2H), 7.92-7.84 (m, 4H), 7.77 (d, J=8.2 Hz, 4H), 6.72-6.54 (m, 2H), 2.27 (s, 6H), 0.90 (br s, 4H). IC$_{50}$=0.001 uM.

Example 8

Preparation of 2-(((2R,3S,4R,5S,6S)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(5-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)pentyl)acetamide

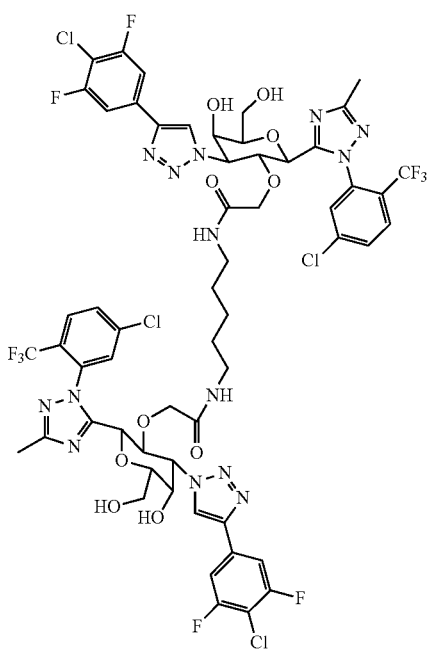 [SMILES: Cc1nc(C2OC(CO)C(O)C(n3cc(-c4cc(F)c(Cl)c(F)c4)nn3)C2OCC(=O)NCCCCCNC(=O)COC2C(c3nc(C)nn3-c3cc(Cl)ccc3C(F)(F)F)OC(CO)C(O)C2n2cc(-c3cc(F)c(Cl)c(F)c3)nn2)n(-c2cc(Cl)ccc2C(F)(F)F)n1]

Step 1. Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(5-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)pentyl)acetamide: To a flask containing a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (37 mg, 0.048 mmol) in DMF (1 mL) and triethylamine (0.034 mL, 0.241 mmol) was added 1,5-diaminopentane (0.024 mL, 0.024 mmol) followed by HATU (55.0 mg, 0.145 mmol). The mixture was stirred at rt for 43 h, then was diluted with 2 mL of water and was extracted with dichloromethane (3×2 mL). The organic layers were dried over sodium sulfate, filtered and concentrated under reduced pressure. The residue was dissolved in DMF and was purified by preparative HPLC (Method 2). Fractions containing the product were combined and concentrated under reduced pressure. The title compound (29 mg, 0.018 mmol, 75% yield) was isolated as a white solid. LCMS: m/e 1602.2 (MH$^+$), 1.19 min (Method 1).

Step 2. To a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(5-(2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)pentyl)acetamide (29 mg, 0.018 mmol) was added acetic acid (0.5 mL) and water (0.167 mL) and the mixture was heated to 70° C. After 17.5 h of heating, the mixture was cooled to rt and concentrated under a stream of nitrogen. To the residue was added 0.035 g of potassium carbonate and the mixture was diluted with 0.5 mL of MeOH and 0.25 mL of water and was stirred at rt for 5 h. The mixture was diluted with water (1 mL) and extracted with dichloromethane (3×1 mL). The combined organic layers were dried over sodium sulfate, filtered and concentrated under reduced pressure. The residue was dissolved in DMF, filtered through a plug of glass wool and was purified by preparative HPLC (Method 5). Fractions containing the product were concentrated under reduced pressure to give the title product (15.3 mg, 0.011 mmol, 61% yield). LCMS: m/e 1423.11 (MH$^+$), 2.08 min (Method 2). Key 1H NMR peaks: $^1$H NMR (500 MHz, DMSO-d6) δ 8.94 (s, 2H), 7.95 (d, J=8.9 Hz, 2H), 7.91-7.80 (m, 4H), 7.72 (d, J=8.2 Hz, 4H), 6.73-6.51 (m, 2H), 2.28 (s, 6H), 0.93 (quin, J=7.2 Hz, 4H), 0.74 (quin, J=7.1 Hz, 2H). IC$_{50}$=0.001 uM.

Example 9

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(6-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)hexyl)acetamide

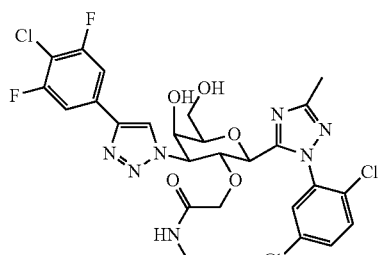
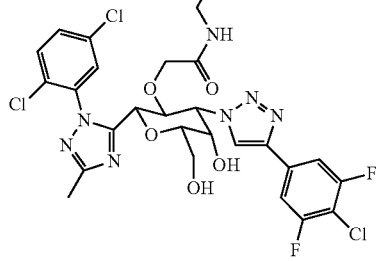

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(6-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)hexyl)acetamide: To a flask containing a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy) acetic acid (0.04 g, 0.055 mmol) in DMF (1 mL) and triethylamine (0.038 mL, 0.273 mmol) was added hexane-1,6-diamine (1M in DMF) (0.027 mL, 0.027 mmol) followed by HATU (0.062 g, 0.164 mmol). The mixture was stirred at rt for 64 h, then was diluted with 2 mL of water and was extracted with dichloromethane (3×2 mL). The organic layers were dried over sodium sulfate, filtered and concentrated under reduced pressure. The residue was purified by preparative HPLC (Method 9). Fractions containing the product were combined and concentrated under reduced pressure to give the title product (0.027 g, 0.017 mmol, 62% yield) as a white solid. LCMS: m/e 1546.0 (MH+), 1.19 min (Method 1).

Step 2. To a solution of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(6-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)hexyl)acetamide (27 mg, 0.017 mmol) in acetic acid (0.5 mL) was added water (0.167 mL) and the mixture was heated to 70° C. After 19 h of heating, the mixture was cooled to rt and was concentrated under a stream of nitrogen. To the residue was added 0.035 g of K$_2$CO$_3$ and the mixture was diluted with 0.5 mL of MeOH and 0.25 mL of water. After stirring the mixture for 20 h, the mixture was diluted with water (1 mL) and extracted with dichloromethane (2×1 mL) then with chloroform:MeOH (4:1, 2 mL). The combined organic layers were dried over sodium sulfate, filtered and concentrated under reduced pressure. The residue was dissolved in DMF, filtered through a plug of glass wool and was purified by preparative HPLC (Method 10). Fractions containing the product were concentrated under reduced pressure to give the title product (10.1 mg, 0.0074 mmol, 43% yield). LCMS: m/e 1369.96 (MH+), 2.06 min (Method 2). $^1$H NMR (500 MHz, DMSO-d6) δ 8.98 (s, 2H), 7.84-7.61 (m, 10H), 6.62 (br d, J=4.9 Hz, 2H), 5.46 (d, J=6.1 Hz, 2H), 5.12 (dd, J=11.0, 2.4 Hz, 2H), 4.80-4.63 (m, 4H), 4.42 (br d, J=9.5 Hz, 2H), 3.90 (br d, J=2.7 Hz, 2H), 3.78-2.58 (m, 10H), 2.30 (s, 6H), 0.96 (br s, 4H), 0.79 (br s, 4H). IC$_{50}$=0.006 uM.

Example 10

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(7-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)heptyl)acetamide

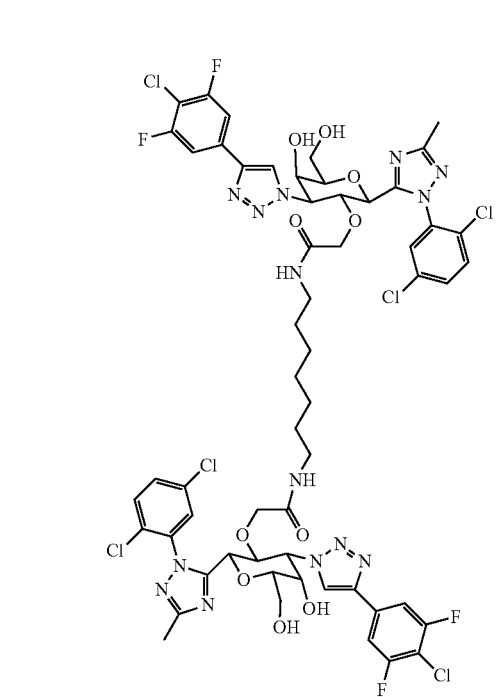 [SMILES: Cc1nc(C2OC(CO)C(O)C(n3cc(-c4cc(F)c(Cl)c(F)c4)nn3)C2OCC(=O)NCCCCCCCNC(=O)COC2C(c3nc(C)nn3-c3cc(Cl)ccc3Cl)OC(CO)C(O)C2n2cc(-c3cc(F)c(Cl)c(F)c3)nn2)n(-c2cc(Cl)ccc2Cl)n1]

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(7-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)heptyl)acetamide: To a flask containing a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy) acetic acid (0.04 g, 0.055 mmol) in DMF (2 mL) and triethylamine (0.038 mL, 0.273 mmol) was added heptane-1,7-diamine (1M in DMF) (0.027 mL, 0.027 mmol) followed by HATU (0.062 g, 0.164 mmol). The mixture was stirred at rt for 64 h, then was diluted with 2 mL of water and was extracted with dichloromethane (3×2 mL). The organic layers were dried over sodium sulfate, filtered and concentrated under reduced pressure. The residue was purified by preparative HPLC (Method 9). Fractions containing the product were combined and concentrated under reduced pressure to give the title product (0.027 g, 0.017 mmol, 62% yield) as a white solid. LCMS: m/e 1559.9 (MH$^+$), 1.20 min (Method 1).

Step 2: To a solution of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(7-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)heptyl)acetamide (27 mg, 0.017 mmol) in acetic acid (0.5 mL) was added water (0.167 mL) and the mixture was heated to 70° C. After 19 h, the mixture was cooled to rt and was concentrated under a stream of nitrogen. To the residue was added 0.035 g of $K_2CO_3$ and the mixture was diluted with 0.5 mL of MeOH and 0.25 mL of water. The mixture was stirred at rt for 20 h, then was diluted with water (1 mL) and extracted with dichloromethane (2×1 mL) then with chloroform:MeOH (4:1, 2 mL). The combined organic layers were dried over sodium sulfate, filtered and concentrated under reduced pressure. The residue was dissolved in DMF, filtered through a plug of glass wool and was purified by preparative HPLC (Method 11). The fractions containing the product were concentrated under reduced pressure to give the title product (16.2 mg, 0.0117 mmol, 69% yield). LCMS: m/e 1382.89 (MH$^+$), 2.14 min (Method 2). $^1$H NMR (500 MHz, DMSO-d6) δ 8.98 (s, 2H), 7.83-7.60 (m, 10H), 6.61 (br d, J=3.7 Hz, 2H), 5.46 (d, J=6.1 Hz, 2H), 5.12 (dd, J=10.7, 2.7 Hz, 2H), 4.83-4.63 (m, 4H), 4.42 (d, J=9.5 Hz, 2H), 3.91 (dd, J=5.5, 2.7 Hz, 2H), 3.75-2.59 (m, 10H), 2.30 (s, 6H), 0.98 (br s, 4H), 0.83 (br s, 6H). $IC_{50}$=0.01 uM.

Example 11

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(5-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)pentyl)acetamide

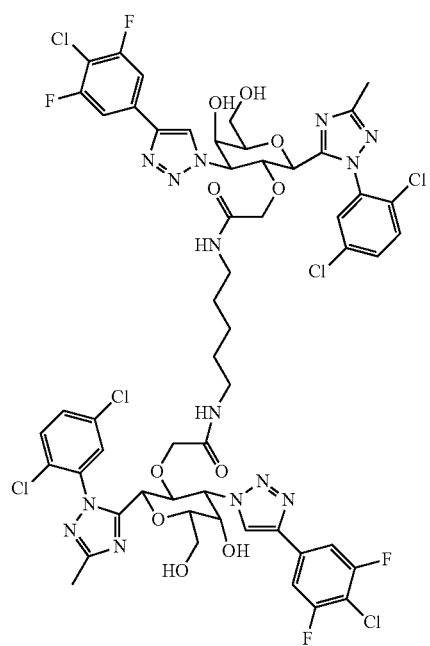 [SMILES: Cc1nc(C2OC(CO)C(O)C(n3cc(-c4cc(F)c(Cl)c(F)c4)nn3)C2OCC(=O)NCCCCCNC(=O)COC2C(c3nc(C)nn3-c3cc(Cl)ccc3Cl)OC(CO)C(O)C2n2cc(-c3cc(F)c(Cl)c(F)c3)nn2)n(-c2cc(Cl)ccc2Cl)n1]

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(5-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)pentyl)acetamide:
To a flask containing a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (0.04 g, 0.055 mmol) in DMF (1 mL) and triethylamine (0.038 mL, 0.273 mmol) was added 1,5-diaminopentane (1M in DMF) (0.027 mL, 0.027 mmol) followed by HATU (0.062 g, 0.164 mmol). The mixture was stirred at rt for 64 h, then was diluted with 2 mL of water and was extracted with dichloromethane (3×2 mL). The organic layers were dried over sodium sulfate, filtered and concentrated under reduced pressure. The residue was purified by preparative HPLC (Method 9). Fractions containing the product were combined and concentrated under reduced pressure to give the title product (0.024 g, 0.0156 mmol, 57% yield) as a white solid. LCMS: m/e 1535.3 (MH$^+$), 1.27 min (Method 1).

Step 2. To a solution of 2-(((2R,4aS,6R,7S,8S,8aS)-8-(4-(4-chloro-3,5-difluorophenyl)-1H-1,2,3-triazol-1-yl)-6-(1-

(2,5-dichlorophenyl)-3-methyl-1H-1,2,4-triazol-5-yl)-2-phenylhexahydropyrano[3,2-d][1,3]dioxin-7-yl)oxy)-N-(5-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)pentyl)acetamide (24 mg, 0.016 mmol) in acetic acid (0.5 mL) and water (0.167 mL) and the mixture was heated to 70° C. After heating the mixture for 67 h, it was cooled to rt and concentrated under a stream of nitrogen. To the residue was added 0.035 g of $K_2CO_3$ and the mixture was diluted with 0.5 mL of MeOH and 0.25 mL of water. The mixture was stirred at rt for 66 h then was diluted with water (1 mL) and extracted with dichloromethane (3×1 mL). The combined organic layers were dried over sodium sulfate, filtered and concentrated under reduced pressure. The residue was diluted with DMF, filtered through a plug of glass wool and was purified by preparative HPLC (Method 12). Fractions containing the product were combined and concentrated under reduced pressure to give the title product (6.5 mg, 0.0048 mmol, 30% yield). LCMS: m/e 1357.9 (MH$^+$), 1.96 min (Method 2). Key $^1$H NMR peaks: $^1$H NMR (500 MHz, DMSO-d6) δ 9.01-8.93 (m, 2H), 7.81-7.62 (m, 10H), 6.76-6.58 (m, 2H), 2.29 (s, 6H), 0.99-0.87 (m, 4H), 0.80-0.69 (m, 2H). $IC_{50}$=0.001 uM.

Example 12

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(4-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)butyl)acetamide

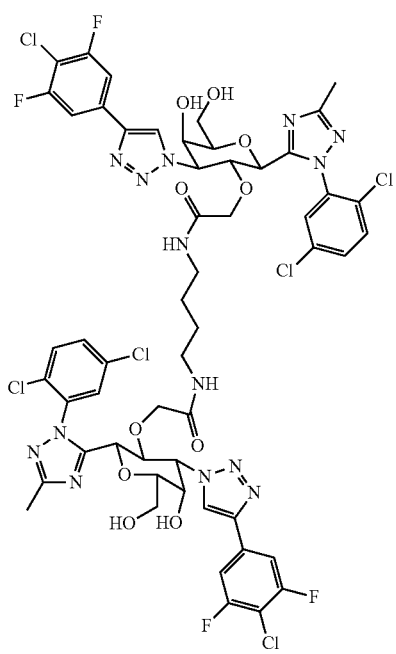 [SMILES: Cc1nc(C2OC(CO)C(O)C(n3cc(-c4cc(F)c(Cl)c(F)c4)nn3)C2OCC(=O)NCCCCNC(=O)COC2C(c3nc(C)nn3-c3cc(Cl)ccc3Cl)OC(CO)C(O)C2n2cc(-c3cc(F)c(Cl)c(F)c3)nn2)n(-c2cc(Cl)ccc2Cl)n1]

Step 1. Preparation of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(4-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)butyl)acetamide: To a flask containing a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (40 mg, 0.055 mmol) in DMF (1 mL) and triethylamine (0.038 mL, 0.273 mmol) was added butane-1,4-diamine (1M in DMF) (0.027 mL, 0.027 mmol) followed by HATU (62.2 mg, 0.164 mmol). The mixture was stirred at rt for 64 h, then was diluted with 2 mL of water and was extracted with dichloromethane (3×2 mL). The organic layers were dried over sodium sulfate, filtered and concentrated under reduced pressure. The residue was purified by flash chromatography using a 0-100% MeOH in dichloromethane gradient and a 24 g silica gel column. Fractions containing the product were combined and concentrated under reduced pressure to give the product (0.022 g, 0.0145, 53% yield) as an off-white solid. LCMS: m/e 1520.1 (MH$^+$), 1.18 min (Method 1).

Step 2. To a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(4-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)butyl)acetamide (22 mg, 0.014 mmol) in acetic acid (0.5 mL) was added water (0.167 mL) and the mixture was heated to 70° C. After 21 h of heating, the mixture was cooled to rt and was concentrated under a stream of nitrogen. To the residue was added 0.035 g of $K_2CO_3$ and the mixture was diluted with 0.5 mL of MeOH and 0.25 mL of water. The mixture was stirred at rt for 20 h, then was diluted with water (1 mL) and extracted with dichloromethane (3×1 mL). The combined organic layers were dried over sodium sulfate, filtered and concentrated under reduced pressure. The residue was dissolved in DMF, filtered through a plug of glass wool and was purified by preparative HPLC (Method 13). Fractions containing the product were combined and concentrated under reduced pressure to give the title product (9.8 mg, 0.0073 mmol, 52% yield). LCMS: m/e 1341.8 (MH$^+$), 1.94 min (Method 2). Key $^1$H NMR peaks: $^1$H NMR (500 MHz, DMSO-d6) δ 9.03-8.88 (m, 2H), 7.81-7.61 (m, 10H), 6.86-6.60 (m, 2H), 2.27 (s, 6H), 0.87 (br s, 4H). $IC_{50}$=0.001 uM.

Example 13

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(2-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetamido)ethyl)acetamide

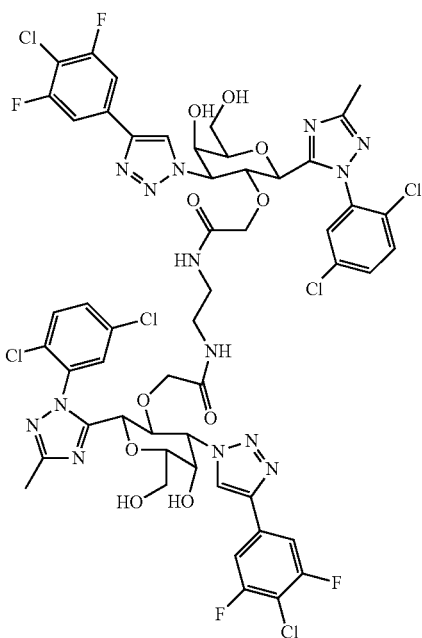 [SMILES: Cc1nc(C2OC(CO)C(O)C(n3cc(-c4cc(F)c(Cl)c(F)c4)nn3)C2OCC(=O)NCCNC(=O)COC2C(c3nc(C)nn3-c3cc(Cl)ccc3Cl)OC(CO)C(O)C2n2cc(-c3cc(F)c(Cl)c(F)c3)nn2)n(-c2cc(Cl)ccc2Cl)n1]

Step 1. Preparation of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(2-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)ethyl)acetamide: To a flask containing a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (40 mg, 0.055 mmol) in DMF (1 mL) and triethylamine (0.038 mL, 0.273 mmol) was added ethane-1,2-diamine (1M in DMF) (0.027 mL, 0.027 mmol) followed by HATU (62.2 mg, 0.164 mmol). The mixture was stirred at rt for 40 h, then the mixture was diluted with 2 mL of water and was extracted with dichloromethane (3×2 mL). The organic layers were dried over sodium sulfate, filtered and concentrated under reduced pressure. The residue was purified by preparative HPLC (Method 9). Fractions containing the product were combined and concentrated under reduced pressure to give the title product (0.023 g, 0.0154 mmol, 56% yield) as a white solid. LCMS: m/e 1489.9 (MH+), 1.19 min (Method 1).

Step 2. To a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(2-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)ethyl)acetamide (0.023 g, 0.015 mmol) in acetic acid (0.5 mL) was added water (0.167 mL) and the mixture was heated to 70° C. After heating the mixture for 30 h, the mixture was cooled to rt and was concentrated under a stream of nitrogen. To the residue was added 0.035 g of $K_2CO_3$ and the mixture was diluted with 0.5 mL of MeOH and 0.25 mL of water. The mixture was stirred at rt for 3 days, then was diluted with water (1 mL) and extracted with dichloromethane (3×1 mL). The combined organic layers were dried over sodium sulfate, filtered and concentrated under reduced pressure. The residue was dissolved in DMF, filtered through a plug of glass wool and was purified by preparative HPLC (Method 14). The fractions containing the product were combined and concentrated under reduced pressure to give the title product (6.8 mg, 0.0052, 35% yield). LCMS: m/e 1316.1 (MH+), 1.93 min (Method 2). Key $^1$H NMR peaks: $^1$H NMR (500 MHz, DMSO-d6) δ 8.94 (dd, J=5.4, 2.5 Hz, 2H), 7.79-7.58 (m, 10H), 7.01 (br d, J=1.3 Hz, 2H), 2.26 (s, 6H). $IC_{50}$=0.001 uM.

Example 14

Preparation of 2-(((2R,3S,4R,5S,6S)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(4-((2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)methyl)benzyl)acetamide

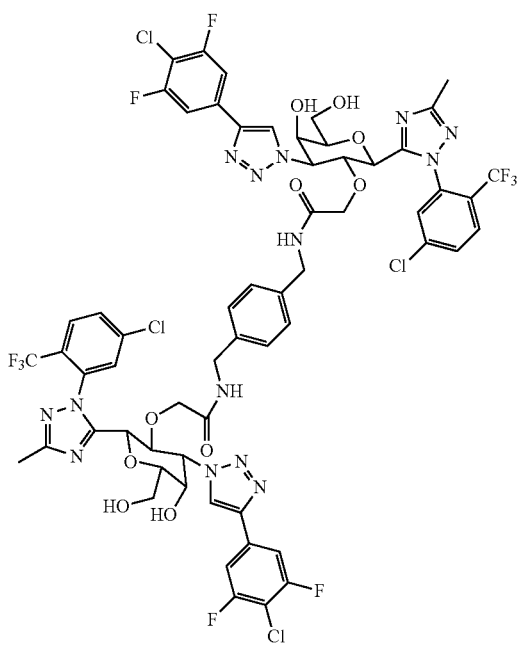 [SMILES: Cc1nc(C2OC(CO)C(O)C(n3cc(-c4cc(F)c(Cl)c(F)c4)nn3)C2OCC(=O)NCc2ccc(CNC(=O)COC3C(c4nc(C)nn4-c4cc(Cl)ccc4C(F)(F)F)OC(CO)C(O)C3n3cc(-c4cc(F)c(Cl)c(F)c4)nn3)cc2)n(-c2cc(Cl)ccc2C(F)(F)F)n1]

Step 1. Preparation of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(4-((2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)methyl)benzyl)acetamide: To a flask containing a solution of 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (0.021 g, 0.027 mmol) in DMF (1 mL) and triethylamine (0.019 mL, 0.137 mmol) was added HATU (0.031 g, 0.082 mmol) followed by p-xylylenediamine (1M in DMF) (0.027 mL, 0.014 mmol). The mixture was stirred at rt for 17.5 h, then was diluted with 2 mL of water and was extracted with dichloromethane (3×2 mL). The organic layers were dried over sodium sulfate, filtered and concentrated under reduced pressure. The residue was dissolved in DMF and purified by preparative HPLC (method 25). Fractions containing the product were combined and concentrated under reduced pressure to give the title product (0.005 g, 0.0031 mmol, 23% yield) as a white solid. LCMS: m/e 1635.9 (MH+), 1.19 min (Method 1).

Step 2. To a flask containing crude 2-(((2S,4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(4-((2-(((2S,6R,7S,8S)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)methyl)benzyl)acetamide (5 mg, 3.1 µmol) was added acetic acid (0.5 mL) and water (0.167 mL). The mixture was heated to 70° C. for 16 h, then mixture was cooled to rt and was concentrated under reduced pressure. To the mixture was added 35 mg of potassium carbonate and it was diluted with 0.5 mL of methanol and 0.25 mL of water then was stirred at rt for 4 h. The mixture was diluted with water (2 mL) and extracted with dichloromethane (3×3 mL). The organic layers were dried over sodium sulfate, filtered and concentrated under reduced pressure. The residue was dissolved in DMF and was purified by preparative HPLC. Fractions containing the product were concentrated under reduced pressure to give the title product (1.3 mg, 0.891 µmol, 29% yield). LCMS: m/e 1457.12 (MH+), 2.21 min (Method 2). Key $^1$H NMR peaks: $^1$H NMR (500 MHz, DMSO-d6) δ 9.06 (s, 2H), 7.97 (d, J=8.2 Hz, 2H), 7.92-7.86 (m, 4H), 7.79 (br d, J=8.2 Hz, 4H), 7.35-7.19 (m, 2H), 6.79 (s, 4H), 2.25 (s, 6H).

Example 15

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(4-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-methylacetamido)butyl)-N-methylacetamide

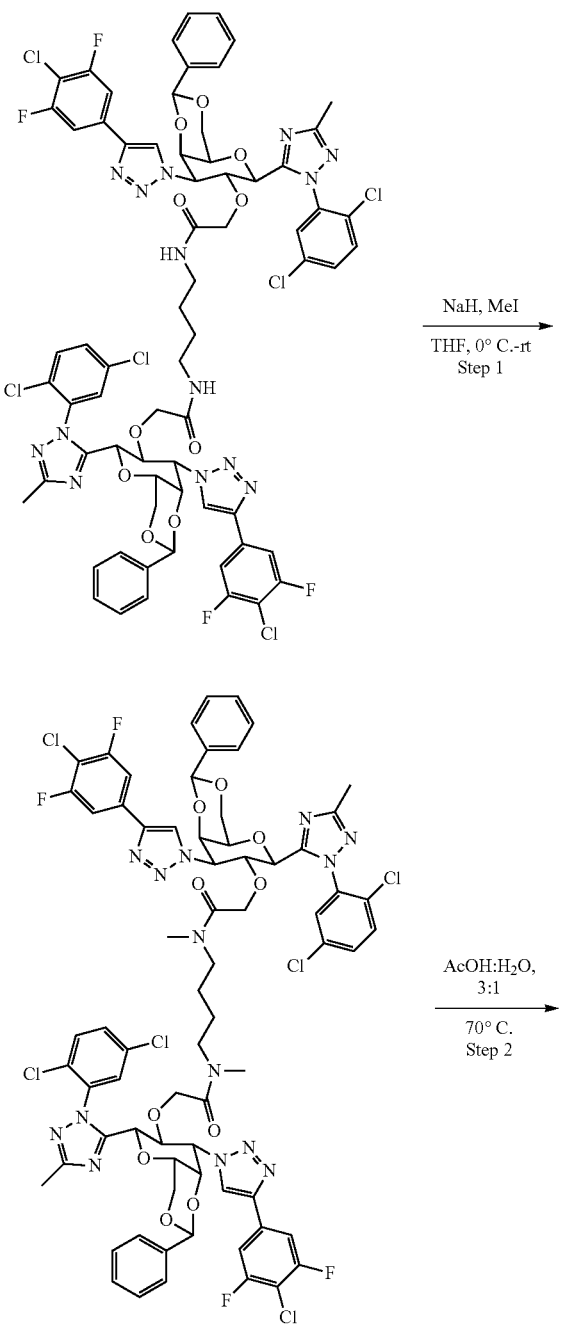

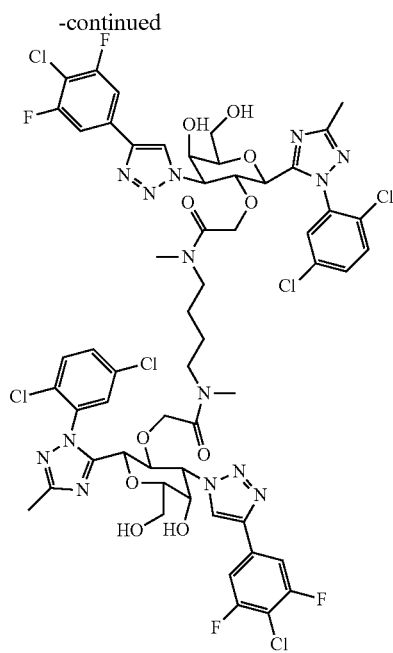

Step 1. Preparation of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(4-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-methylacetamido)butyl)-N-methylacetamide: A solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(4-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetamido)butyl)acetamide (0.03 g, 0.020 mmol) in THF (2 mL) was cooled to 0° C. and sodium hydride (60% dispersion) (4.74 mg, 0.118 mmol) was added. The mixture was stirred for 15 minutes and methyl iodide (4.94 µl, 0.079 mmol) was added. The mixture was warmed to rt as the ice bath melted and warmed. After 15 h of stirring, the mixture was carefully diluted with water (5 mL) and was extracted with ethyl acetate (3×5 mL). The organic layers were washed with brine, dried over magnesium sulfate, filtered and concentrated under reduced pressure. The residue was dissolve in DMF and purified by preparative HPLC (Method 15). Fractions containing the product were concentrated under reduced pressure to give the title product (0.012 g, 0.0078 mmol, 39% yield) as a clear film. LCMS: m/e 1550.3 (MH$^+$), 1.20 min (Method 1).

Step 2. To a solution of 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(4-(2-(((2S,6R,7S,8S)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-methylacetamido)butyl)-N-methylacetamide (0.012 g, 7.8 µmol) in acetic acid (0.5 mL) was added water (0.167 mL) and the mixture was heated to 70° C. After heating the mixture for 17 h, it was cooled to rt concentrated under a stream of nitrogen. To the residue was added 0.035 g of $K_2CO_3$ and the mixture was diluted with 0.5 mL of MeOH and 0.25 mL of $H_2O$. The mixture was stirred at rt for 4 h, then was concentrated under a stream of nitrogen, diluted with water (1 mL) and extracted with dichloromethane (3×1 mL). The combined organic layers were dried over sodium sulfate, filtered and concentrated under reduced pressure. The residue was dissolved in DMF and purified by preparative HPLC (Method 11). Fractions containing the product were concentrated under reduced pressure to give the title compound (0.0045 g, 0.0033 mmol, 42% yield). LCMS: m/e 1368.98 (MH$^+$), 2.14 min (Method 2). $^1$H NMR (500 MHz, DMSO-d6) δ 9.10 (s, 2H), 8.01 (d, J=8.2 Hz, 2H), 7.96-7.89 (m, 4H), 7.83 (br d, J=8.2 Hz, 4H), 7.40-7.21 (m, 2H), 6.83 (s, 4H), 5.50 (br d, J=6.1 Hz, 1H), 5.19-5.10 (m, 2H), 4.84 (br t, J=9.2 Hz, 2H), 4.69 (br s, 1H), 4.50 (br d, J=9.2 Hz, 2H), 4.07-3.17 (m, 14H), 2.29 (s, 6H). $IC_{50}$=0.005 uM.

Example 16

Preparation of (2R,3R,4S,5R,6S)-4-(4-(4-chloro-3-fluorophenyl)-1H-1,2,3-triazol-1-yl)-5-((10-(((2R,3S,4R,5S,6S)-4-(4-(4-chloro-3-fluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)decyl)oxy)-6-(1-(2,5-dichlorophenyl)-3-methyl-1H-1,2,4-triazol-5-yl)-2-(hydroxymethyl)tetrahydro-2H-pyran-3-ol

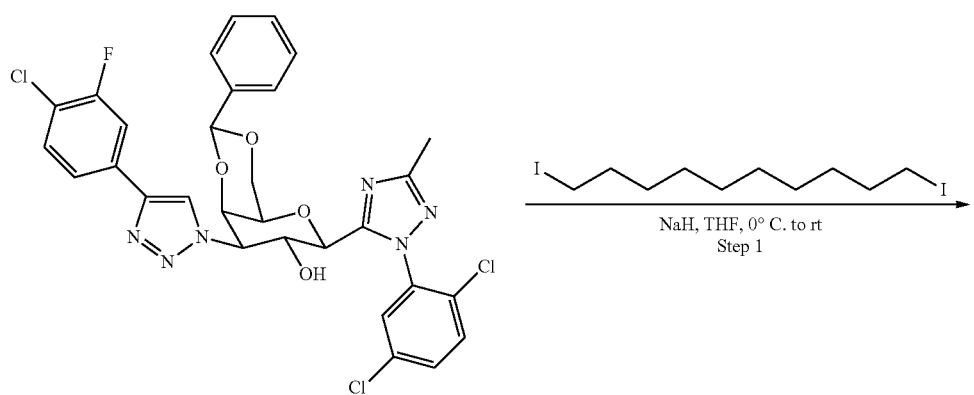

-continued

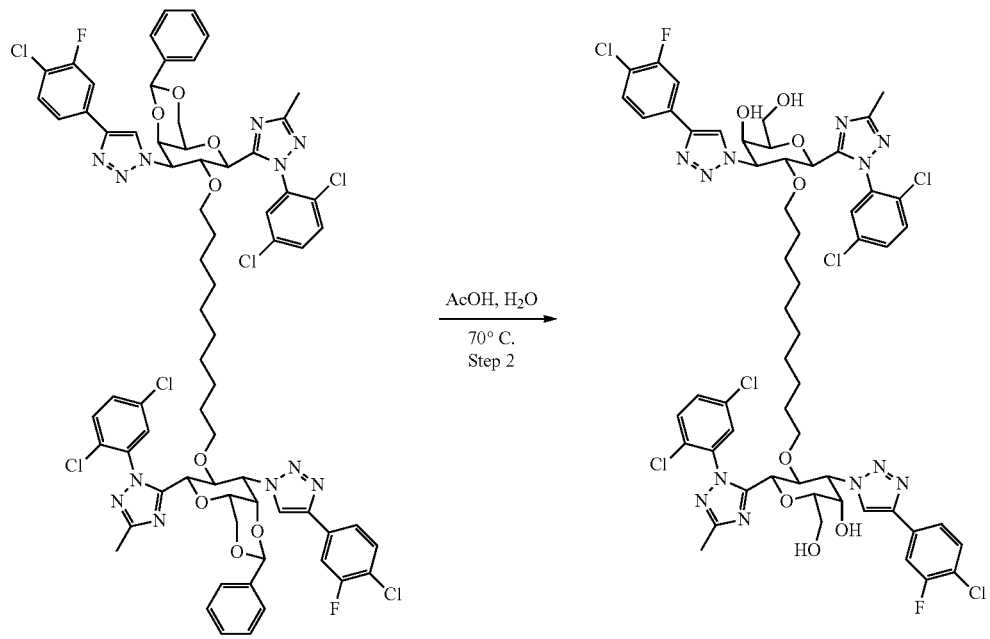

Step 1. Preparation of 1-(((2R,4aS,6R,7S,8S,8aS)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-10-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)decane: A solution of (2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (43 mg, 0.065 mmol) in THF (2 mL) was cooled to 0° C. and a sodium hydride (60% mineral oil dispersion) (13.07 mg, 0.327 mmol) was added. The mixture was stirred for 15 minutes and a solution of 1,10-diiododecane (1M in THF) (0.033 mL, 0.033 mmol) was added. The mixture was stirred at 0° C. and was allowed to warm to rt as the ice bath melted and warmed. After stirring the mixture for 6 days, the mixture was carefully diluted with water (10 mL) and was extracted with dichloromethane (3×10 mL). The organic layers were dried over sodium sulfate, filtered and concentrated under reduced pressure. The crude product (37 mg, 0.025 mmol, 77% yield) was used in the next step with no additional purification. LCMS: m/e 1453.9 (MH$^+$), 1.31 min (Method 1).

Step 2. To a vial containing the crude 1-(((2R,4aS,6R,7S,8S,8aS)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-10-(((2S,4aR,6S,7R,8R,8aR)-8-(4-(4-chloro-3-fluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)decane (37 mg, 0.025 mmol) was added acetic acid (0.5 mL) and water (0.167 mL). The mixture was heated to 70° C. for then was concentrated under a stream of nitrogen. To the residue was added 35 mg of potassium carbonate and the mixture was diluted with 0.5 mL of methanol and 0.25 mL of water then was stirred at rt for 2 h. The mixture was diluted with water (1 mL) and extracted with dichloromethane (3×1 mL). The combined organic layers were dried over sodium sulfate, filtered and concentrated under reduced pressure. The residue was dissolved in DMF and was purified by preparative HPLC (Method 18). Fractions containing the product were concentrated under reduced pressure to give the title compound. LCMS: m/e 1277.0 (MH$^+$), 2.65 min (Method 2). Key $^1$H NMR peaks. $^1$H NMR (500 MHz, DMSO-d6) δ 8.91 (br s, 2H), 7.86 (br d, J=10.4 Hz, 2H), 7.79-7.48 (m, 10H), 2.30 (s, 6H), 0.81 (br d, J=5.0 Hz, 4H), 0.65-0.41 (m, 12H). IC$_{50}$=10 uM.

Example 17

Preparation of (2R,3R,4S,5R,6S)-4-(4-(4-chloro-3,5-difluorophenyl)-1H-1,2,3-triazol-1-yl)-5-((8-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)octyl)oxy)-6-(1-(2,5-dichlorophenyl)-3-methyl-1H-1,2,4-triazol-5-yl)-2-(hydroxymethyl)tetrahydro-2H-pyran-3-ol

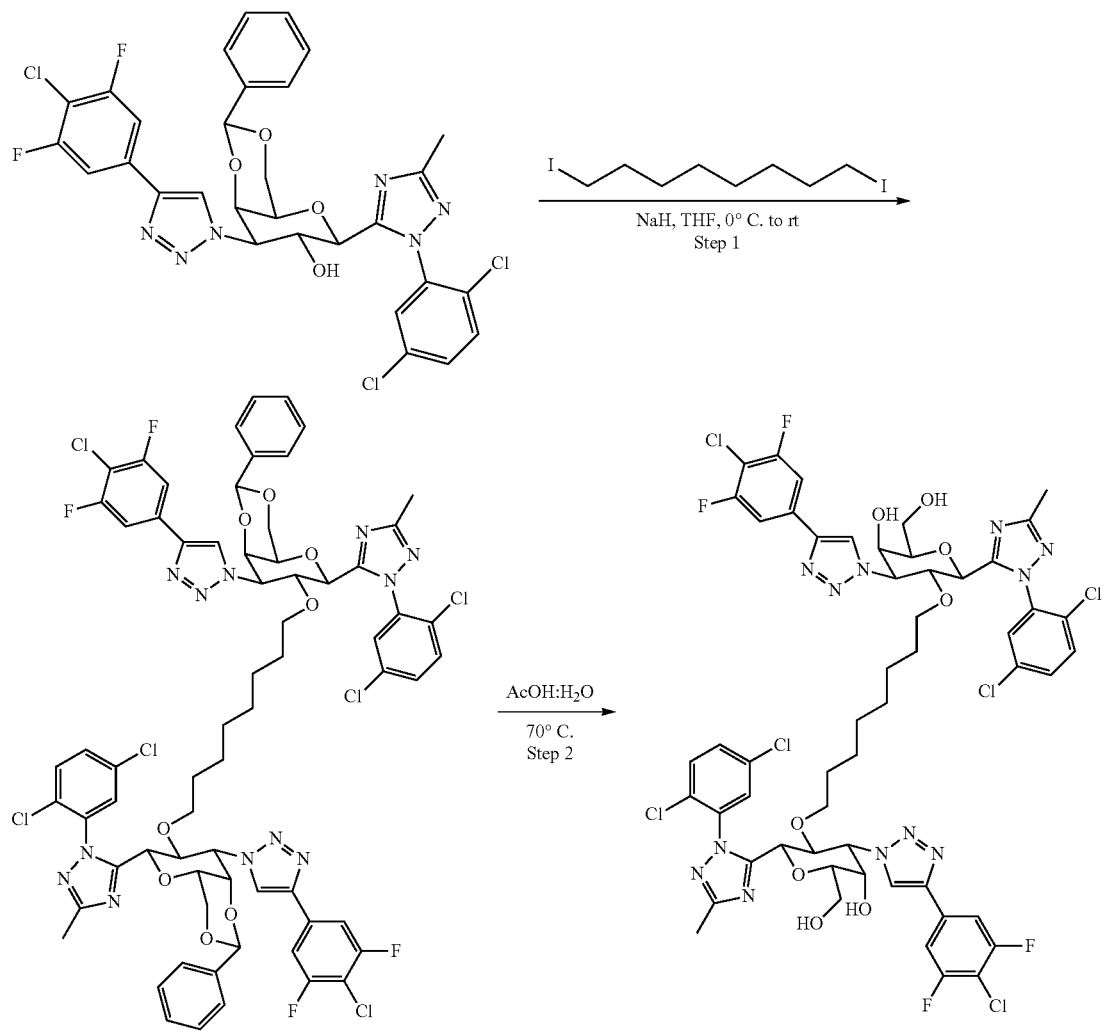

Step 1. Preparation of 1-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-8-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)octane: A solution of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (50 mg, 0.074 mmol) in THF (2 mL) was cooled to 0° C. and a sodium hydride (60% mineral oil dispersion) (0.370 mL, 0.370 mmol) was added. The mixture was stirred for 15 minutes and a solution of 1,8-diiodooctane (0.044 mL, 0.044 mmol) was added. The mixture was stirred at 0° C. and was allowed to warm to rt as the ice bath melted and warmed. After stirring for 7 days, the solvent had evaporated. An additional 1 mL of THF was added followed by 1,8-diiodooctane (0.044 mL, 0.044 mmol). After 4 additional days of stirring, the mixture was again diluted with 1 mL of THF and additional 1,8-diiodooctane (0.044 mL, 0.044 mmol) was added. After 3 days of stirring, the mixture was diluted with water (10 mL) and was extracted with ethyl acetate (3×10 mL). The organic layers were washed with brine, dried over sodium sulfate, filtered and concentrated under reduced pressure. The crude mixture of products, which included a peak with the m/z of the expected product, was used in the next step with no additional purification. LCMS: m/e 1462.3 (MH$^+$), 1.29 min (Method 1).

Step 2. To a flask containing the crude mixture above was added acetic acid (0.5 mL) and water (0.167 mL). The mixture was heated to 70° C. for 16 h. The mixture was cooled to rt then was concentrated under reduced pressure. To the residue was added potassium carbonate (35 mg) and the mixture was diluted with 0.5 mL of methanol and 0.25 mL of water. The mixture was stirred at rt for 4 h, then was diluted with water (2 mL) and was extracted with dichloromethane (3×3 mL). The organic layers were dried over sodium sulfate, filtered and concentrated under reduced pressure. The residue was dissolved in DMF and purified by preparative HPLC (Method 19). Fractions containing the product were combined and concentrated under reduced pressure to give the title product (3.7 mg, 0.0029 mmol, 8% yield over 2 steps). LCMS: m/e 1283.09 (MH$^+$), 2.63 min (Method 2). Key $^1$H NMR peaks. $^1$H NMR (500 MHz, DMSO-d6) δ 9.05 (s, 2H), 7.87-7.70 (m, 8H), 7.68-7.47 (m, 2H), 2.34 (s, 6H), 0.81-0.68 (m, 4H), 0.58-0.37 (m, 8H). IC$_{50}$=2 uM.

Example 18

Preparation of (2R,3S,4R,5S,6S)-2-(1-(2,5-dichlorophenyl)-3-methyl-11H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl ((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl) butane-1,4-diyldicarbamate

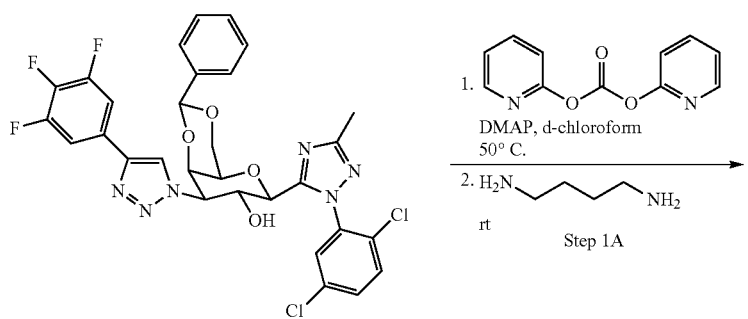

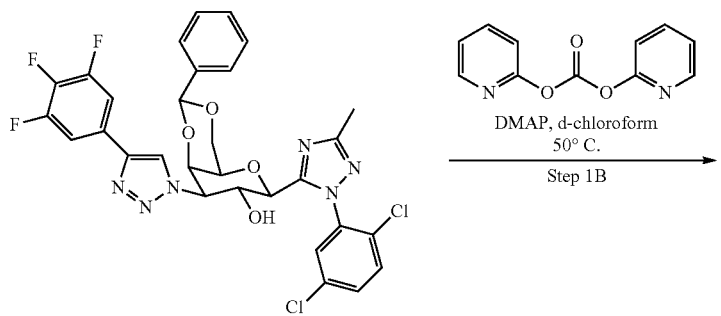

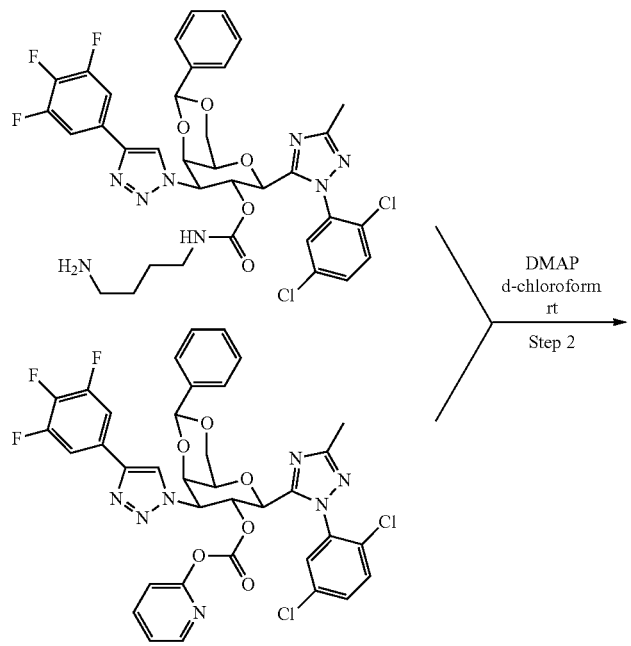

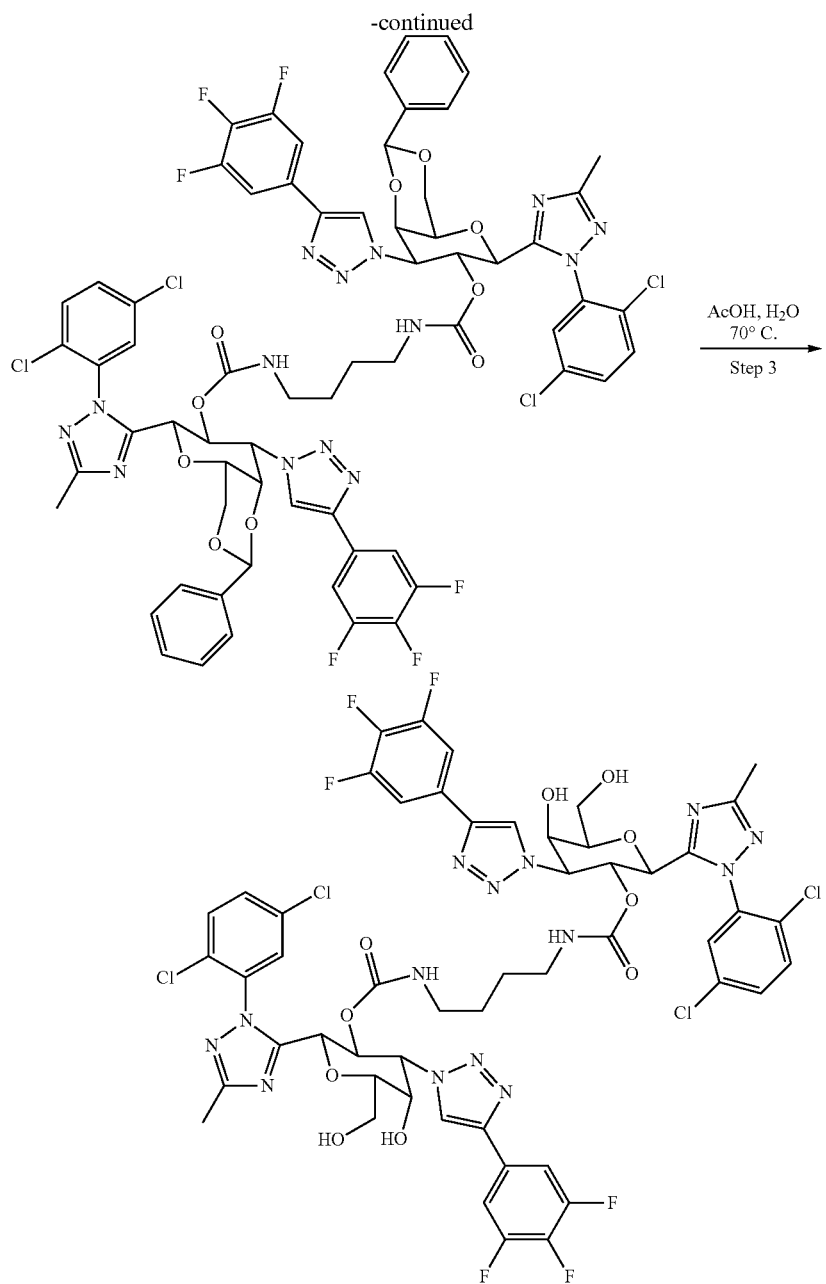

Step 1A. Preparation of (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl (4-aminobutyl)carbamate: To a solution of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (28 mg, 0.042 mmol) in d-chloroform (2 mL) was added DMAP (0.5 mg, 4.25 µmol) followed by dipyridin-2-yl carbonate (45.9 mg, 0.212 mmol). The mixture was heated to 50° C. for 3 h, then 1,4-diaminobutane (0.043 mL, 0.425 mmol) was added and the mixture was stirred at rt. After stirring the mixture for 22 h, it was diluted with water (3 mL) and extracted with dichloromethane (3×3 mL). The organic layers were dried over sodium sulfate, filtered and concentrated under reduced pressure. LC/MS showed a mixture of products including the m/z of the expected product. The crude product was used in step 2 with no additional purification. LCMS: m/e 773.8 (MH$^+$), 0.83 min (Method 1).

Step 1B. Preparation of (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl pyridin-2-yl carbonate: To a solution of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (28 mg, 0.042 mmol) in d-chloroform (2 mL) was added DMAP (0.5 mg, 4.25 µmol) followed by dipyridin-2-yl carbonate (45.9 mg, 0.212 mmol). The mixture was heated to 50° C. for 2.5 h then was cooled to rt. The mixture was diluted with sat. aq. ammonium chloride and was extracted with dichloromethane (3×10 mL). The organic layers were dried over sodium sulfate, filtered and concentrated under reduced pressure. The crude product was used in step 2 with no additional purification.

Step 2. Preparation of (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl ((2S,6R,7S,8R)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl) hexahydropyrano[3,2-d][1,3]dioxin-7-yl) butane-1,4-diyldicarbamate: To a flask containing the crude (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl pyridin-2-yl carbonate (32.8 mg, 0.042 mmol) was added a solution of the crude mixture containing (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl (4-aminobutyl)carbamate (32.5 mg, 0.042 mmol) in d-chloroform (2 mL) followed by DMAP (0.26 mg, 2.100 µmol). The mixture was stirred at rt for 18 h, then was diluted with water and extracted with dichloromethane (3×10 mL). The organic layers were dried over sodium sulfate, filtered and concentrated under reduced pressure. The residue was purified by flash chromatography using a 0-50% EtOAc in DCM gradient and a 24 g silica gel column. Fractions containing the product were combined and concentrated under reduced pressure to give the title product (24 mg, 0.016 mmol, 38% yield) as an off-white solid. LCMS: m/e 1460.3 (MH+), 1.19 min (Method 1).

Step 3. To a solution of (2S,4aR,6S,7R,8S,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl ((2S,6R,7S,8R)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl) hexahydropyrano[3,2-d][1,3]dioxin-7-yl) butane-1,4-diyldicarbamate (0.024 g, 0.016 mmol) was added acetic acid (0.5 mL) and water (0.167 mL) and the mixture was heated to 70° C. for 20.5 h. The mixture was cooled to rt and concentrated under a stream of nitrogen. To the residue was added 0.035 g of potassium carbonate and the mixture was diluted with 0.5 mL of MeOH and 0.25 mL of water. The mixture was stirred at rt for 3 h, then was concentrated under a stream of nitrogen, diluted with DMF, filtered through a plug of glass wool and purified by preparative HPLC (Method 20). Fractions containing the product were concentrated under reduced pressure to give the title product (8.2 mg, 0.0064 mmol, 40% yield). LCMS: m/e 1281.04 (MH+), 1.91 min (Method 2). Key $^1$H NMR peaks: $^1$H NMR (500 MHz, DMSO-d6) δ 8.49 (br s, 2H), 7.75-7.55 (m, 10H), 2.18 (s, 6H), 0.75 (br s, 4H). IC$_{50}$=0.019 uM.

Example 19

Preparation of (2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl ((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl) propane-1,3-diyldicarbamate

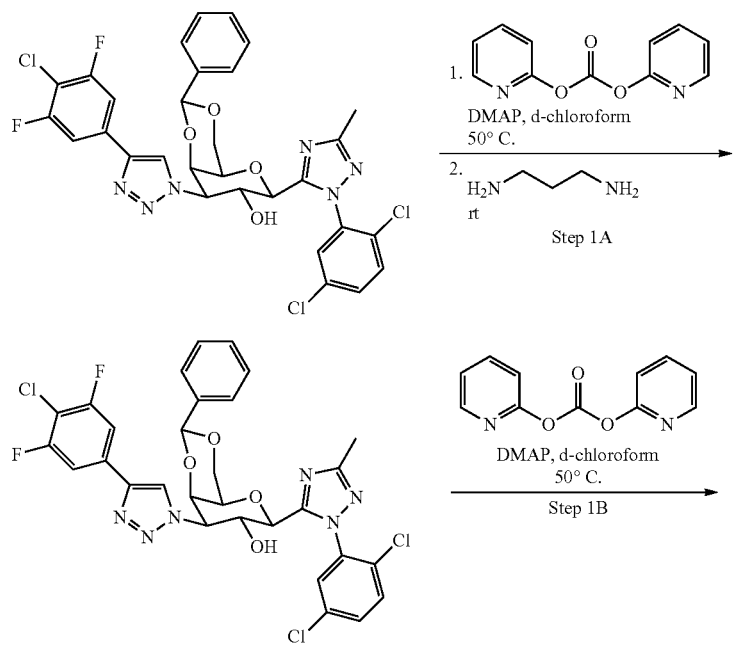

-continued
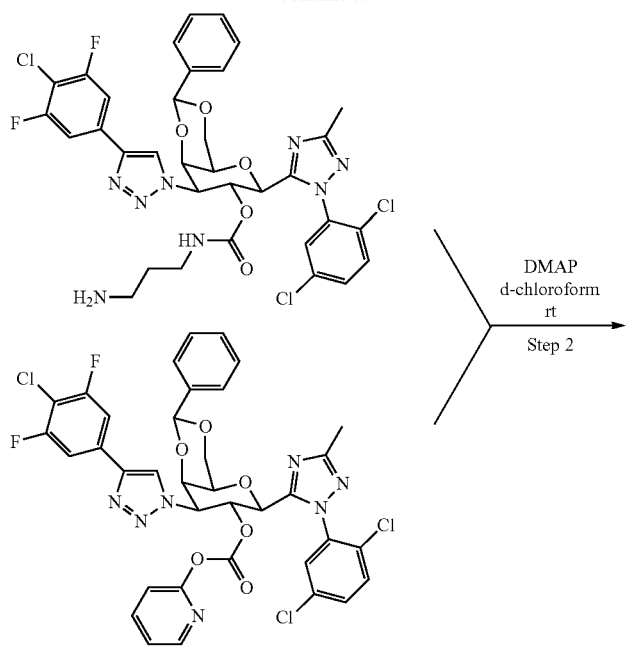
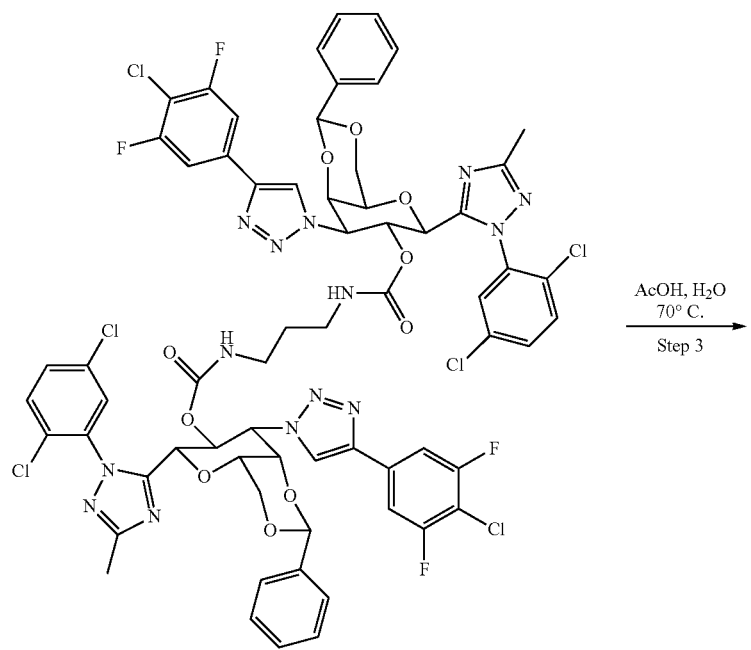

-continued

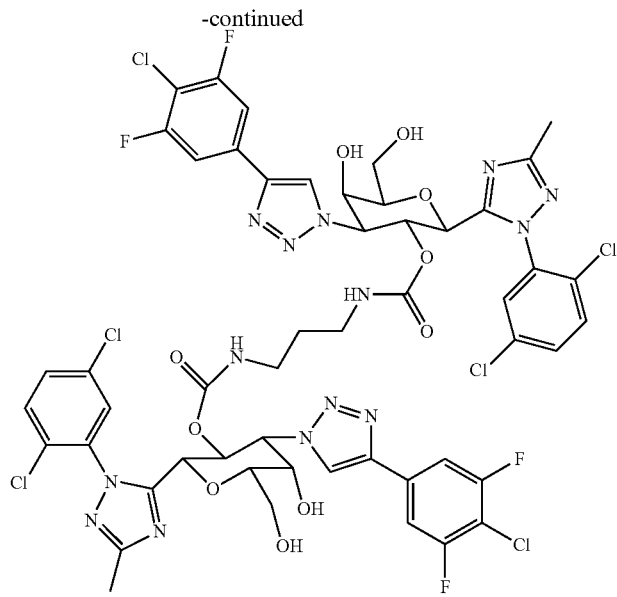

Step 1A. Preparation of (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl (3-aminopropyl)carbamate: To a solution of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.063 g, 0.093 mmol) in d-chloroform (2 mL) was added DMAP (1.1 mg, 9.32 µmol) followed by dipyridin-2-yl carbonate (0.101 g, 0.466 mmol). The mixture was heated to 50° C. for 2 h then was cooled to rt. To the mixture was added propane-1,3-diamine (0.078 mL, 0.932 mmol) and it was stirred at rt for 4 h. The mixture diluted with sat. aq. ammonium chloride and was extracted with dichloromethane (3×10 mL). The organic layers were dried over sodium sulfate, filtered and concentrated under reduced pressure to give a mixture of products which included a peak with the m/z of the title compound. The crude product was used in step 2 with no additional purification. LCMS: m/e 777.3 (MH$^+$), 0.84 min (Method 1).

Step 1B. Preparation of (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl pyridin-2-yl carbonate: To a solution of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.05 g, 0.074 mmol) in d-chloroform (3 mL) was added DMAP (0.9 mg, 7.40 µmol) followed by dipyridin-2-yl carbonate (0.080 g, 0.370 mmol). The mixture was heated to 50° C. for 2 h then was cooled to rt. The mixture was diluted with sat. aq. ammonium chloride and was extracted with dichloromethane (3×10 mL). The organic layers were dried over sodium sulfate, filtered and concentrated under reduced pressure to give the title product. The crude product was used in step 2 with no additional purification.

Step 2. Preparation of (2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl ((2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl) propane-1,3-diyldicarbamate: To a flask containing the crude (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl (3-aminopropyl)carbamate (0.072 g, 0.093 mmol) and (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl pyridin-2-yl carbonate (0.059 g, 0.074 mmol) in d-chloroform (3 mL) was added DMAP (0.9 mg, 7.40 µmol) and the mixture was stirred at rt for 18 h. The mixture was diluted with water (3 mL) and was extracted with dichloromethane (3×3 mL). The organic layers were dried over sodium sulfate, filtered and concentrated under reduced pressure. The residue was dissolved in DMF, filtered through a plug of glass wool and was purified by prep HPLC. The fractions containing the product were combined and concentrated under reduced pressure to give a mixture of products (54 mg) including the title compound. LCMS: m/e 1479.5 (MH$^+$), 1.22 min (Method 1).

Step 3. A solution of the mixture of products from step 2 (54 mg) in acetic acid (0.5 mL) and water (0.167 mL) was heated to 70° C. After 15.5 h, the mixture was cooled to rt and was concentrated under a stream of nitrogen. To the residue was added 0.035 g of potassium carbonate then the mixture was diluted with 0.5 mL of MeOH and 0.25 mL of water. After stirring the mixture at rt for 1 h, it was further diluted with 1 mL of methanol and was heated to 50° C. After 1 h of heating, the mixture was cooled to rt and was stirred at rt overnight. The mixture was then heated to 50° for 2 h, was cooled to rt and was concentrated under a steam of nitrogen. The residue was diluted with DMF and was filtered through a plug of glass wool to remove the solids. The DMF solution was purified by preparative HPLC (Method 21). Fractions containing the product were combined and concentrated under reduced pressure to give the title product (29.0 mg, 0.022 mmol, 30% yield over 3 steps). LCMS: m/e 1299.2 (MH$^+$), 2.09 min (Method 2). Key $^1$H NMR peaks: $^1$H NMR (500 MHz, DMSO-d6) δ 8.57 (br s, 2H), 7.79-7.50 (m, 10H), 2.14 (s, 6H), 0.94 (br s, 2H). IC$_{50}$=0.11 uM.

Example 20
Preparation of (2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl ((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl) ethane-1,2-diylbis(methylcarbamate)
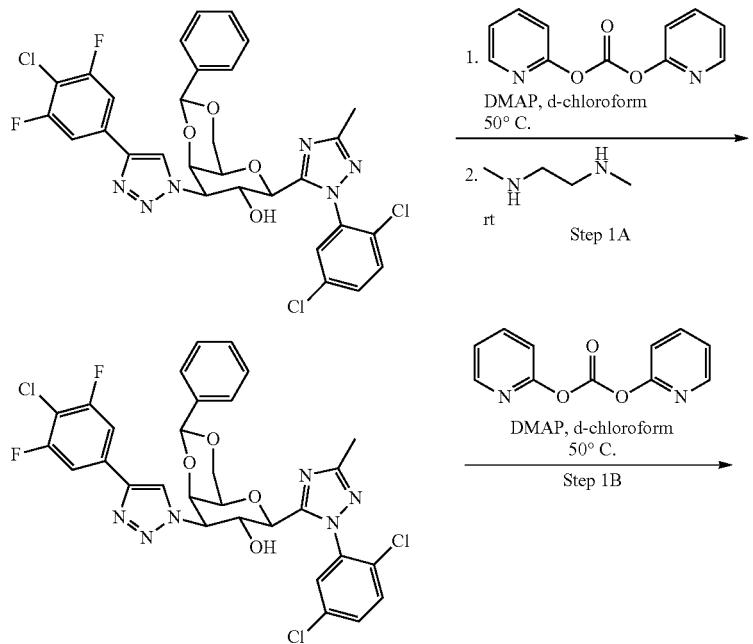
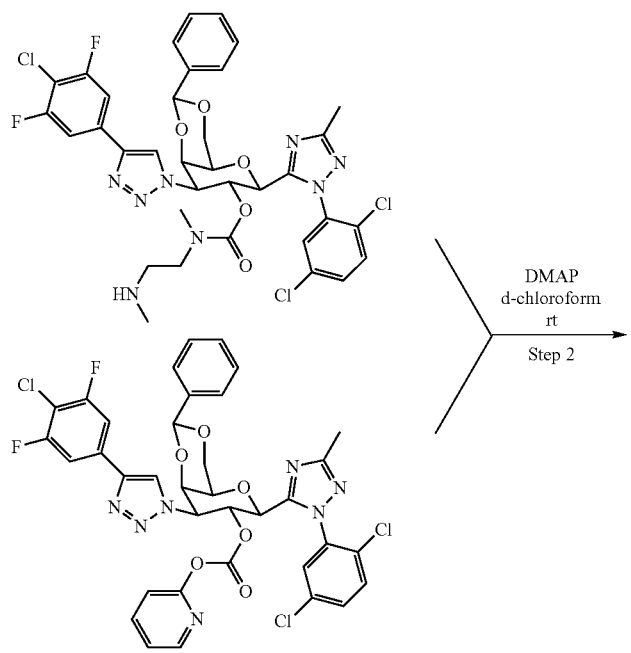

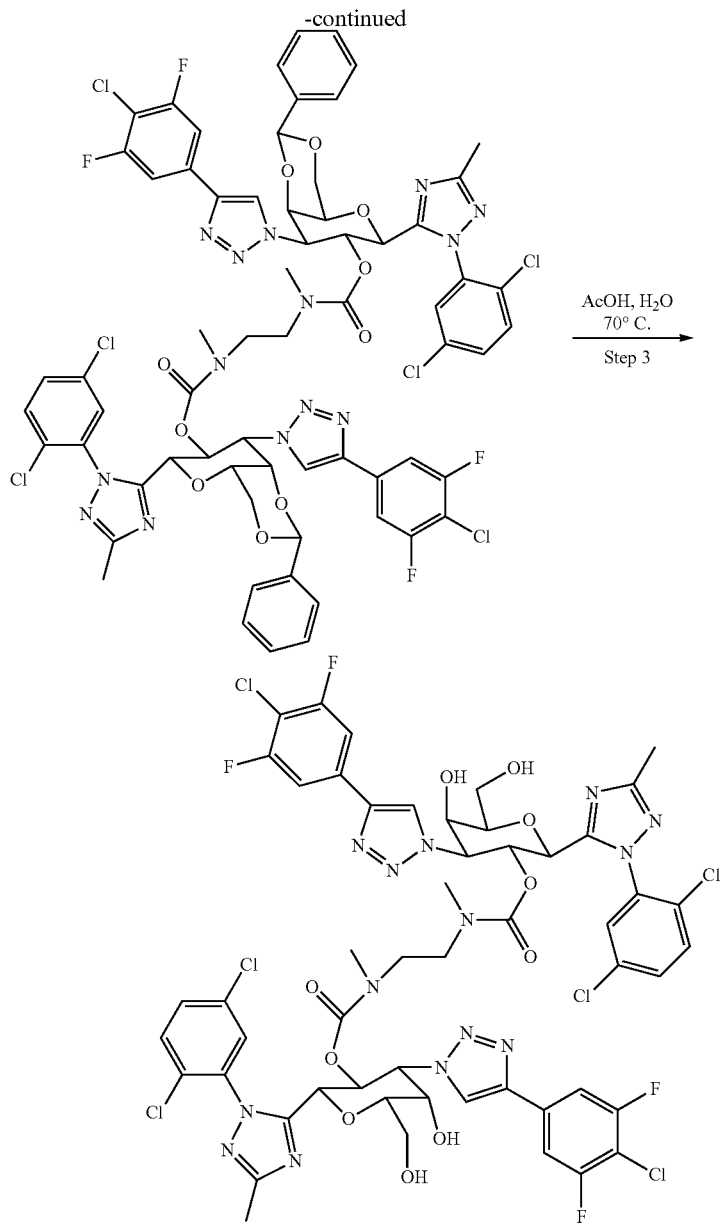

Step 1A. Preparation of (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl methyl(2-(methylamino)ethyl)carbamate: To a solution of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.065 g, 0.096 mmol) in d-chloroform (2 mL) was added DMAP (1.2 mg, 9.62 μmol) followed by dipyridin-2-yl carbonate (0.104 g, 0.481 mmol). The mixture was heated to 50° C. for 2 h then was cooled to rt. The mixture was dilute with aq. ammonium chloride and was extracted with dichloromethane (3×7 mL). The organic layers were dried over sodium sulfate, filtered and concentrated under reduced pressure. The residue was dissolved in d-chloroform (2 mL), DMAP (1.175 mg, 9.62 μmol) was added followed by N1,N2-dimethylethane-1,2-diamine (0.042 g, 0.481 mmol). The mixture was stirred at rt for 2 h then was diluted with water and was extracted with dichloromethane (3×5 mL). The organic layers were dried over sodium sulfate, filtered and concentrated under reduced pressure. The crude mixture of products which included the title product was used in step 2 with no additional purification. LCMS: m/e 791.3 (MH+), 0.88 min (Method 1).

Step 1B. Preparation of (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl pyridin-2-yl carbonate: To a solution of (2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-ol (0.05 g, 0.074 mmol) in d-chloroform (2 mL) was added DMAP (0.9 mg, 7.40 μmol) followed by dipyridin-2-yl carbonate (0.080 g, 0.370 mmol). The mixture was heated to 50° C. After 3 h of heating, the mixture was cooled to rt, diluted with aq. ammonium chloride and was extracted with dichloromethane (3×7 mL). The organic layers were dried over sodium sulfate, filtered and concentrated under reduced pressure. The crude product was used in step 2 with no additional purification.

Step 2. Preparation of (2R,4aS,6R,7S,8R,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl ((2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl) ethane-1,2-diylbis(methylcarbamate): To a solution of the crude (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl methyl(2-(methylamino)ethyl)carbamate (0.076 g, 0.096 mmol) and (2S,4aR,6S,7R,8S,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl pyridin-2-yl carbonate (0.059 g, 0.074 mmol) in d-chloroform (2 mL) was added DMAP (0.904 mg, 7.40 µmol). The mixture was heated to 50° C. for 15.5 h, then was diluted with water and extracted with dichloromethane (3×10 mL). The organic layers were dried over sodium sulfate, filtered and concentrated under reduced pressure. The residue was purified by preparative HPLC (Method 2). Fractions containing the title product were combined and concentrated under reduced pressure. Upon concentrating, a mixture of products formed as the benzylidine acetal protecting group was partially cleaved. 8 mg of a mixture of products was used in step 3 with no additional purification. LCMS: m/e 1493.4 (MH+), 1.25 min (Method 1).

Step 3. To a vial containing the mixture of products from step 2 was added acetic acid (0.5 mL) and water (0.167 mL) and the mixture was heated to 70° C. After heating the mixture for 18.5 h, it was cooled to rt. The mixture was concentrated under a stream of nitrogen then was diluted with 0.5 mL of methanol and 0.25 mL of water and 0.035 g of potassium carbonate was added. The mixture was stirred at rt for 24 h, then was concentrated under a stream of nitrogen. The residue was diluted with DMF, filtered through a plug of glass wool and was purified by preparative HPLC. Fractions containing the product were concentrated under reduced pressure to give the title product (3.2 mg, 0.0024 mmol, 3% yield over 3 steps). LCMS: m/e 1313.06 (MH+), 2.21 min (Method 2). Key $^1$H NMR peaks: $^1$H NMR (500 MHz, DMSO-d6) δ 8.84-8.60 (m, 2H), 7.87-7.47 (m, 10H), 2.31-2.08 (m, 12H).

Example 21

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-(2-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-N-methylacetamido)ethyl)-N-methylacetamide

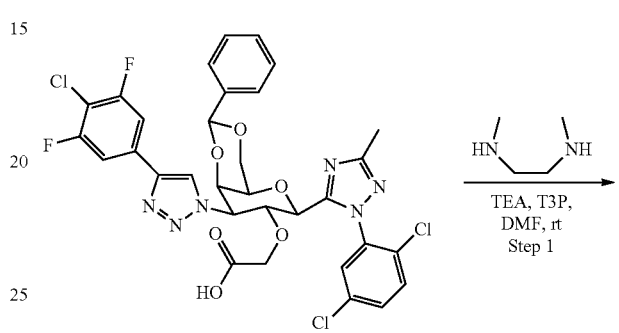

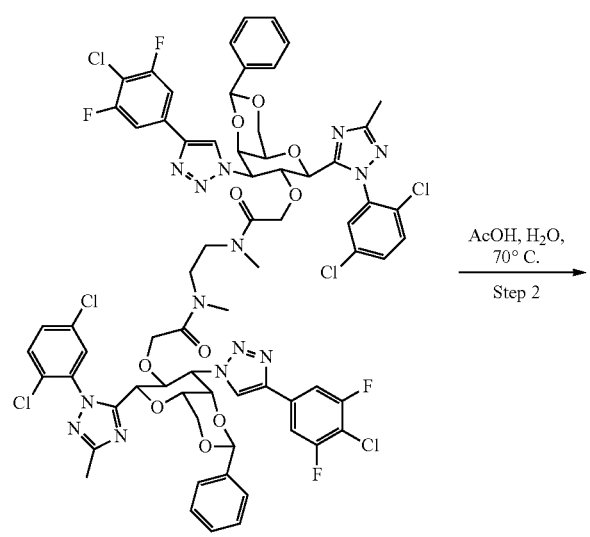

-continued

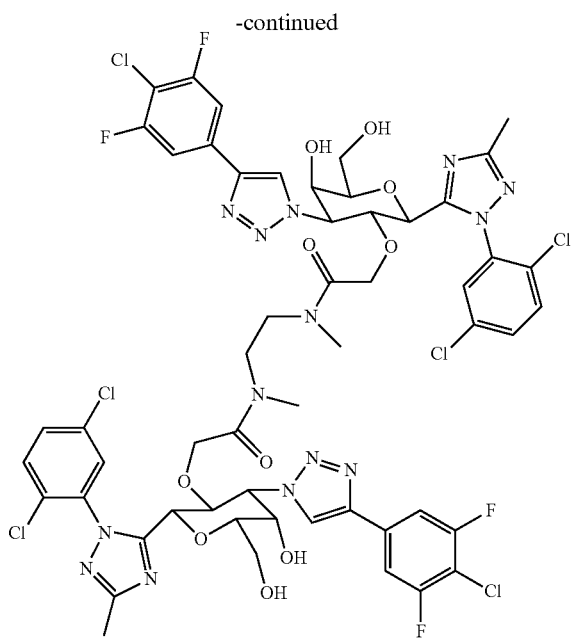

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(2-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-methylacetamido)ethyl)-N-methylacetamide: To a vial containing 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (0.168 g, 0.229 mmol) was added DMF (2 mL), TEA (0.128 mL, 0.916 mmol), N1,N2-dimethylethane-1,2-diamine (0.092 mL, 0.092 mmol) and 1-propanephosphonic anhydride (T3P, 50% in EtOAc) (0.340 mL, 0.572 mmol). The mixture was stirred at rt for 17 h then an additional 0.046 mL of the N1,N2-dimethylethane-1,2-diamine was added and the mixture was stirred at rt for 24 h. An additional 0.092 mL of N1,N2-dimethylethane-1,2-diamine was added and the mixture was stirred at rt for an additional 24 h. The mixture was diluted with water (10 mL) and was extracted with ethyl acetate (2×10 mL). The organic layers were washed with water (3×10 mL), then with brine and were dried over sodium sulfate, filtered and concentrated under reduced pressure. The residue was purified by flash chromatography using a 0-100% ethyl acetate in dichloromethane gradient. The fractions containing the title product were combined and concentrated under reduced pressure to give the product (0.095 g, 0.0625 mmol, 55% yield) as an off-white solid. LCMS: m/e 1521.4 (MH+), 1.21 min (Method 1).

Step 2. To a flask containing 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-(2-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-N-methylacetamido)ethyl)-N-methylacetamide (0.09 g, 0.059 mmol) was added acetic acid (1 mL) and water (0.33 mL) and the mixture was heated to 70° C. After heating the mixture for 19.5 h, the mixture was cooled to rt and was concentrated under reduced pressure. The residue was diluted with DCM and concentrated two additional times. The residue was dilute with 1 mL of methanol and 0.5 mL of water and 0.07 g of potassium carbonate was added. The mixture was stirred at rt for 5 h, then was concentrated under reduced pressure, was diluted with DMF and filtered through a plug of glass wool to remove the solids. The filtrate was purified by preparative HPLC (Method 22). Fractions containing the product were combined and concentrated under reduced pressure to give the title product (46.6 mg, 0.035 mmol, 59% yield). LCMS: m/e 1341.18 (MH+), 2.08 min (Method 2). Key $^1$H NMR peaks: $^1$H NMR (500 MHz, DMSO-d6) δ 9.11-8.95 (m, 2H), 7.97-7.44 (m, 10H), 2.85 (s, 3H), 2.69 (s, 3H), 2.32-2.17 (m, 6H). $IC_{50}$=0.002 uM.

Example 22

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-1-(4-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetyl)piperazin-1-yl)ethan-1-one

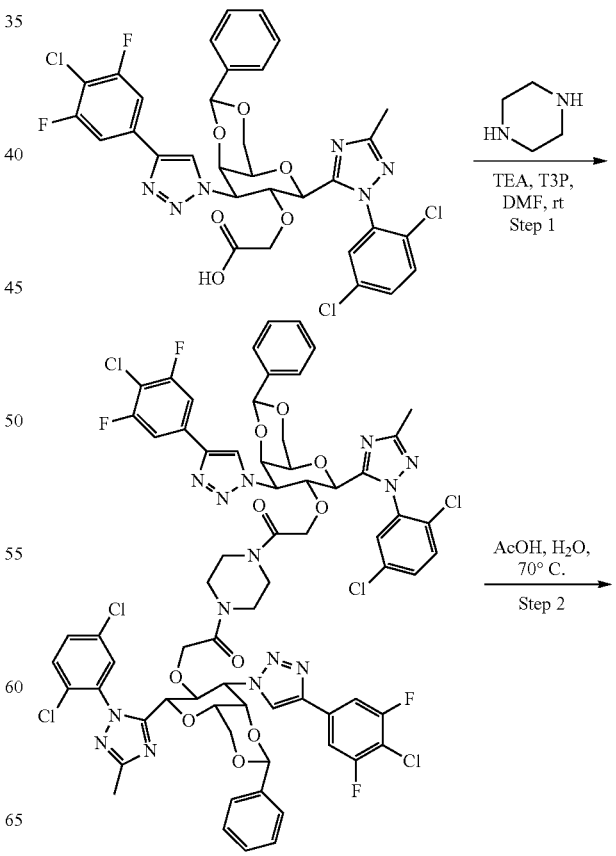

-continued

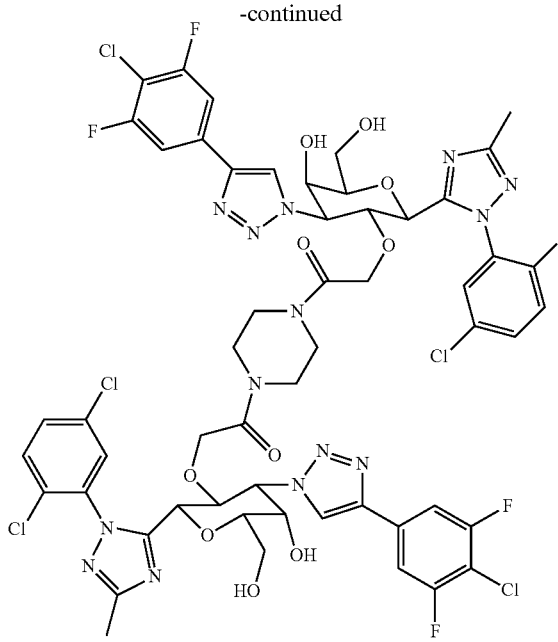

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-1-(4-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetyl)piperazin-1-yl)ethan-1-one: To a vial containing 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (0.125 g, 0.170 mmol) was added DMF (2 mL), TEA (0.095 mL, 0.681 mmol), piperazine (0.5M in DMF:THF (1:1)) (0.136 mL, 0.068 mmol) and 1-propanephosphonic anhydride (T3P, 50% in EtOAc) (0.253 mL, 0.426 mmol). The mixture was stirred at rt for 17 h then was diluted with water (20 mL) and extracted with ethyl acetate (2×20 mL). The organic layers was washed with water (3×20 mL) then with brine and were dried over sodium sulfate, filtered and concentrated under reduced pressure. The crude product was used in the next step with no additional purification. LCMS: m/e 1517.6 (MH+), 1.18 min (Method 1).

Step 2. To a flask containing 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-1-(4-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetyl)piperazin-1-yl)ethan-1-one (129 mg, 0.085 mmol) was added acetic acid (2 mL) and water (0.667 mL) and the mixture was heated to 70° C. After heating the mixture for 18 h, it was cooled to rt and concentrated under reduced pressure. The residue was diluted with 5 mL of methanol and 2.5 mL of water and 0.07 g of potassium carbonate was added. The mixture was stirred at rt for 24 h, then was concentrated under reduced pressure. The residue was diluted with DMF, filtered through a plug of glass wool and the filtrate was purified by preparative HPLC (Method 23). Fractions containing the product were concentrated under reduced pressure to give the title product (46.1 mg, 0.034 mmol, 40% yield over two steps). LCMS: m/e 1339.3 (MH+), 2.02 min (Method 2). Key $^1$H NMR peaks. $^1$H NMR (600 MHz, DMSO-d6) δ 9.07 (br s, 2H), 7.90-7.79 (m, 6H), 7.77 (d, J=8.6 Hz, 2H), 7.73 (dd, J=8.6, 2.2 Hz, 2H), 5.43 (d, J=6.0 Hz, 2H), 5.19 (br d, J=10.3 Hz, 2H), 4.85-4.69 (m, 2H), 4.65 (t, J=5.5 Hz, 2H), 4.42 (br d, J=7.9 Hz, 2H), 4.22-4.05 (m, 1H), 3.90 (br s, 2H), 3.81 (br s, 3H), 3.70 (t, J=6.5 Hz, 2H), 3.47-3.37 (m, 4H), 2.32 (br s, 6H). IC$_{50}$=0.004 uM.

Example 23

Preparation of 2-(((2R,3S,4R,5S,6S)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)-1-(4-(2-(((2S,3R,4S,5R,6R)-4-(4-(4-chloro-3,5-difluorophenyl)-1H-1,2,3-triazol-1-yl)-2-(1-(2,5-dichlorophenyl)-3-methyl-1H-1,2,4-triazol-5-yl)-5-hydroxy-6-(hydroxymethyl)tetrahydro-2H-pyran-3-yl)oxy)acetyl)-1,4-diazepan-1-yl)ethan-1-one

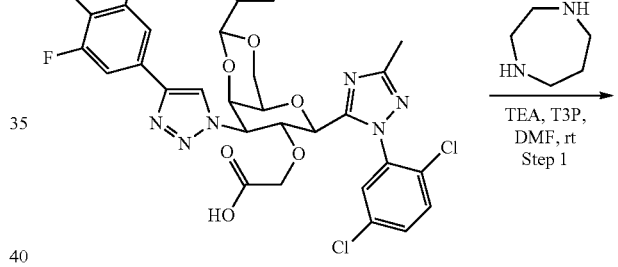

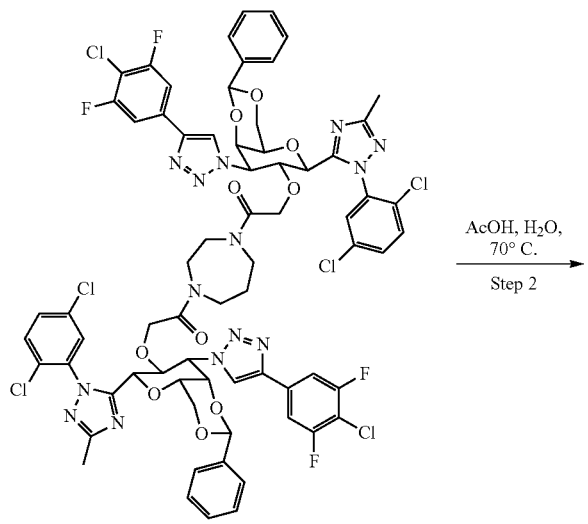

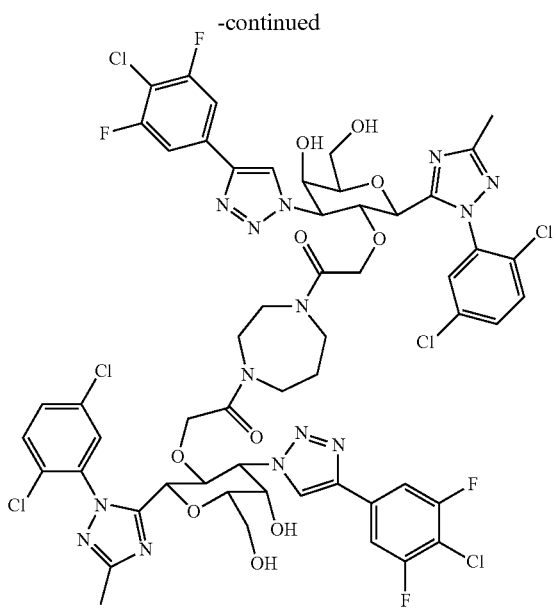

Step 1. Preparation of 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-1-(4-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetyl)-1,4-diazepan-1-yl)ethan-1-one: To a flask containing 2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetic acid (0.05 g, 0.068 mmol) was added DMF (1 mL), TEA (0.038 mL, 0.273 mmol), homopiperazine (1M in DMF) (0.034 mL, 0.034 mmol) and 1-propanephosphonic anhydride (T3P, 50% in EtOAc) (0.101 mL, 0.170 mmol). The mixture was stirred at rt then was diluted with water (10 mL) and was extracted with ethyl acetate (3×10 mL). The organic layers were washed with water (3×20 mL), then with brine and were dried over sodium sulfate. The drying agent was removed by filtration and the filtrate was concentrated under reduced pressure to give the crude product (0.048 g, 0.031 mmol, 91% yield) as an off-white solid. LCMS: m/e 1533.5 (MH+), 1.21 min (Method 1).

Step 2. To a flask containing 2-(((2R,4aS,6R,7S,8S,8aS)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)-1-(4-(2-(((2S,4aR,6S,7R,8R,8aR)-8-(4-(4-chloro-3,5-difluorophenyl)-1H-1,2,3-triazol-1-yl)-6-(1-(2,5-dichlorophenyl)-3-methyl-1H-1,2,4-triazol-5-yl)-2-phenylhexahydropyrano[3,2-d][1,3]dioxin-7-yl)oxy)acetyl)-1,4-diazepan-1-yl)ethan-1-one (0.048 g, 0.031 mmol) was added acetic acid (1 mL) and water (0.33 mL). The mixture was heated to 70° C. for 15 h, then was cooled to rt and concentrated under reduced pressure. The residue was diluted with 2 mL of MeOH and 0.5 mL of water and 0.07 g of potassium carbonate was added. The mixture was stirred at rt overnight, then was concentrated under reduced pressure. The residue was diluted with DMF and filtered through a plug of glass wool to remove the solids. The filtrate was purified by preparative HPLC (Method 24). Fractions containing the product were concentrated under reduced pressure to give the title product (15.1 mg, 0.0111 mmol, 36% yield). LCMS: m/e 1353.16 (MH+), 2.04 min (Method 2). $^1$H NMR (500 MHz, DMSO-d6) δ 9.09-8.94 (m, 2H), 7.94-7.60 (m, 12H), 5.44-5.35 (m, 2H), 5.18-5.08 (m, 2H), 4.78-4.58 (m, 4H), 4.41-4.26 (m, 2H), 3.91-3.80 (m, 2H), 3.64 (br d, J=6.1 Hz, 2H), 2.50 (s, 14H), 2.31-2.22 (m, 6H), 1.26-1.02 (m, 2H). IC$_{50}$=0.004 uM.

We claim:
1. A compound of formula I

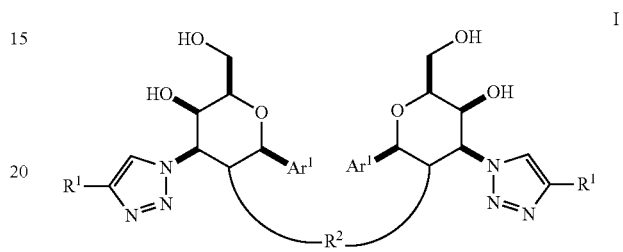

where:

$R^1$ is $((R^3)(R^4)N)$carbonyl or $Ar^2$;

$R^2$ is —O-$L^1$-O—, —OCON($R^5$)-$L^2$-N($R^5$)C(O)O—, or —O-($L^3$)-CON($R^5$)-$L^2$-N($R^5$)C(O)-($L^3$)-O—;

$L^1$ is alkylene;

$L^2$ is alkylene, or —CH$_2$-Ph-CH$_2$—;

or N($R^5$)-$L^2$-N($R^5$) taken together is piperazinyl, or homopiperazinyl;

$L^3$ is alkylene;

$R^3$ is hydrogen, alkyl, cycloalkyl, benzyl, or halobenzyl;

$R^4$ is hydrogen or alkyl;

or $(R^3)(R^4)$N taken together is azetidinyl, pyrrolidinyl, piperidinyl, piperazinyl, or morpholinyl, and is substituted with 0-3 substituents selected from halo, alkyl, and alkylcarbonyl;

$R^5$ is hydrogen or alkyl;

$R^6$ is hydrogen or alkyl;

$R^7$ is hydrogen or alkyl;

or $(R^6)(R^7)$N taken together is azetidinyl, pyrrolidinyl, piperidinyl, piperazinyl, or morpholinyl, and is substituted with 0-3 substituents selected from halo, alkyl, and hydroxy;

$R^8$ is hydrogen, alkyl, alkylcarbonyl, or alkylsulfonyl;

$R^9$ is hydrogen or alkyl;

or $(R^8)(R^9)$N taken together is azetidinyl, pyrrolidinyl, piperidinyl, piperazinyl, or morpholinyl, and is substituted with 0-3 substituents selected from halo, alkyl, and alkylcarbonyl;

$R^{10}$ is cyano, halo, alkoxy, or $(R^{11})(R^{12})$N;

$R^{11}$ is hydrogen or alkyl;

$R^{12}$ is hydrogen or alkyl;

or $(R^{11})(R^{12})$N taken together is azetidinyl, pyrrolidinyl, piperidinyl, piperazinyl, or morpholinyl;

$R^{13}$ is hydrogen, alkyl, alkylcarbonyl, alkoxycarbonyl, or alkylsulfonyl;

$R^{14}$ is hydrogen or alkyl;

or $(R^{13})(R^{14})$N taken together is azetidinyl, pyrrolidinyl, piperidinyl, piperazinyl, or morpholinyl, and is substituted with 0-3 substituents selected from halo, alkyl, and hydroxy;

$R^{15}$ is hydrogen, alkyl, alkylcarbonyl, or alkylsulfonyl;
$R^{16}$ is hydrogen or alkyl;
or $(R^{15})(R^{16})N$ taken together is azetidinyl, pyrrolidinyl, piperidinyl, piperazinyl, or morpholinyl, and is substituted with 0-3 substituents selected from halo, alkyl, and alkylcarbonyl;
$Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, phenyl, or indolyl, and is substituted with 0-3 substituents selected from alkyl, haloalkyl, hydroxyalkyl, alkoxyalkyl, (carboxy)alkyl, (alkoxycarbonyl)alkyl, ($H_2NCO$)alkyl, ($Ar^3$)alkyl, cycloalkyl, hydroxycycloalkyl, alkenyl, alkoxy, alkylthio, alkylsulfonyl, carboxy, alkoxycarbonyl, (alkylNH)carbonyl, $(((R^6)(R^7)N)$alkylNH)carbonyl, ((pyridinyl)alkylNH)carbonyl, $(R^8)(R^9)N$, and $Ar^3$;
$Ar^2$ is phenyl, pyridinyl, naphthyl, benzoxazolyl, benzothiazolyl, quinolinyl, or quinoxalinyl, and is substituted with 0-5 substituents selected from cyano, halo, alkyl, $(R^{10})$alkyl, haloalkyl, cycloalkyl, $(R^{10})$ cycloalkyl, alkoxy, cycloalkoxy, haloalkoxy, and $(R^{13})(R^{14})N$; and
$Ar^3$ is phenyl, naphthalinyl, biphenyl, pyridinyl, pyridazinyl, pyrimidinyl, pyrazinyl, quinolinyl, isoquinolinyl, quinoxainyl, indolyl, indazolyl, benzimidazolyl, benzisoxazolyl, benzisothiazolyl, benzoxazolyl, benzothiazolyl, benzodioxolyl, dihydrobenzodioxinyl, dihydroquinolinonyl, or dihydrobenzothiophene-2,2-dioxide, and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{15})(R^{16})N$;
or $Ar^3$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, nitro, halo, alkyl, haloalkyl, alkoxy, haloalkoxy, alkylthio, carboxy, alkoxycarbonyl, $CONH_2$, and $(R^{15})(R^{16})N$;
or $Ar^3$ is (alkyl$SO_2$)phenyl, (alkyl$SO_2$)(halo)phenyl, (amino$SO_2$)phenyl, (dialkylamino$SO_2$)phenyl, ((alkylNH$SO_2$)alkyl)phenyl, (pyrrolyl)phenyl, (imidazolyl)phenyl, (oxazolyl)phenyl, (tetrazolyl)phenyl, ((pyridinyl)methyl)phenyl, phenoxyphenyl, (benzyloxy)phenyl, ((methyl)thiazolyl)phenyl, (thiazolyl)benzenesulfamido, ((methyl)thiadiazolyl)benzenesulfamido, (methyl)benzothiazolonyl, or fluoropyrazolopyrimidinyl;
or a pharmaceutically acceptable salt thereof.

2. A compound of claim 1 where $R^1$ is $Ar^2$; $Ar^1$ is triazolyl substituted with 0-3 substituents selected from alkyl, haloalkyl, hydroxyalkyl, alkoxyalkyl, (carboxy)alkyl, (alkoxycarbonyl)alkyl, ($H_2NCO$)alkyl, ($Ar^3$)alkyl, cycloalkyl, hydroxycycloalkyl, alkenyl, alkoxy, alkylthio, alkylsulfonyl, carboxy, alkoxycarbonyl, (alkylNH)carbonyl, $(((R^6)(R^7)N)$alkylNH)carbonyl, ((pyridinyl)alkylNH)carbonyl, $(R^8)(R^9)N$, and $Ar^3$; $Ar^2$ is phenyl or pyridinyl and is substituted with 0-5 substituents selected from cyano, halo, alkyl, $(R^{10})$alkyl, haloalkyl, cycloalkyl, $(R^{10})$cycloalkyl, alkoxy, cycloalkoxy, haloalkoxy, and $(R^{13})(R^{14})N$; and $Ar^3$ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{15})(R^{16})N$; or a pharmaceutically acceptable salt thereof.

3. A compound of claim 1 where $R^1$ is $Ar^2$; $R^2$ is hydroxy; $Ar^1$ is triazolyl substituted with 0-2 substituents selected from alkyl, haloalkyl, and $Ar^3$; $Ar^2$ is phenyl substituted with 0-5 halo substituents; and $Ar^3$ is phenyl substituted with 0-5 substituents selected from halo, alkyl, haloalkyl, cycloalkyl, alkoxy, and haloalkoxy; or a pharmaceutically acceptable salt thereof.

4. A compound of claim 1 where $R^1$ is $Ar^2$.

5. A compound of claim 1 where $Ar^1$ is triazolyl substituted with 0-3 substituents selected from alkyl, haloalkyl, hydroxyalkyl, alkoxyalkyl, (carboxy)alkyl, (alkoxycarbonyl)alkyl, ($H_2NCO$)alkyl, ($Ar^3$)alkyl, cycloalkyl, hydroxycycloalkyl, alkenyl, alkoxy, alkylthio, alkylsulfonyl, carboxy, alkoxycarbonyl, (alkylNH)carbonyl, $(((R^6)(R^7)N)$alkylNH)carbonyl, ((pyridinyl)alkylNH)carbonyl, $(R^8)(R^9)N$, and $Ar^3$.

6. A compound of claim 1 where $Ar^1$ is triazolyl substituted with 0-2 substituents selected from alkyl, haloalkyl, and $Ar^3$.

7. A compound of claim 1 where $Ar^2$ is phenyl or pyridinyl and is substituted with 0-5 substituents selected from cyano, halo, alkyl, $(R^{10})$alkyl, haloalkyl, cycloalkyl, $(R^{10})$cycloalkyl, alkoxy, cycloalkoxy, haloalkoxy, and $(R^{13})(R^{14})N$.

8. A compound of claim 1 where $Ar^2$ is phenyl substituted with 0-5 halo substituents.

9. A compound of claim 1 where $Ar^3$ is phenyl substituted with 0-5 substituents selected from cyano, halo, alkyl, haloalkyl, alkoxy, and haloalkoxy.

10. A composition comprising a therapeutically effective amount of a compound of claim 1, or a pharmaceutically acceptable salt thereof, and a pharmaceutically acceptable carrier.

11. A method for use in treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 1, or a pharmaceutically acceptable salt thereof, to a patient in need.

12. A method for treating a disease or condition selected from renal fibrosis, pulmonary fibrosis, hepatic fibrosis, arterial fibrosis, and systemic sclerosis; comprising administering a therapeutically effective amount of a compound of claim 1, or a pharmaceutically acceptable salt thereof to a patient.

13. A compound selected from:
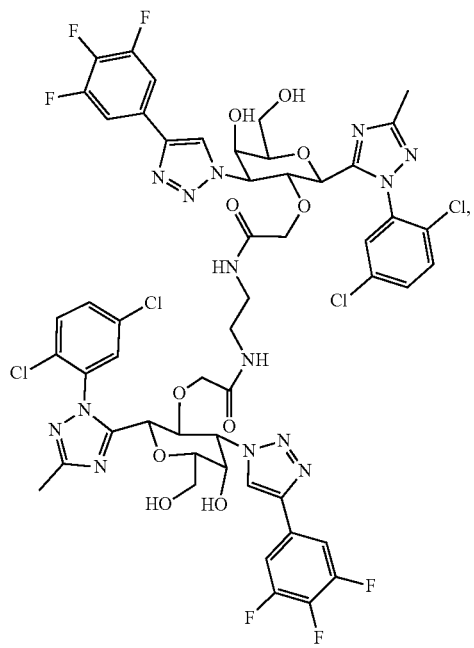
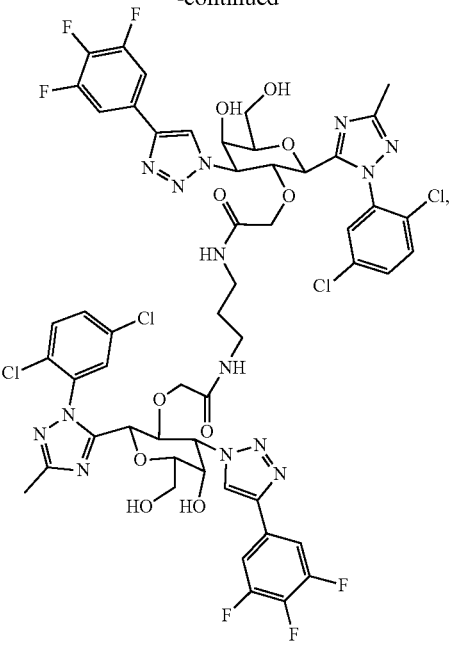
-continued
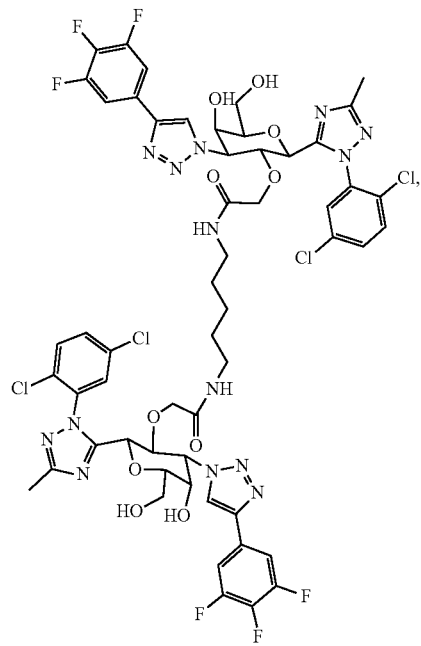
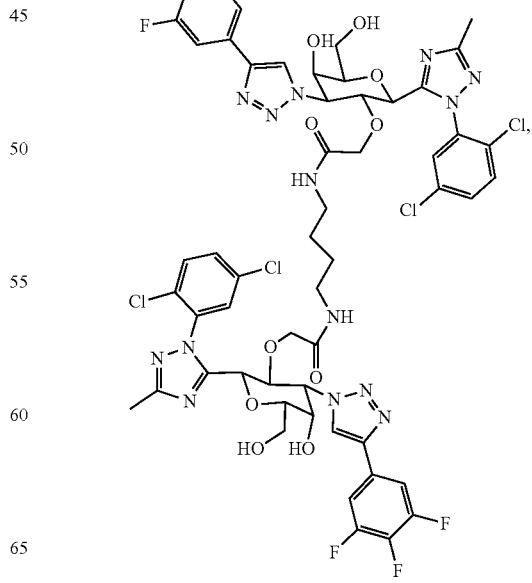

85
-continued
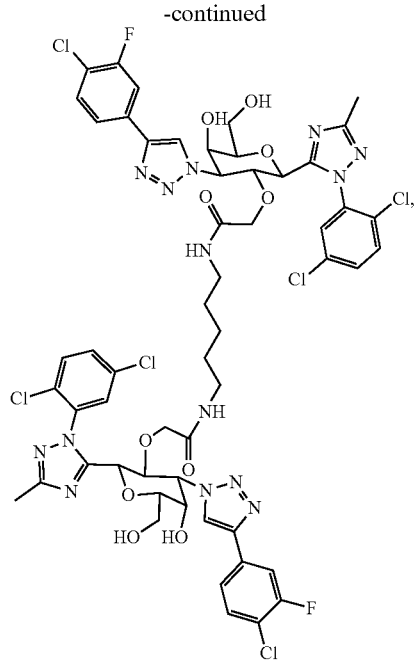
86
-continued
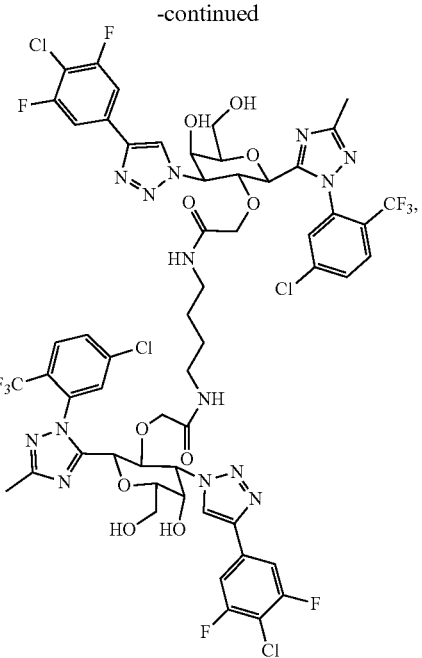
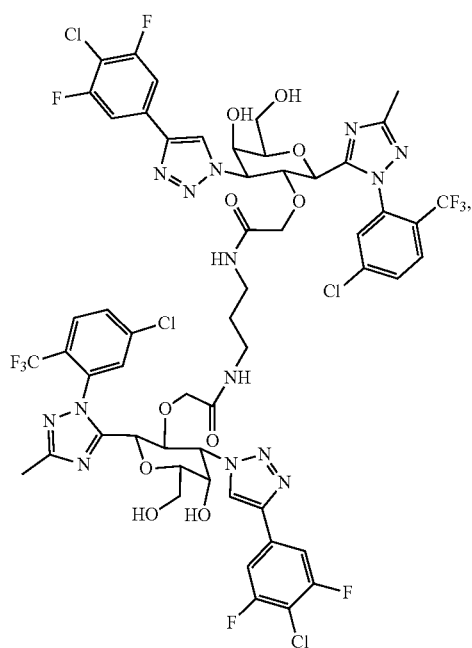
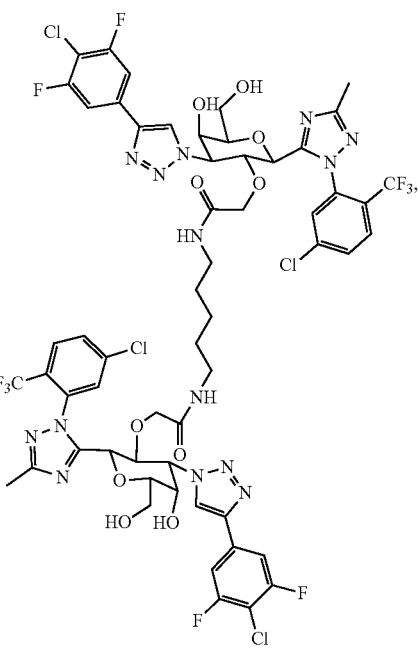

87
-continued
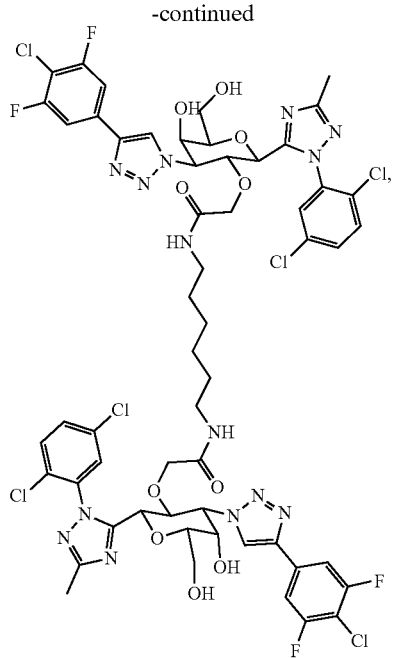
88
-continued
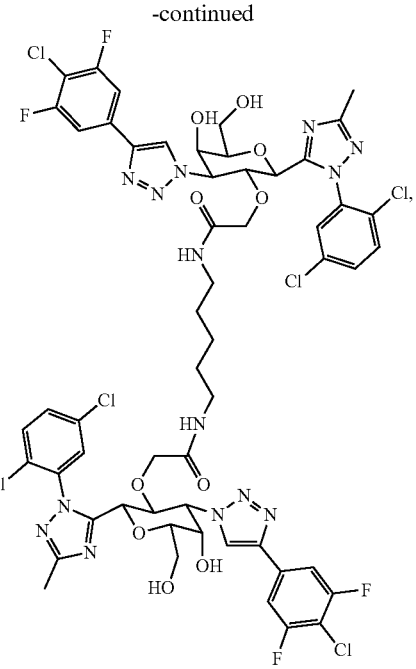
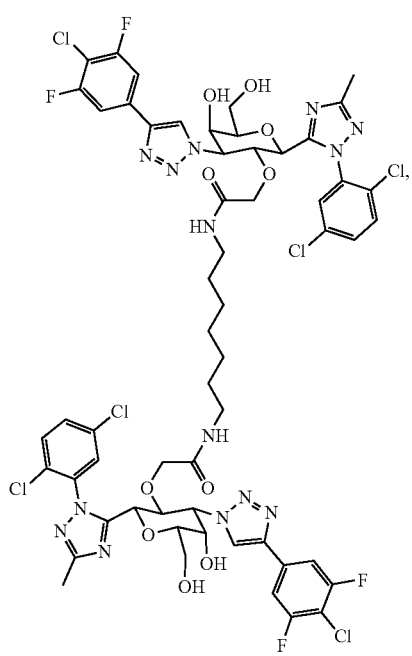
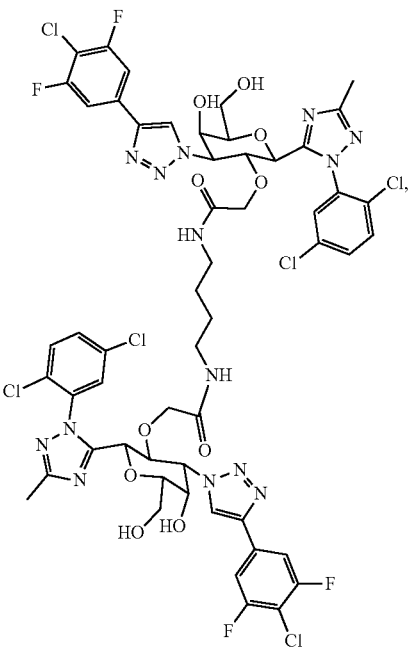

89
-continued
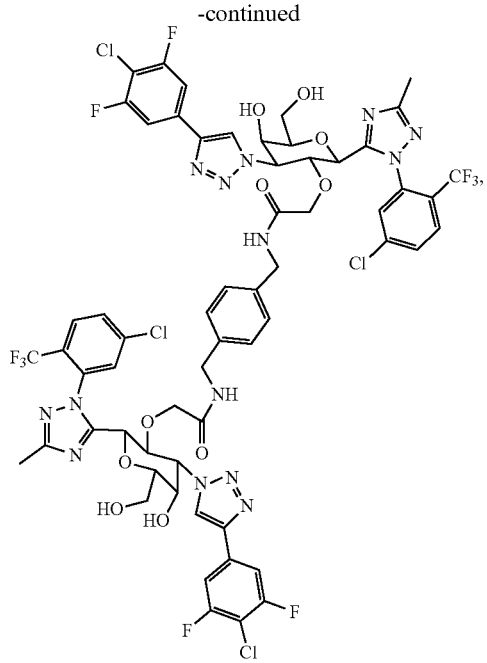
90
-continued
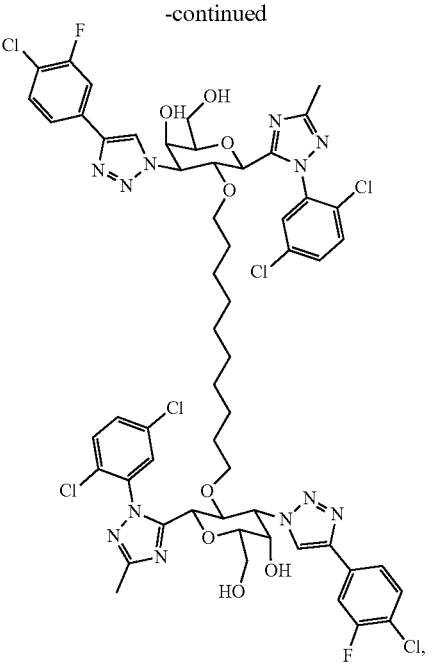
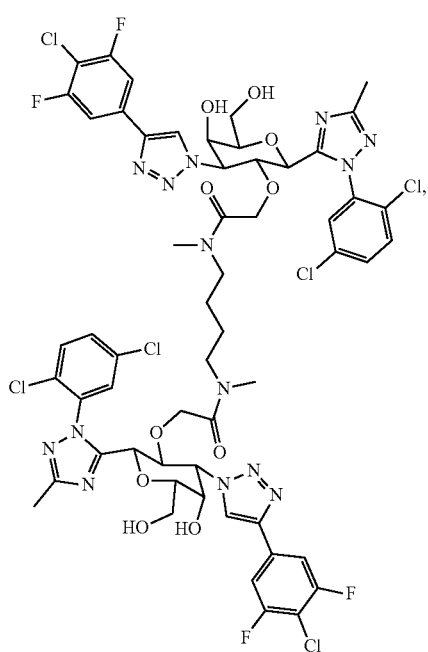
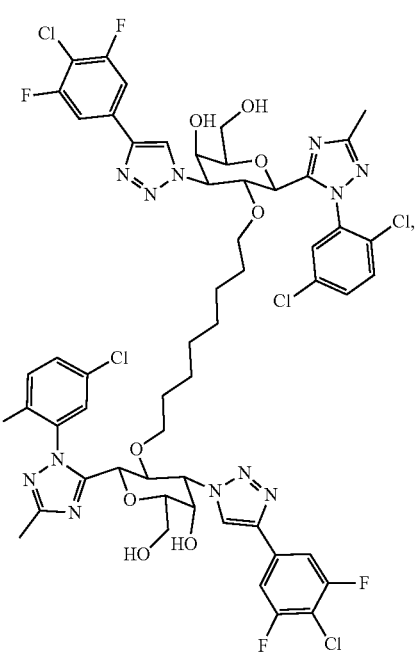

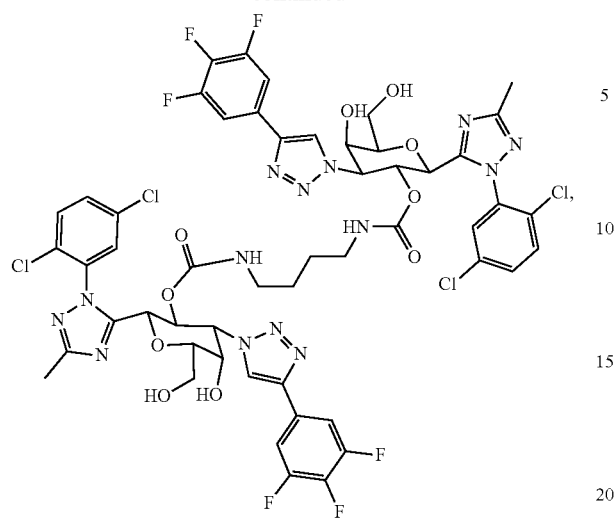
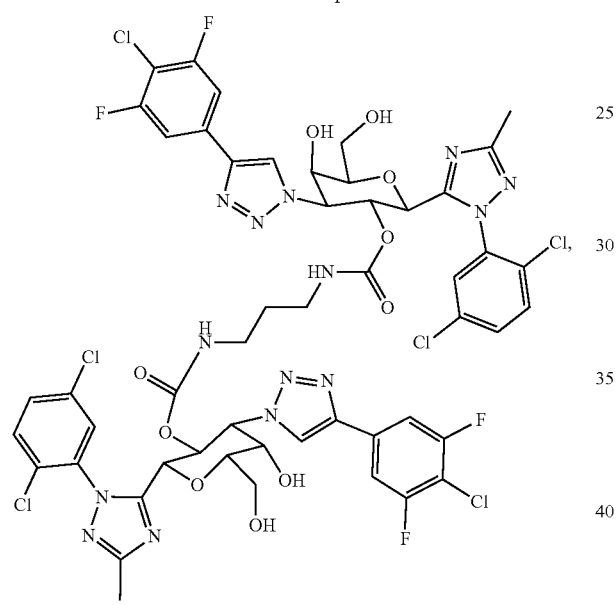
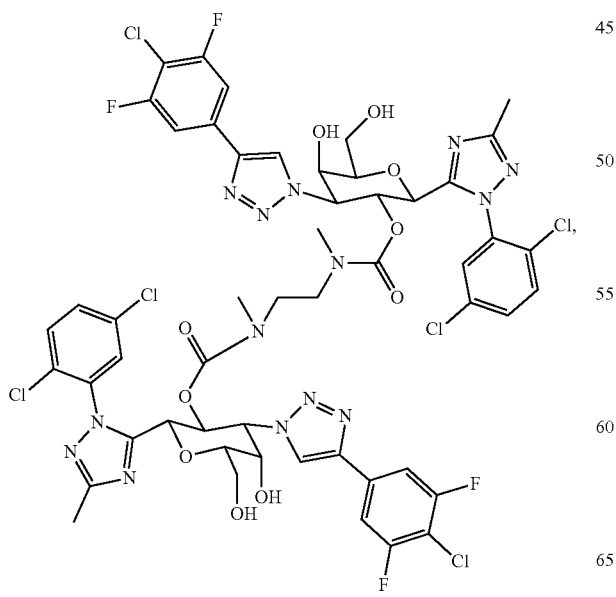
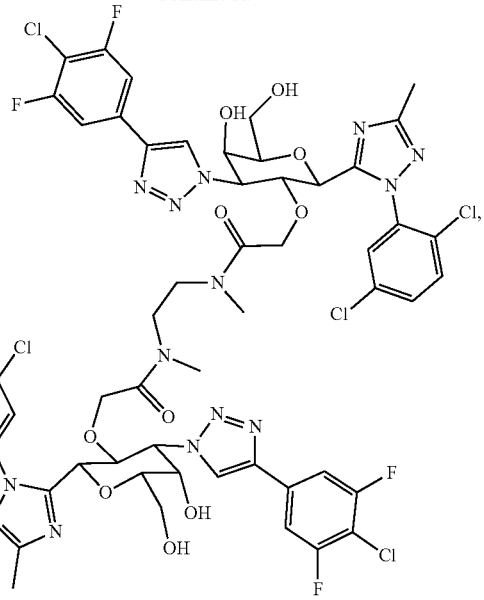
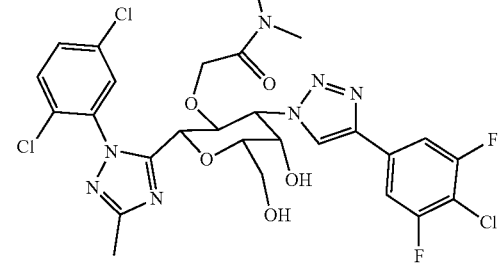
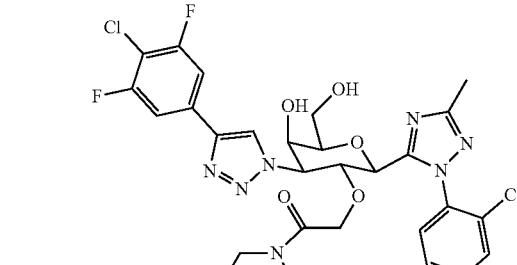
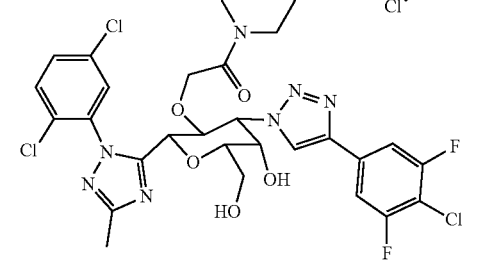

-continued

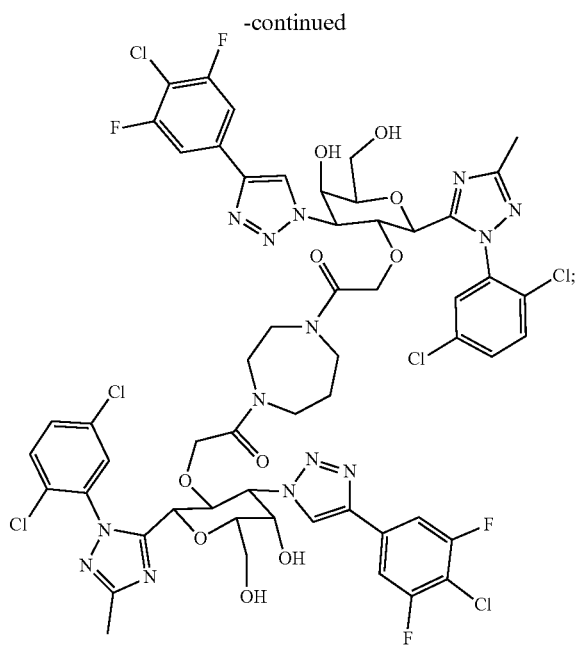

or a pharmaceutically acceptable salt thereof.

14. A composition comprising a therapeutically effective amount of a compound of claim 13, or a pharmaceutically acceptable salt thereof, and a pharmaceutically acceptable carrier.

15. A method for use in treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 13, or a pharmaceutically acceptable salt thereof, to a patient in need.

16. A method for treating a disease or condition selected from renal fibrosis, pulmonary fibrosis, hepatic fibrosis, arterial fibrosis, and systemic sclerosis; comprising administering a therapeutically effective amount of a compound of claim 13, a pharmaceutically acceptable salt thereof to a patient.

* * * * *